(12) United States Patent
Chen

(10) Patent No.: US 8,460,927 B2
(45) Date of Patent: Jun. 11, 2013

(54) B7-H1 ANTIBODIES AND METHOD OF USE

(75) Inventor: Lieping Chen, Hamden, CT (US)

(73) Assignee: Mayo Foundation for Medical Education and Research, Rochester ( * ) Notice: Subject to any disclaimer, the term of this patent is extended or adjusted under 35 U.S.C. 154(b) by 0 days.

(21) Appl. No.: 13/280,779

(22) Filed: Oct. 25, 2011

(65) Prior Publication Data

US 2012/0064626 A1   Mar. 15, 2012

Related U.S. Application Data

(63) Continuation of application No. 12/421,310, filed on Apr. 9, 2009, which is a continuation of application No. 12/347,492, filed on Dec. 31, 2008, which is a continuation of application No. 09/649,108, filed on Aug. 28, 2000, now abandoned, which is a continuation-in-part of application No. 09/451,291, filed on Nov. 30, 1999, now Pat. No. 6,803,192.

(51) Int. Cl.
*C12N 5/00* (2006.01)
*C07K 16/00* (2006.01)

(52) U.S. Cl.
USPC ........................................ 435/375; 530/387.1

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. |
| 4,034,074 A | 7/1977 | Miles |
| 4,036,945 A | 7/1977 | Haber |
| 4,098,876 A | 7/1978 | Piasio et al. |
| 4,233,402 A | 11/1980 | Maggio et al. |
| 4,257,774 A | 3/1981 | Richardson et al. |
| 4,272,398 A | 6/1981 | Jaffe |
| 4,331,647 A | 5/1982 | Goldenberg |
| 4,376,110 A | 3/1983 | David et al. |
| 4,469,863 A | 9/1984 | Ts'o et al. |
| 4,650,764 A | 3/1987 | Temin et al. |
| 4,769,330 A | 9/1988 | Paoletti et al. |
| 4,861,627 A | 8/1989 | Mathiowitz et al. |
| 4,861,719 A | 8/1989 | Miller |
| 4,925,673 A | 5/1990 | Steiner et al. |
| 4,946,778 A | 8/1990 | Ladner et al. |
| 4,980,289 A | 12/1990 | Temin et al. |
| 4,987,071 A | 1/1991 | Cech et al. |
| 5,013,556 A | 5/1991 | Woodle et al. |
| 5,124,263 A | 6/1992 | Temin et al. |
| 5,155,020 A | 10/1992 | Paoletti |
| 5,155,027 A | 10/1992 | Sledziewski et al. |
| 5,175,099 A | 12/1992 | Wills |
| 5,204,243 A | 4/1993 | Paoletti |
| 5,214,136 A | 5/1993 | Lin et al. |
| 5,218,105 A | 6/1993 | Cook et al. |
| 5,225,336 A | 7/1993 | Paoletti |
| 5,225,538 A | 7/1993 | Capon et al. |
| 5,235,033 A | 8/1993 | Summerton et al. |
| 5,240,846 A | 8/1993 | Collins et al. |
| 5,254,678 A | 10/1993 | Haseloff et al. |
| 5,278,056 A | 1/1994 | Bank et al. |
| 5,284,656 A | 2/1994 | Platz et al. |
| 5,296,347 A | 3/1994 | LaMotte, III |
| 5,451,569 A | 9/1995 | Wong et al. |
| 5,521,288 A | 5/1996 | Linsley et al. |
| 5,567,584 A | 10/1996 | Sledziewski et al. |
| 5,580,756 A | 12/1996 | Linsley et al. |
| 5,596,086 A | 1/1997 | Matteucci et al. |
| 5,674,704 A | 10/1997 | Goodwin et al. |
| 5,675,848 A | 10/1997 | Kappel |
| 5,714,147 A | 2/1998 | Capon et al. |
| 5,750,375 A | 5/1998 | Sledziewski et al. |
| 5,750,666 A | 5/1998 | Caruthers et al. |
| 5,843,725 A | 12/1998 | Sledziewski et al. |
| 5,858,776 A | 1/1999 | Ostrand-Rosenberg et al. |
| 5,861,310 A | 1/1999 | Freeman et al. |
| 5,874,240 A | 2/1999 | Ni et al. |
| 5,928,893 A | 7/1999 | Kang et al. |
| 5,942,607 A | 8/1999 | Freeman et al. |
| 6,018,026 A | 1/2000 | Sledziewski et al. |
| 6,210,669 B1 | 4/2001 | Aruffo et al. |
| 6,291,212 B1 | 9/2001 | Sledziewski et al. |
| 6,291,646 B1 | 9/2001 | Sledziewski et al. |
| 6,297,008 B1 | 10/2001 | Okamoto et al. |
| 6,300,099 B1 | 10/2001 | Sledziewski et al. |
| 6,303,121 B1 | 10/2001 | Kwon |
| 6,323,323 B1 | 11/2001 | Sledziewski et al. |
| 6,355,779 B1 | 3/2002 | Goodwin et al. |
| 6,423,885 B1 | 7/2002 | Waterhouse et al. |
| 6,458,934 B1 | 10/2002 | Hong et al. |
| 6,630,575 B2 | 10/2003 | Coyle et al. |
| 6,635,750 B1 | 10/2003 | Coyle et al. |
| 6,740,493 B1 | 5/2004 | Long et al. |
| 6,743,619 B1 | 6/2004 | Tang et al. |
| 6,803,192 B1 | 10/2004 | Chen |
| 6,808,710 B1 | 10/2004 | Wood et al. |
| 6,891,030 B2 | 5/2005 | Chen |
| 6,919,193 B2 | 7/2005 | Tang et al. |
| 6,936,704 B1 | 8/2005 | Freeman |
| 6,943,150 B1 | 9/2005 | Altieri |
| 6,965,018 B2 | 11/2005 | Mikesell |

(Continued)

FOREIGN PATENT DOCUMENTS

| CA | 2 383 424 A1 | 3/2001 |
| CA | 2 383 456 A1 | 3/2001 |

(Continued)

OTHER PUBLICATIONS

Abstract—EBI Database Accession No. AF177937 XP002269036 (version 1 accession date: Jan. 19, 2000).

(Continued)

*Primary Examiner* — Ilia Ouspenski

(74) *Attorney, Agent, or Firm* — Birch, Stewart, Kolasch & Birch, LLP

(57) ABSTRACT

The invention provides novel polypeptides useful for co-stimulating T cells, isolated nucleic acid molecules encoding them, vectors containing the nucleic acid molecules, and cells containing the vectors. Also included are methods of making and using these co-stimulatory polypeptides.

6 Claims, 31 Drawing Sheets

U.S. PATENT DOCUMENTS

| | | |
|---|---|---|
| 7,029,674 B2 | 4/2006 | Carreno |
| 7,030,219 B2 | 4/2006 | Pardoll et al. |
| 7,038,013 B2 | 5/2006 | Freeman |
| 7,041,474 B2 | 5/2006 | Kingsbury |
| 7,101,550 B2 | 9/2006 | Wood et al. |
| 7,105,328 B2 | 9/2006 | Wood et al. |
| 7,122,351 B2 | 10/2006 | Moore et al. |
| 7,258,354 B2 | 8/2007 | Kim |
| 7,279,567 B2 | 10/2007 | Mikesell et al. |
| 7,285,036 B2 | 10/2007 | Chang |
| 7,358,354 B2 | 4/2008 | Mikesell et al. |
| 7,368,531 B2 | 5/2008 | Rosen |
| 7,368,554 B2 | 5/2008 | Mikesell et al. |
| 7,381,794 B2 | 6/2008 | Moore et al. |
| 7,385,036 B2 | 6/2008 | Kingsbury |
| 7,411,051 B2 | 8/2008 | Rosen |
| 7,414,122 B2 | 8/2008 | Fox et al. |
| 7,432,059 B2 | 10/2008 | Freeman et al. |
| 7,432,062 B2 | 10/2008 | Coyle et al. |
| 7,432,351 B1 | 10/2008 | Chen |
| 7,449,300 B2 | 11/2008 | Chen |
| 7,560,540 B2 | 7/2009 | Pardoll et al. |
| 7,563,869 B2 | 7/2009 | Honjo et al. |
| 7,595,048 B2 | 9/2009 | Honjo et al. |
| 7,635,757 B2 | 12/2009 | Freeman et al. |
| 7,651,686 B2 | 1/2010 | Chen et al. |
| 7,709,214 B2 | 5/2010 | Freeman et al. |
| 7,723,479 B2 | 5/2010 | Mikesell et al. |
| 7,794,710 B2 | 9/2010 | Chen et al. |
| 8,039,589 B1 | 10/2011 | Chen |
| 8,053,414 B2 | 11/2011 | Pardoll et al. |
| 8,053,558 B2 | 11/2011 | Pardoll et al. |
| 8,114,845 B2 | 2/2012 | Langermann et al. |
| 8,163,550 B2 | 4/2012 | Chen et al. |
| 2002/0055139 A1 | 5/2002 | Holtzman |
| 2002/0091246 A1 | 7/2002 | Pardoll et al. |
| 2002/0095024 A1 | 7/2002 | Mikesell et al. |
| 2002/0102651 A1 | 8/2002 | Freeman |
| 2002/0106730 A1 | 8/2002 | Coyle et al. |
| 2002/0107363 A1 | 8/2002 | Fox et al. |
| 2002/0110836 A1 | 8/2002 | Freeman et al. |
| 2002/0164600 A1 | 11/2002 | Freeman et al. |
| 2002/0168719 A1 | 11/2002 | Kwon |
| 2003/0039653 A1 | 2/2003 | Chen et al. |
| 2003/0044768 A1 | 3/2003 | Wood |
| 2003/0142359 A1 | 7/2003 | Bean et al. |
| 2003/0171551 A1 | 9/2003 | Rosenblatt et al. |
| 2003/0208058 A1 | 11/2003 | Fiscella et al. |
| 2003/0232323 A1 | 12/2003 | Freeman et al. |
| 2004/0010134 A1 | 1/2004 | Rosen et al. |
| 2004/0109847 A1 | 6/2004 | Chen et al. |
| 2004/0247563 A1 | 12/2004 | Lynch et al. |
| 2005/0013811 A1 | 1/2005 | Chen et al. |
| 2005/0059051 A1 | 3/2005 | Chen |
| 2005/0228170 A1 | 10/2005 | Fox et al. |
| 2005/0260716 A1 | 11/2005 | Moore et al. |
| 2006/0034826 A1 | 2/2006 | Carreno et al. |
| 2006/0084794 A1 | 4/2006 | Rosen et al. |
| 2006/0110383 A1 | 5/2006 | Honjo et al. |
| 2006/0153841 A1 | 7/2006 | Freeman |
| 2006/0159685 A1 | 7/2006 | Mikesell et al. |
| 2006/0223088 A1 | 10/2006 | Rosen et al. |
| 2007/0037206 A1 | 2/2007 | Rosen et al. |
| 2007/0041963 A1 | 2/2007 | Rosen et al. |
| 2007/0065427 A1 | 3/2007 | Freeman et al. |
| 2007/0092504 A1 | 4/2007 | Carreno et al. |
| 2007/0099833 A1 | 5/2007 | Rosen et al. |
| 2007/0122378 A1 | 5/2007 | Freeman et al. |
| 2007/0197904 A1 | 8/2007 | Viglianti et al. |
| 2007/0224663 A1 | 9/2007 | Rosen et al. |
| 2007/0231344 A1 | 10/2007 | Leadbetter et al. |
| 2008/0025979 A1 | 1/2008 | Honjo et al. |
| 2008/0118511 A1 | 5/2008 | Freeman et al. |
| 2008/0213778 A1 | 9/2008 | Holtzman |
| 2008/0226662 A1 | 9/2008 | Pardoll et al. |
| 2008/0241175 A1 | 10/2008 | Pardoll et al. |
| 2009/0042292 A1 | 2/2009 | Chen |
| 2009/0075338 A1 | 3/2009 | Moore et al. |
| 2009/0176317 A1 | 7/2009 | Kwon et al. |
| 2009/0215084 A1 | 8/2009 | Kwon et al. |
| 2009/0269783 A1 | 10/2009 | Coyle et al. |
| 2009/0274666 A1 | 11/2009 | Chen |
| 2009/0317368 A1 | 12/2009 | Chen |
| 2010/0015642 A1 | 1/2010 | Kwon et al. |
| 2011/0020325 A1 | 1/2011 | Kwon et al. |
| 2012/0065374 A1 | 3/2012 | Pardoll et al. |
| 2012/0065385 A1 | 3/2012 | Pardoll et al. |

FOREIGN PATENT DOCUMENTS

| | | |
|---|---|---|
| CA | 2 389 722 A1 | 5/2001 |
| EP | 1074617 A2 | 2/2001 |
| EP | 1 456 652 | 9/2004 |
| EP | 1537878 A1 | 6/2005 |
| WO | WO 90/07861 A1 | 7/1990 |
| WO | WO 91/10741 A1 | 7/1991 |
| WO | WO 91/11465 A1 | 8/1991 |
| WO | WO 91/17271 A1 | 11/1991 |
| WO | WO 92/00092 A1 | 1/1992 |
| WO | WO 92/01047 A1 | 1/1992 |
| WO | WO 92/20791 A1 | 11/1992 |
| WO | WO 93/01222 A1 | 1/1993 |
| WO | WO 95/05646 A1 | 2/1995 |
| WO | WO 95/07707 A1 | 3/1995 |
| WO | WO 96/29348 A1 | 9/1996 |
| WO | WO 97/17613 A1 | 5/1997 |
| WO | WO 97/17614 A1 | 5/1997 |
| WO | WO 97/24447 A1 | 7/1997 |
| WO | WO 98/16249 A1 | 4/1998 |
| WO | WO 98/23635 A1 | 6/1998 |
| WO | WO 98/33914 A1 | 8/1998 |
| WO | WO 98/36096 A1 | 8/1998 |
| WO | WO 99/36093 A1 | 7/1999 |
| WO | WO 99/64597 A1 | 12/1999 |
| WO | WO 00/29445 A1 | 5/2000 |
| WO | WO 00/29582 A2 | 5/2000 |
| WO | WO 00/41508 A2 | 7/2000 |
| WO | WO 00/55375 A1 | 9/2000 |
| WO | WO 00/61612 A2 | 10/2000 |
| WO | WO 01-07611 | 2/2001 |
| WO | WO 01-14556 | 3/2001 |
| WO | WO 01/14557 A1 | 3/2001 |
| WO | WO 01/34768 A2 | 5/2001 |
| WO | WO 01/35629 A1 | 5/2001 |
| WO | WO 01/62905 A2 | 8/2001 |
| WO | WO 01/70979 A2 | 9/2001 |
| WO | WO 01/83750 A2 | 11/2001 |
| WO | WO 01/94413 A2 | 12/2001 |
| WO | WO 02-00692 | 1/2002 |
| WO | WO 02-00730 | 1/2002 |
| WO | WO 02/02587 A1 | 1/2002 |
| WO | WO 02/02891 A1 | 1/2002 |
| WO | WO 02/08279 A2 | 1/2002 |
| WO | WO 02/24891 A2 | 3/2002 |
| WO | WO 02/46449 A2 | 6/2002 |
| WO | WO 02/057453 A2 | 7/2002 |
| WO | WO 02/078731 A1 | 10/2002 |
| WO | WO 02/079474 A2 | 10/2002 |
| WO | WO 02/081731 A2 | 10/2002 |
| WO | WO 02/086083 A2 | 10/2002 |
| WO | WO 03/006632 A2 | 1/2003 |
| WO | WO 03/008583 A2 | 1/2003 |
| WO | WO 03/049755 A1 | 6/2003 |
| WO | WO 2004/004771 A1 | 1/2004 |
| WO | WO 2004/077060 A2 | 9/2004 |
| WO | WO 2006/050172 A2 | 5/2006 |
| WO | WO 2006/133396 A2 | 12/2006 |
| WO | WO 2007-100098 | 9/2007 |
| WO | WO 2008/037080 A1 | 4/2008 |
| WO | WO 2008/083174 A2 | 7/2008 |
| WO | WO 2009/023566 A2 | 2/2009 |
| WO | WO 2009/029342 A2 | 3/2009 |
| WO | WO 2009/114110 A1 | 9/2009 |
| WO | WO 2010/027423 A2 | 3/2010 |
| WO | WO 2010/027827 A2 | 3/2010 |
| WO | WO 2010/027828 A2 | 3/2010 |
| WO | WO 2010/098788 A2 | 9/2010 |
| WO | WO 2011/066342 A2 | 6/2011 |

OTHER PUBLICATIONS

Abstract—UNIPROT Database Accession No. Q9EP73 XP002269038 (Version 1 accession date: Mar. 1, 2001.
Abstract—UNIPROT Database Accession No. Q9NZQ7 XP002269037 (version 1 accession date Oct. 1, 2000).
Azuma et al., "B70 antigen is a second ligand for CTLA-4 and CD28," Nature (1993) vol. 366, pp. 76-79.
Bajorath et al., "Immunoglobulin fold characteristics of B7-1 (CD80) and B7-2(CD86)," Protein Science (1994) vol. 3, pp. 2148-2150.
Coyle et al., Nature Immunol. (2001), vol. 2, pp. 203-209.
Dong et al, "B7-H1, a third member of the B7 family, co-stimulates T-cell proliferation and interleukin-10 secretion," Nature Medicine (Dec. 1999) vol. 5, No. 12, pp. 1365-1369.
Experimental Data generated by a licensee of the present application.
Fargeas et al., "Identification of Residues in the v Domain of CD80 (B7-1) Implicated in Functional Interactions with CD28 and CTLA4," J. Exp. Med. (1995), vol. 182, pp. 667-675.
Freeman et al., "B7, A New Member of the Ig Superfamily with Unique Expression on Activated and Neoplastic B Cells," The Journal of Immunology (1989) vol. 143, pp. 2714-2722.
Office Action issued Jul. 14, 2011, in Canadian Patent Application No. 2,392,447.
U.S. Appl. No. 60/164,344, filed Nov. 9, 1999.
U.S. Appl. No. 60/195,296, filed Apr. 7, 2000.
U.S. Appl. No. 60/221,367, filed Jul. 27, 2000.
Freeman et al., "B7-1 and B7-2 Do Not Deliver Identical Costimulatory Signals, . . . Production of IL-4," Immunity (1995) vol. 2, pp. 523-532.
Freeman et al., "Cloning of B7-2: A CTLA-4 Counter-Receptor that Costimulates Human T Cell Proliferation," Science (1993) vol. 262, pp. 909-911.
Freeman et al., "Engagement of the PD-1 Immunoinhibillory Receptor by a Novel B7 Family Member Leads to Negative Regulation of Lymphoctye Activation," J. Exp. Med. (Oct. 2000) vol. 192, No. 7, pp. 1027-1034.
Freeman et al., "Murine B7-2, an Alternative CTLA4 Counter-receptor that Costimulates T Cell Proliferation and Interleukin 2 Production," J. Exp. Med. (1993) vol. 178, pp. 2185-2192.
Freeman et al., "Structure, Expression, and T Cell Costimulatory Activity of the Murine Homologue . . . Antigen B7," J. Exp. Med. (1991) vol. 174, pp. 625-631.
Henry et al., "Structure and evolution of the extended B7 family," Immunol. Today (Jun. 1999) vol. 20, No. 6, pp. 285-288.
Inaba et al., "The Tissue Distribution of the B7-2 Costimulator in Mice: Abundant Expression on Dendritic Cells . . . In Vitro," J. Exp. Med. (1994) vol. 180, pp. 1849-1860.
Juppner; Bone (1995) vol. 17, pp. 39S-42S.
Kato et al., Psychiatry Research (2009) vol. 167, pp. 97-105.
Lederman et al., "A single amino acid substitution in a common African allele of the CD4 molecule ablates binding of the monoclonal antibody, OKT4," Molecular Immunology (1991) vol. 28, No. 11, pp. 1171-1181.
Li et al., "Beta Endorphin omission analogs: Dissociation of immunoreactivity from other biological activities," PNAS (Jun. 1980) vol. 77, No. 6, pp. 3211-3214.
Metzler et al., Nature Structural Biol. (1997) vol. 4, pp. 527-531.
NCBI Sequence Database Entry. Accession No. AA292201 (Aug. 8, 1997).
NCBI Sequence Database Entry. Accession No. AA823166 (Feb. 17, 1998).
NCBI Sequence Database Entry. Assession No. AA896104 (Apr. 6, 1998).
Office Action issued Jul. 14, 2011, in Canadian Patent Application No. 2,392,477.
Romanos et al; DNA Cloning 2: A Practical Approach, Chapter 5, IRL Press, Oxford, 1995, pp. 133-148.
Russell et al., J. Mol. Biol. (1994) vol. 244, pp. 332-350.
Sequence Alignment, 2010, 4 pages.
Skolnick et al., Trends in Biotech. (2000) vol. 18, No. 1, pp. 34-39.
Swallow et al., "B7H a Novel Costimulatory Homolog of B7.1 and B7.2 is induced by TNFalpha," Infec. and Immun. (Oct. 1999) vol. 11, pp. 423-432.
U.S. Appl. No. 09/399,723, filed Sep. 20, 1995.
U.S. Appl. No. 60/164,897, filed Nov. 10, 1999.
U.S. Appl. No. 61/150,390, filed Aug. 23, 1999.
Abbaszadegan et al., "Analysis of Multidrug Resistance-associated Protein (MRP) Messenger RNA in Normal and Malignant Hematopoietic Cells," Cancer Research, vol. 54, Sep. 1, 1994, pp. 4676-4679.
Acsadi et al., "Direct gene transfer and expression into rat heart in vivo," The New Biologist, vol. 3, No. 1, Jan. 1991, pp. 71-81.
Adachi et al., "Enhanced and accelerated lymphoproliferation is Fas-null mice.," Proc. Natl. Acad. Sci. USA, vol. 93, Mar. 1996, pp. 2131-2136.
Adachi et al., "Aberrant transcription caused by the insertion of an early transposable element in an intron of the Fas antigen gene of Ipr mice," Proc. Natl. Acad. Sci. USA, vol. 90, Mar. 1993, pp. 1756-1760.
Agata et al., "Expression of the PD-1 antigen on the surface of stimulated mouse T and B lymphocytes", International Immunology, vol. 8, No. 5, 1996, pp. 765-772.
Alderson et al., "Molecular and biological characterization of human 4-1BB and its ligand," Eur. J. Immunol., vol. 24, 1994, pp. 2219-2227.
Aldovini et al., "Humoral and cell-mediated immune responses to live recombinant BCG-HIV vaccines," Nature, vol. 351, Jun. 6, 1991, pp. 479-482.
Ambrosini et al., "A novel anti-apoptosis gene, survivin, expressed in cancer and lymphoma," Nature Medicine, vol. 3, No. 8, Aug. 1997, pp. 917-921.
Anderson, "Human Gene Therapy," Science, vol. 256, May 8, 1992, pp. 808-813.
Ansari et al., "The programmed death-1 (PD-1) pathway regulates autoimmune diabetes in nonobese diabetic (NOD) mice," J. Exp. Med., vol. 198, No. 1, Jul. 7, 2003, pp. 63-69.
Anukam et al., "Augmentation of antimicrobial metronidazole therapy of bacterial vaginosis with oral probiotic *Lactobacillus rhamnosus* GR-1 and *Lactobacillus reuteri* RC-14: randomized, double-blind, placebo controlled trial," Microbes and Infection, 2006, pp. 1-5.
ASCO 2010 Press Release, "Ipilimumab Improves Survival for Patients with Metastatic Melanoma," ASCO Meeting, Jun. 2010, 1 page.
Bajorath et al., "Molecular modeling of CD28 and three-dimensional analysis of residue conservation in the CD28/CD152 family", Journal of Molecular Graphics and Modelling, vol. 15, 1997, pp. 135-139.
BD PharmingenTM Technical Data Sheet, "Purified Rat Anti-Mouse Ly-6G (Gr-1) Monoclonal Antibody for Immunohistochemistry (IHC)," 2003, 1 page.
Bell, "B7h and B7-H1: new members of the B7 family", Immunology Today, vol. 21, No. 1, Feb. 2000, p. 59.
Benita et al., "Characterization of drug-loaded poly(d,l-lactide) microspheres," Journal of Pharmaceutical Sciences, vol. 73, No. 12, Dec. 1984, pp. 1721-1724.
Benlalam et al., "Comprehensive analysis of the frequency of recognition of melanoma-associated antigen (MAA) by CD8 melanoma infiltrating lymphocytes (TIL) implications for immunotherapy," Eur. J. Immunol., vol. 31, 2001, pp. 2007-2015.
Berman et al., "The Protein Data Bank", Nucleic Acids Research, 2000, vol. 28, No. 1, pp. 235-242.
Blank et al., "Blockade of PD-L1 (B7-H1) augments human tumor-specific T cell responses in vitro," Int. J. Cancer, vol. 119, 2006, pp. 317-327 (Published online Feb. 16, 2006).
Blazar et al., "Infusion of Anti-B7.1 (CD80) and Anti-B7.2 (CD86) Monoclonal Antibodies Inhibits Murine Graft-Versus-Host Disease Lethality In Part Via Direct Effects on CD4+ and CD8+ T Cells", Journal of Immunology, vol. 157, 1996, pp. 3250-3259.
Bodey et al., "Failure of Cancer Vaccines: The Significant Limitations of this Approach to Immunotherapy," Anticancer Research, vol. 20, 2000, pp. 2665-2676.
Bodey, "Genetically engineered antibodies for direct antineoplastic treatment and systematic delivery of various therapeutic agents to cancer cells," Expert Opin. Biol. Ther., vol. 1, No. 4, 2001, pp. 603-617.

Boletta et al., "High Efficient Non-Viral Gene Delivery to the Rat Kidney by Novel Polycationic Vectors," J. Am Soc. Nephrol., vol. 7, No. 9, Abstract A2409, S462 (PS), Sep. 1996, p. 1728.

Bona et al., "Immune response: Idiotype anti-idiotype network," CRC Critical Reviews in Immunology, Mar. 1981, pp. 33-73.

Bonfoco et al.,"Inducible nonlymphoid expression of Fas ligand is responsible for superantigen-induced peripheral deletion of T cells," Immunity, vol. 9, No. 5, 1998, pp. 711-720.

Bonifaz et al., "Efficient targeting of protein antigen to the dendritic cell receptor DEC-205 in the steady state leads to antigen presentation on major histocompatibility complex class I products and peripheral CD8+ T cell tolerance," J. Exp. Med, vol. 196, No. 12, Dec. 16, 2002, pp. 1627-1638.

Bonifaz et al., "In vivo targeting of antigens to maturing dendritic cells via the DEC-205 receptor improves T cell vaccination," J. Exp. Med, vol. 199, No. 6, Mar. 15, 2004, pp. 815-824.

Boon et al., "Human T Cell Responses Against Melanoma", Annu. Rev. Immunol., vol. 24, 2006, pp. 175-208 (Published online Dec. 1, 2005).

Boon, "Toward a Genetic Analysis of Tumor Rejection Antigens," Advances in Cancer Research, vol. 58, 1992, pp. 177-210.

Bovo et al., "Immune-mediated inner ear disease", Acta Oto-Laryngologica, vol. 126, 2006, pp. 1012-1021.

Bowie et al., "Deciphering the Message in Protein Sequences: Tolerance to Amino Acid Substitutions," Science, vol. 247, 1990, pp. 1306-1310.

Brahmer et al., "Safety and activity of MDX-1106 (ONO-4538), an anti-PD-1 monoclonal antibody, in patients with selected refractory or relapsed malignancies", J. Clin. Oncol., vol. 26, Suppl., Abstr. 3006, May 20, 2008, 2 pages.

Braquet et al., "Effect of Endothelin-1 on Blood Pressure and Bronchopulmonary System of the Guinea Pig," Journal of Cardiovascular Pharmacology, vol. 13, Suppl. 5, 1989, pp. S143-S146.

Britton et al., "Leprosy," The Lancet, vol. 363, Apr. 10, 2004, pp. 1209-1219.

Brown et al., "Blockade of programmed death-1 ligands on dendritic cells enhances T cell activation and cytokine production," The Journal of Immunology, vol. 170, 2003, pp. 1257-1266.

Bubenik, "Genetically engineered dendritic cell-based cancer vaccines (Review)", International Journal of Oncology, vol. 18, 2001, pp. 475-478, XP001056627.

Burgess et al., "Activities of Heparin-binding (Acidic Fibroblast) Growth Factor-1 from Its Receptor-binding Activities by Site-directed Mutagenesis of a Single Lysine Residue," The Journal of Cell Biology, vol. 111, Nov. 1990, pp. 2129-2138.

Burmer et al., "Frequence and Spectrum of c-Ki-ras Mutations in Human Sporadic Colon Carcinoma, Carcinomas Arising in Ulcerative Colitis, and Pancreatic Adenocarcinoma," Environmental Health Perspectives, vol. 93, 1991, pp. 27-31.

Buskens et al., "Adenocarcinomas of the Gastro-Esophageal Junction: A Comparative Study of the Gastric Cardia and the Esophagus with Respect to Cyclooxygenase-2 Expression," Digestive Disease Week Abstracts and Itinerary Planner, Abstract No. 850.2003.2003, 2003.

Butte et al., "Interaction of human PD-L1 and B7-1," Molecular Immunology, vol. 45, 2008, pp. 3567-3572 (Published online Jun. 27, 2008).

Cairns et al., "Immortalization of multipotent growth-factor dependent hemopoietic progenitors from mice transgenic for GATA-1 driven SV40 tsA58 gene," The EMBO Journal, vol. 13, No. 19, 1994, pp. 4577-4586.

Carreno et al., "The B7 family of ligands and its receptors: new pathways for costimulation and inhibition of immune responses," Annu. Rev. Immunol., vol. 20, 2002, pp. 29-53.

Carter et al., "PD-1:PD-L inhibitory pathways affects both CD4+ and CD8+ T cells and is overcome by IL-2," Eur. J. Immunol., vol. 32, 2002, pp. 634-643.

Carter et al., "Humanization of an anti-p185HER2 antibody for human cancer therapy," Proc. Natl. Acad. Sci. USA, vol. 89, May 1992, pp. 4285-4289.

Chakrabarti et al., "Vaccinia virus expression vector: coexpression of β-galactosidase provides visual screening of recombinant virus plaques," Molecular and Cellular Biology, vol. 5, No. 12, Dec. 1985, pp. 3403-3409.

Chambers et al., "Co-stimulation in T cell responses," Current Opinion in Immunology, vol. 9, 1997, pp. 396-404.

Chapoval et al., "B7-H3: A costimulatory molecule for T cell activation and IFN-γ production," Nature Immunology, vol. 2, No. 3, Mar. 2001, pp. 269-274.

Chaurand et al., "Peptide and Protein Identification by Matrix-Assisted Laser Desorption Ionization (MALDI) and MALDI-Post-Source Decay Time-of-Flight Mass Spectrometry," J Am Soc Mass Spectrom, vol. 10, 1999, pp. 91-103.

Chen et al., "CD44-deficient mice exhibit enhanced hepatitis after concanavalin A injection: evidence for involvement of CD44 in activation-induced cell death," The Journal of Immunology, vol. 166, 2001, pp. 5889-5897.

Chen et al., "Costimulation of antitumor immunity by the B7 counter-receptor of the T lymphocyte molecules CD28 and CTLA-4," Cell, vol. 71, Dec. 24, 1992, pp. 1093-1102.

Chen et al., "Tumor immunogenicity determines the effect of B7 costimulation on T cell-mediated tumor immunity," J. Exp. Med., vol. 179, Feb. 1994, pp. 523-532.

Chen, "Co-inhibitory molecules of the B7-CD28 family in the control of T-cell immunity," Nature Reviews, Immunology, vol. 4, May 2004, 336-347.

Cheville et al., "Comparisons of Outcome and Prognostic Features Among Histologic Subtypes of Renal Cell Carcinoma," Am. J. Surg. Pathol., vol. 27, No. 5, 2003, pp. 612-624.

Choi et al., "Genomic Organization and Expression Analysis of B7-H4, an Immune Inhibitory Molecule of the B7 Family," The Journal of Immunology, vol. 171, 2003, pp. 4650-4654.

Clinical Trials Database on phase 1 clinical trials using an anti-hB7-H1 monoclonal antibody (ID No. NCT00729664), 2009.

ClinicalTrials.gov., Study of MDX-1105 in Subjects with Selected Advanced or Recurrent Solid Tumors (MDX1105-01), verified by Bristol-Myers Squibb, Mar. 29, 2010.

Cogoni et al., "Gene silencing in Neurospora crassa requires a protein homologous to RNA-dependent RNA polymerase," Nature, vol. 399, May 13, 1999, pp. 166-169.

Cogoni et al., "Transgene silencing of the al-1 gene in vegetative cells of Neurospora is mediated by a cytoplasmic effector and does not depend on DNA-DNA interactions or DNA methylation," The EMBO Journal, vol. 15, No. 12, 1996, pp. 3153-3163.

Cohen et al., "Lpr and gld: Single Gene Models of Systemic Autoimmunity and Lymphoproliferative Disease," Annu. Rev, Immunol., vol. 9, 1991, pp. 243-269.

Cole et al., "The EBV-Hybridoma Technique and its Application to Human Lung Cancer," Monoclonal Antibodies and Cancer Therapy, 1985, pp. 77-96.

Collins et al., "The B7 family of immune-regulatory ligands," Genome Biology, vol. 6, Issue 6, Article 223, May 31, 2005, pp. 223.1-223.7.

Cone et al., "High-efficiency gene transfer into mammalian cells: Generation of helper-free recombinant retrovirus with broad mammalian host range," Proc. Natl. Acad Sci. USA, vol. 81, Oct. 1984, pp. 6349-6353.

Connolly, "Analytical Molecular Surface Calculation," Journal of Applied Crystallography, vol. 16, 1983, pp. 548-558.

Corpet, "Multiple sequence alignment with hierachical clustering," Nucleic Acids Research, vol. 16, No. 22, 1988, pp. 10881-10890.

Cote et al., "Generation of human monoclonal antibodies reactive with cellular antigens," Proc. Natl. Acad. Sci. USA, vol. 80, Apr. 1983, pp. 2026-2030.

Crispe et al., "The liver as a site of T-cell apoptosis: graveyard, or killing field?", Immunological Reviews, vol. 174, 2000, pp. 47-62.

Crispe, "Hepatic T Cells and Liver Tolerance," Nature Reviews, Immunology, vol. 3, Jan. 2003, pp. 51-62.

Cristiano et al., "Molecular conjugates: a targeted gene delivery vector for molecular medicine," J. Mol. Med., vol. 73, 1995, pp. 479-486.

Crystal, "Gene therapy strategies for pulmonary disease," The American Journal of Medicine, vol. 92, Suppl. 6A, Jun. 22, 1992, pp. 6A-44S to 6A-52S.
Curiel et al., "Blockade of B7-H1 improves myeloid dendritic cell-mediated antitumor immunity," Nature Medicine, vol. 9, No. 5, May 2003, pp. 562-567 (Published online Apr. 21, 2003).
Dao et al., "Involvement of CD1 in peripheral deletion of T lymphocytes is independent of NK T cells," The Journal of Immunology, vol. 166, 2001, pp. 3090-3097.
Database EM-HUM [Online] EMBL; Accession No. AK001872, Feb. 22, 2000.
Database EM-MUS [Online]EMBL; Accession No. AF142780.1 (version 1), Jun. 1, 1999.
Davidson et al., "Phenotypic, functional, and molecular genetic comparisons of the abnormal lymphoid cells of C3H-Ipr/Ipr and C3H-gld/gld MICE," The Journal of Immunology, vol. 136, No. 11, Jun. 1, 1986, pp. 4075-4084.
De St. Groth et al., "Production of monoclonal antibodies: strategy and tactics," Journal of Immunology Methods, vol. 35, 1980, pp. 1-21.
Debs et al., "Lung-specific delivery of cytokines induces sustained pulmonary and systemic immunomodulation in rats," The Journal of Immunology, vol. 140, No. 10, May 15, 1988, pp. 3482-3488.
Dheda et al., "Lung remodelling in pulmonary tuberculosis," J. Infect. Dis., vol. 192, Oct. 1, 2005, pp. 1201-1210.
Diehl et al., "In Vivo Triggering Through 4-1BB Enables Th-Independent Priming of CTL in the Presence of an Intact CD28 Costimulatory Pathway", The Journal of Immunology, vol. 168, 2002, pp. 3755-3762, XP002238986.
Ding et al., "Release of Reactive Nitrogen Intermediates and Reactive Oxygen Intermediates from Mouse Peritoneal Macrophages," The Journal of Immunology, vol. 141, No. 7, Oct. 1, 1988, pp. 2407-2412.
Dini, "Recognizing death: liver phagocytosis of apoptotic cells," Eur. J. Histochem., vol. 44, 2000, pp. 217-227.
Dong et al., "Immune regulation by novel costimulatory molecules," Immunologic Research, vol. 28, No. 1, 2003, pp. 39-48.
Dong et al., "B7-H1 determines accumulation and deletion of intrahepatic CD8+ T lymphocytes," Immunity, vol. 20, Mar. 2004, pp. 327-336.
Dong et al., "B7-H1 pathway and its role in the evasion of tumor immunity," J Mol Med, vol. 81, 2003, pp. 281-287 (Published online Apr. 30, 2003).
Dong et al., "Costimulating aberrant T cell responses by B7-H1 autoantibodies in rheumatoid arthritis", The Journal of Clinical Investigation, vol. 111, No. 3, Feb. 2003, pp. 363-370.
Dong et al., "Tumor-associated B7-H1 promotes T-cell apoptosis: A potential mechanism of immune evasion", Nature Medicine, vol. 8, No. 8, Aug. 2002, pp. 793-800.
Dudler et al., "Gene transfer of programmed death Ligand-I.Ig prolongs cardiac allograft survival," Transplantation, vol. 82, No. 12, Dec. 27, 2006, pp. 1733-1737, XP008088691.
Dunussi-Joannopoulos et al., "Gene Therapy with B7.1 and GM-CSF Vaccines in a Murine AML Model," Journal of Pediatric Hematology/Oncology, vol. 19, No. 6, 1997, pp. 536-540.
Ehl et al., "Different susceptibility of cytotoxic T cells to CD95 (Fas/Apo-1) ligand-mediated cell death after activation in vitro versus in vivo," The Journal of Immunology, vol. 156, 1996, pp. 2357-2360.
EMBL-EBI Accession No. AF 142780.2 (version 2, accessed Sep. 28, 2009), (Jun. 1, 1999).
EMBL-EBI Accession No. Q9WUL5 (Nov. 1, 1999).
Engh et al., "Accurate Bond and Angle Parameters for X-ray Protein Structure Refinement", Acta Cryst., vol. A47, 1991, pp. 392-400.
Falkner et al., "pUV I: a new vaccinia virus insertion and expression vector," Nucleic Acids Research, vol. 15, No. 17, 1987, p. 7192.
FDA News Release, "FDA Approves a Cellular Immunotherapy for Men with Advanced Prostate Cancer," Apr. 29, 2010, 1 page.
Fechteler et al., "Prediction of Protein Three-dimensional Structures in Insertion and Deletion Regions: A Procedure for Searching Data Bases of Representative Protein Fragments Using Geometric Scoring Criteria,", J. Mol. Biol., vol. 253, 1995, pp. 114-131.

Figlin et al., "Treatment of Metastatic Renal Cell Carcinoma with Nephrectomy, Interleukin-2 and Cytokine-Primed or CD8(+) Selected Tumor Infiltrating Lymphocytes From Primary Tumor," The Journal of Urology, vol. 158, Sep. 1997, pp. 740-745.
Finck et al., "Treatment of Murine Lupus with CTLA4Ig," Science, vol. 265, Aug. 26, 1994, pp. 1225-1227.
Fire et al., "Potent and specific genetic interference by double-stranded RNA in *Caenorhabditis elegans*," Nature, vol. 391, Feb. 19, 1998, pp. 806-811.
Fleming et al., "Selective Expression of Ly-6G on Myeloid Lineage Cells in Mouse Bone Marrow," The Journal of Immunology, vol. 151, No. 5, Sep. 1, 1993, pp. 2399-2408.
Foell et al., "CD137 costimulatory T cell receptor engagement reverses acute disease in lupus-prone NZB × NZW F1 mice," The Journal of Clinical Investigation, vol. 111, No. 10, May 2003, pp. 1505-1518.
Foell et al., "CD137-Mediated T Cell Co-Stimulation Terminates Existing Autoimmune Disease in SLE-Prone NZB/NZW F1 Mice," Ann. N.Y. Acad. Sci., vol. 987, 2003, pp. 230-235, XP009028987.
Fortugno et al., "Survivin exists in immunochemically distinct subcellular pools and is involved in spindle microtubule function," Journal of Cell Science, vol. 115, 2002, pp. 575-585.
Frank et al., "An Outcome Prediction Model for Patients With Clear Cell Renal Cell Carcinoma Treated With Radical Nephrectomy Based on Tumor Stage, Size, Grade and Necrosis: The SSIGN Score," The Journal of Urology, vol. 168, Dec. 2002, pp. 2395-2400.
Freeman et al., "Protect the killer: CTLs need defenses against the tumor", Nature Medicine, vol. 8, No. 8, pp. 787-789, Aug. 2002.
Frigola et al., "Identification of a Soluble Form of B7-H1 That Retains Immunosuppressive Activity and is Associated with Aggressive Renal Cell Carcinoma," Clin Cancer Res, vol. 17, No. 7, 2011, pp. 1915-1923 (Published online Feb. 25, 2011).
Fuerst et al., "Transfer of the inducible lac repressor/operator system from *Escherichia coli* to a vaccinia virus expression vector," Proc. Natl. Acad. Sci. USA, vol. 86, Apr. 1989, pp. 2549-2553.
Fyfe et al., "Results of Treatment of 255 Patients with Metastatic Renal Cell Carcinoma Who Received High-Dose Recombinant Interleukin-2 Therapy," Journal of Clinical Oncology, vol. 13, No. 3, Mar. 1995, pp. 688-696.
GenBank Accession No. AAC51660, dated Sep. 2004, 2 pages.
GenBank Accession No. AK001872.1, "*Homo sapiens* cDNA FLJ11010 fis, clone PLACE1003145," pp. 1-2, (submitted Feb. 16, 2000).
GenBank Accession No. AL162253, "Human DNA sequence from clone RP11-574F11 on chromosome 9 contains the gene for B7-H1 protein (PD-LI), the gene for programmed death ligan 2 (PDL2) (PDCD1L2) and a novel gene," pp. 1-36 (Mar. 24, 2000).
GenBank Accession No. U75285, dated Sep. 2004, 5 pages.
GenBank under Accession No. AAF25807, Jan. 18, 2000, 1 page.
GenBank under Accession No. AAP37283, Jun. 1, 2003, 1 page.
GenBank under Accession No. AF177937, Jan. 18, 2000, 1 page.
GenBank under Accession No. AY280972, Jun. 1, 2003, 1 page.
Gerstmayer et al., "Costimulation of T cell proliferation by a chimeric B7-2 antibody fusion protein specifically targeted to cells expressing the erbB2 proto-oncogene," The Journal of Immunology, vol. 158, 1997, pp. 4584-4590, XP002116142.
Gerstmayer et al., "Costimulation of T-cell proliferation by a chimeric B7-antibody fusion protein," Cancer Immunology Immunotherapy, vol. 45, 1997, pp. 156-158, XP002932422.
Gevaert et al., "Protein identification based on matrix assisted laser desorption/ionization-post source decay-mass spectrometry," Electrophoresis, vol. 22, 2001, pp. 1645-1651.
Ghebeh et al., "The B7-H1 (PD-L1) T Lymphocyte-Inhibitory Molecule is Expressed in Breast Cancer Patients with Infiltrating Ductal Carcinoma: Correlation with Important High-Risk Prognostic Factors," Neoplasia, vol. 8, No. 3, Mar. 2006, pp. 190-198.
Gimmi et al., "B-cell surface antigen B7 provides a costimulatory signal that induces T cells to proliferate and secrete interleukin 2," Proc. Natl. Acad. Sci. USA, vol. 88, Aug. 1991, pp. 6575-6579.
Goodwin et al., "Molecular Cloning and Expression of the Type 1 and Type 2 Murine Receptors for the Tumor Necrosis Factor," Molecular and Cellular Biology, vol. 11, No. 6, Jun. 1991, pp. 3020-3026.

Goodwin et al., "Molecular cloning of a ligand for the inducible T cell gene 4-1BB: a member of an emerging family of cytokines with homology to tumor necrosis factor," Eur. J. Immunol., vol. 23, 1993, pp. 2631-2641.

Green et al., "Activation-induced cell death in T cells," Immunological Reviews, vol. 193, 2003, pp. 70-81.

Green et al., "Antigen-specific human monoclonal antibodies from mice engineered with human Ig heavy and light chain YACs," Nature Genetics, vol. 7, May 1994, pp. 13-21.

Greenwald et al., "The B7 family revisited," Annu. Rev. Immunol., vol. 23, 2005, pp. 515-548 (Published online Jan. 19, 2005).

Guatelli et al., "Isothermal, in vitro amplification of nucleic acids by a multienzyme reaction modeled after retroviral replication," Proc. Natl. Acad. Sci. USA, vol. 87, Mar. 1990, pp. 1874-1878.

Guinn et al., "4-1BBL Cooperates with B7-1 and B7-2 in Converting a B Cell Lymphoma Cell Line into a Long-Lasting Antitumor Vaccine," The Journal of Immunology, vol. 162, 1999, pp. 5003-5010.

Guo et al., "A novel fusion protein of IP10-scFv retains antibody specificity and chemokine function," Biochemical and Biophysical Research Communications, vol. 320, 2004, pp. 506-513 (pp. 506-512 provided).

Haendeler et al., "Nitric Oxide and Apoptosis," Vitamins and Hormones, vol. 57, 1999, pp. 49-77.

Hatzoglou et el., "Hepatic gene transfer in animals using retroviruses containing the promoter from the gene for phosphoenolpyruvate carboxykinase" The Journal of Biological Chemistry, vol. 265, No. 28, Oct. 5, 1990, pp. 17285-17293.

Hawiger et al., "Dendritic cells induce peripheral T cell unresponsiveness under steady state conditions in vivo," J. Exp. Med., vol. 194, No. 6, Sep. 17, 2001, pp. 769-779.

He et al., "Blockade of B7-H1 with sPD-1 Improves Immunity against Murine Hepatocarcinoma," Anticancer Research, vol. 25, 2005, pp. 3309-3313.

He et al., "Identification of a novel splice variant of human PD-L1 mRNA encoding an isoform-lacking Igv-like domain," Acta Pharmacol Sinica, vol. 26, No. 4, Apr. 2005, pp. 462-468.

Hellström et al., "T Cell immunity to Tumor Antigens," Critical Reviews in Immunology, vol. 18, 1998, pp. 1-6.

Henikoff et al., "Amino acid substitution matrices from protein blocks," Proc. Natl. Acad. Sci USA, vol. 89, Nov. 1992, pp. 10915-10919.

Henry et al., "Cloning, structural analysis, and mapping of the B30 and B7 multigenic families to the major histocompatibility complex (MHC) and other chromosomal regions," Immunogenetics, vol. 46, 1997, pp. 383-395.

Hestdal et al., "Characterization and Regulation of RB6-8C5 Antigen Expression on Murine Bone Marrow Cells," The Journal of Immunology, vol. 147, No. 1, Jul. 1, 1991, pp. 22-28.

Hildeman et al., "Activated T cell death in vivo mediated by proapoptotic Bcl-2 family member bim," Immunity, vol. 16, Jun. 2002, pp. 759-767.

Hirano et al., "Blockade of B7-H1 and PD-1 by Monoclonal Antibodies Potentiates Cancer Therapeutic Immunity," Cancer Res, vol. 65, No. 3, Feb. 1, 2005, pp. 1089-1096.

Hiroishi et al., "Interferon-alpha gene therapy in combination with CD80 transduction reduces tumorigenicity and growth of established tumor in poorly immunogenic tumor models," Gene Therapy, vol. 6, 1999, pp. 1988-1994.

Hochman et al., "An active antibody fragment (Fv) composed of the variable portions of heavy and light chains," Biochemistry, vol. 12, No. 6, 1973, pp. 1130-1135.

Hock et al., "Retrovirus-mediated transfer and expression of drug resistance genes in human haematopoietic progenitor cells," Nature, vol. 320, Mar. 20, 1986, pp. 275-277.

Hodi et al., "Re-induction with ipilimumab, gp100 peptide vaccine, or a combination of both from a phase III, randomized, double-blind, multicenter study of previously treated patients with unresectable stage III or IV melanoma," J Clin Oncol, vol. 28, No. 15, (Suppl; abstr 8509), 2010, 2 pages.

Hoffman, "T Cells in the Pathogenesis of Systemic Lupus Erythematosus," Frontiers in Bioscience, vol. 6, Oct. 1, 2001, pp. d1369-d1378.

Hoiseth et al., "Aromatic-dependent Salmonella typhimurium are non-virulent and effective as live vaccines," Nature, vol. 291, May 21, 1981, pp. 238-239.

Hori et al., "B7-H1-Induced Apoptosis as a Mechanism of Immune Privilege of Corneal Allografts," The Journal of Immunology, vol. 177, 2006, pp. 5928-5935.

Huang et al., "The liver eliminates T cells undergoing antigen-triggered apoptosis in vivo," Immunity, vol. 1, Dec. 1994, pp. 741-749.

Huang, "Structural chemistry and therapeutic intervention of protein-protein interactions in immune response, human immunodeficiency virus entry, and apoptosis," Pharmacology & Therapeutics, vol. 86, 2000, pp. 201-215.

Hubbard et al., "Anti-neutrophil-elastase defenses of the lower respiratory tract in $\alpha$1-antitrypsin deficiency directly augmented with an aerosol of $\alpha$1-antitrypsin," Annals of Internal Medicine, vol. 111, No. 3, Aug. 1, 1989, pp. 206-212.

Hunter, "Diabetes in pregnancy," Effective Care in Pregnancy and Childbirth, (Editors: Chalmers et al.), Oxford University Press, 1989, pp. 578-593.

Huse et al., "Generation of a Large Combinatorial Library of the Immunoglobulin Repertoire in Phage Lambda," Science, vol. 246, Dec. 8, 1989, pp. 1275-1281.

Hyrup et al., "Peptide Nucleic Acids (PNA): Synthesis, Properties and Potential Applications", Bioorganic & Medicinal Chemistry, vol. 4, No. 1, 1996, pp. 5-23.

Ichikawa et al., "Role of B7-H1 and B7-H4 molecules in down-regulating effector phase of T-cell immunity: novel cancer escaping mechanisms," Frontiers in Bioscience, vol. 10, 2005, pp. 2856-2860.

IDS submitted in U.S. Appl. No. 10/890,789 concerning certain test data (submitted on Nov. 6, 2007).

Iehle et al., "Differences in steroid 5$\alpha$-reductase iso-enzymes expression between normal and pathological human prostate tissue," Journal of Steroid Biochemistry and Molecular Biology, vol. 68, 1999, pp. 189-195.

Ikemizu et al., "Structure and Dimerization of a Soluble Form of B7-1", Immunity, vol. 12, Jan. 2000, pp. 51-60.

Ikonomidis, "Delivery of a viral antigen to the class I processing and presentation pathway by Listeria monocytogenes," J. Exp. Med., vol. 180, Dec. 1994, pp. 2209-2218.

Inman et al., "PD-L1 (B7-H1) Expression by Urothelial Carcinoma of the Bladder and BCG-Induced Granulomata," Cancer, vol. 109, 2007, pp. 1499-1505 (Published online Mar. 5, 2007).

Inman et al., "Questionable Relevance of $\gamma\sigma$ T Lymphocytes in Renal Cell Carcinoma," The Journal of Immunology, vol. 180, 2008, 3578-3584.

Ishida et al., "Differential expression of PD-L1 and PD-L2, ligands for an inhibitory receptor PD-1, in the cells of lymphohematopoietic tissues", Immunology Letters, vol. 84, 2002, pp. 57-62.

Ishida et al., "Induced expression of PD-1, a novel member of the immunoglobulin gene superfamily, upon programmed cell death," The EMBO Journal, vol. 11, No. 11, 1992, pp. 3887-3895.

Iwai et al., "PD-1 InhibitS Antiviral Immunity at the Effector Phase in the Liver," J. Exp. Med., vol. 198, No. 1, Jul. 7, 2003, pp. 39-50.

Iwai et al., "Involvement of PD-L1 on tumor cells in the escape from host immune system and tumor immunotherapy by PD-L1 blockade," PNAS, vol. 99, No. 19, Sep. 17, 2002, pp. 12293-12297.

Iwai et al., "PD-1 blockade inhibits hematogenous spread of poorly immunogenic tumor cells by enhanced recruitment of effector T cells", International Immunology, vol. 17, No. 2, 2004, pp. 133-144.

Jacobson et al., "Unique site of IgG2a and rheumatoid factor production in MRL/lpr mice," Immunological Reviews, vol. 156, 1997, pp. 103-110.

Japanese Journal of Urology, vol. 95, Mar. 2004, p. 369, OP2-076.

Jeannin et al., "Soluble CD86 is a costimulatory molecule for human T lymphocytes," Immunity, vol. 13, Sep. 2000, pp. 303-312.

Jemal et al., "Cancer Statistics, 2005," CA: A Cancer Journal for Clinicians, vol. 55, 2005, pp. 10-30.

Jerne, "Towards a network theory of the immune system," Ann. Immunol. (Inst. Pasteur.), vol. 125 C, 1974, pp. 373-389.

Johnston et al., "Biolistic Transformation of Animal Tissue," In Vitro Cell.Dev. Biol., vol. 27P, 1991, pp. 11-14.

Jones et al., "Replacing the complementarity-determining regions in a human antibody with those from a mouse," Nature, vol. 321, May 29, 1986, pp. 522-525.

Journal of Japan Surgical Society, vol. 105, Extra Edition, p. 258, SF-060-3 (Mar. 2004).

Kaiser, "First Pass at Cancer Genome Reveals Complex Landscape," Science, vol. 313, Sep. 8, 2006, p. 1370.

Kaleko et al., "Persistent gene expression after retroviral gene transfer into liver cells in vivo," Human Gene Therapy, vol. 2, 1991, pp. 27-32.

Kaliyaperumal et al., "Antigen-Specific Therapy of Murine Lupus Nephritis Using Nucleosomal Peptides: Tolerance Spreading Impairs Pathogenic Function of Autoimmune T and B Cells," The Journal of Immunology, vol. 162, 1999, pp. 5775-5783 (22 pages provided).

Kalled et al., "Anti-CD40 Ligand Antibody Treatment of SNF1 Mice with Established Nephritis: Preservation of Kidney Function," The Journal of Immunology, vol. 160, 1998, pp. 2158-2165 (22 pages provided).

Kanai et al., "Blockade of B7-H1 suppresses the development of chronic intestinal inflammation," The Journal of Immunology, vol. 171, 2003, pp. 4156-4163.

Kaneko et al., "Augmentation of Vα14 NKT cell-mediated cytotoxicity by interleukin 4 in an autocrine mechanism resulting in the development of concanavalin A-induced hepatitis," J. Exp. Med., vol. 191, No. 1, Jan. 3, 2000, pp. 105-114.

Kaufman et al., "A phase I trial of intra lesional RV-B7.1 vaccine in the treatment of malignant melanoma," Human Gene Therapy, vol. 11, May 1, 2000, pp. 1065-1082.

Kawabe et al., "Programmed cell death and extrathymic reduction of Vβ8+ CD4+ T cells in mice tolerant to *Staphylococcus aureus* enterotoxin B," Nature, vol. 349, Jan. 17, 1991, pp. 245-248.

Kelley et al., "Cytokines in the Pathogenesis of Systemic Lupus Erythematosus," Seminars in Nephrology, vol. 19, No. 1, Jan. 1999, pp. 57-66.

Kennerdell et al., "Use of dsRNA-Mediated Genetic Interferende to demonstrate that frizzled and frizzled 2 Act in the Wingless Pathway," Cell, vol. 95, Dec. 23, 1998, pp. 1017-1026.

Kim et al., "State-of-the-Art Review: Therapeutic Potential of 4-1BB (CD137) As a Regulator for Effector CD8+ T Cells," Journal of Hematotherapy & Stem Cell Research, vol. 10, 2001, pp. 441-449.

Kirkin et al., "Melanoma-associated antigens recognized by cytotoxic T lymphocytes," APMIS, vol. 106, 1998, pp. 665-679.

Klippel, "Systemic Lupus Erythematosus: Demographics, Prognosis, and Outcome", J. Rheumatol., vol. 24, Suppl. 48, 1997, pp. 67-71.

Köhler et al., "Continuous cultures of fused cells secreting antibody of predefined specificity," Nature, vol. 256, Aug. 7, 1975, pp. 495-497.

Kohn et al., "Gene therapy for genetic diseases," Cancer Investigation, vol. 7, No, 2, 1989, pp. 179-192.

Konishi et al., "B7-H1 Expression on Non-Small Cell Lung Cancer Cells and Its Relationship with Tumor-Infiltrating Lymphocytes and Their PD-1 Expression," Clinical Cancer Research, vol. 10, Aug. 1, 2004, pp. 5094-5100.

Korkola et al., "Gene expression-based classification of nonseminomatous male germ cell tumors," Oncogene, vol. 24, 2005, pp. 5101-5107 (Published online May 2, 2005).

Kosari et al., "Clear Cell Renal Cell Carcinoma: Gene Expression Analyses Identify a Potentional Signature for Tumor Aggressiveness," Clin Cancer Res, vol. 11, No. 14, Jul. 15, 2005, pp. 5128-5139.

Kozbor et al., "The production of monoclonal antibodies from human lymphocytes," Immunology Today, vol. 4, No. 3, 1983, pp. 72-79.

Krueger et al., "The role of CD95 in the regulation of peripheral T-cell apoptosis," Immunological Reviews, vol. 193, 2003, pp. 58-69.

Krummel et al., "CTLA-4 Engagement Inhibits IL-2 Accumulation and Cell Cycle Progression upon Activation of Resting T Cells," J. Exp. Med., vol. 183, Jun. 1996, pp. 2533-2540.

Kuiper et al., "B7.1 and cytokines Synergy in cancer gene therapy," Cancer Gene Therapy: Past Achievements and Future Challenges, (Editor: Habib), Kluwer Academic/Plenum Publishers, 2000, pp. 381-390.

Kusmartsev et al., "Gr-1+ myeloid cells derived from tumor-bearing mice inhibit primary T cell activation induced through CD3/CD28 costimulation," The Journal of Immunology, vol. 165, 2000, pp. 779-785.

Kwon et al., "4-1BB: Still in the Midst of Darkness," Molecules and Cells, vol. 10, No. 2, 2000, pp. 119-126.

LaBaer et al., "So, You want to Look for Biomarkers (Introduction to the Special Biomarkers Issue)," Journal of Proteome Research, vol. 4, 2005, pp. 1053-1059 (Published online Jun. 30, 2005).

Latchman et al., "PD-L2 is a second ligand for PD-1 and inhibits T cell activation", Nature Immunology, vol. 2, No. 3, Mar. 2001, pp. 261-268.

Lawrence et al., "Phase II trial of ipilimumab monotherapy in melanoma patients with brain metastases," J Clin Oncol., vol. 28, No. 15s (suppl; abstr 8523), 2010, 2 pages.

Lawson et al., "Treatment of murine lupus with cDNA encoding IFN-γR/Fc," J. Clin. Invest., vol. 106, No. 2, 2000, pp. 207-215.

Lazar et al., "Transforming Growth Factor α: Mutation of Aspartic Acid 47 and Leucine 48 Results in Different Biological Activities," Molecular and Cellular Biology, vol. 8, No. 3, Mar. 1988, pp. 1247-1252.

Lee et al., "Increased Vaccine-Specific T Cell Frequency After Peptide-Based Vaccination Correlates with Increased Susceptibility to In Vitro Stimulation But Does Not Lead to Tumor Regression", The Journal of Immunology, vol. 163, 1999, pp. 6292-6300.

Lee et al., "Survivin expression and its clinical significance in pancreatic cancer," BMC Cancer, Oct. 4, 2005, vol. 5, No. 127, 6 pages.

Leibovich et al., "Prediction of Progression After Radical Nephrectomy for Patients with Clear Cell Renal Cell Carcinoma," Cancer, vol. 97, 2003, pp. 1663-1671.

Lenardo et al., "Mature T lymphocyte apoptosis—immune regulation in a dynamic and unpredictable antigenic environment," Annu. Rev. Immunol., vol. 17, 1999, pp. 221-253.

Lenschow et al., "CD28/B7 System of T Cell Costimulation," Annu. Rev. Immunol., vol. 14, 1996, pp. 233-258.

Levitt, "Accurate Modeling of Protein Conformation by Automatic Segment Matching," J. Mol. Biol., vol. 226, 1992, pp. 507-533.

Lewinski et al., "Retroviral DNA integration: viral and cellular determinants of target-site selection," PLoS Pathogens, vol. 2, No. 6, e60, Jun. 23, 2006, pp. 0611-0621, XP002510754.

Lewis, "PCR's Competitors Are Alive and Well and Moving Rapidly Towards Commercialization," Genetic Engineering News, Jun. 1, 1992, vol. 12, No. 9, 3 pages.

Li et al., "Fas-mediated apoptosis causes elimination of virus-specific cytotoxic T cells in the virus-infected liver," The Journal of Immunology, vol. 166, 2001, pp. 3035-3041.

Liang et al., "Autoantibody Responses and Pathology Regulated by B7-1 and B7-2 Costimulation in MRL/lpr Lupus," The Journal of Immunology, vol. 165, 2000, pp. 3436-3443 (17 pages provided).

Linsley et al., "Binding of the B cells activation antigen B7 to CD28 costimulates T cell proliferation and interleukin 2 mRNA accumulation," J. Exp. Med., vol. 173, Mar. 1991, pp. 721-730.

Linsley et al., "Extending the B7 (CD80) gene family," Protein Science, vol. 3, 1994, pp. 1341-1343.

Linsley et al., "T-cell antigen CD28 mediates adhesion with B cells by interacting with activation antigen B7/BB-1," Proc. Nat. Acad. Sci. USA, vol. 87, Jul. 1990, pp. 5031-5035.

Liu et al., "B7-H1 on myeloid-derived suppressor cells in immune suppression by a mouse model of ovarian cancer," Clinical Immunology, vol. 129, 2008, pp. 471-481 (Published online Sep. 14, 2008).

Liu et al., B7DC/PDL2 promotes tumor immunity by a PD-1-independent mechanism, J. Exp. Med., vol. 197, No. 12, Jun. 16, 2003, pp. 1721-1730.

Lonberg et al., "Antigen specific human antibodies from mice comprising four distinct genetic modifications," Nature, vol. 368, Apr. 28, 1994, pp. 856-859.

Losman et al., "Baboon anti-idiotype antibodies mimic a carcinoembryonic antigen epitope," Int. J. Cancer, vol. 46, 1990, pp. 310-314.

Lu et al., "EGF-IL-18 fusion protein as a potential anti-tumor reagent by induction of immune response and apoptosis in cancer cells," Cancer Letters, vol. 260, 2008, pp. 187-197.

Luettig et al., "Naive and memory T lymphocytes migrate in comparable numbers through normal rat liver: activated T cells accumulate in the periportal field," The Journal of Immunology, vol. 163, 1999, pp. 4300-4307.

Ma et al., "The Role of PD-1 Ligand in Immune Evasion by Breast Cancer," Dana-Farber Cancer Institute, Annual Summary Report, May 1, 2005, pp. 1-13.

Mackenzie, "New therapeutics that treat rheumatoid arthritis by blocking T-cell activation," Drug Discovery Today, vol. 11, Nos. 19/20, Oct. 2006, pp. 952-956.

Mahotka et al., "Distinct in vivo expression patterns of survivin splice variants in renal cell carcinomas," Int. J. Cancer, vol. 100, 2002, pp. 30-36.

Mann et al., "Construction of a retrovirus packaging mutant and its use to produce helper-free defective retrovirus," Cell, vol. 33, May 1983, pp. 153-159.

Martin at al. "Combination gene therapy with CD86 and the MHC Class II transactivator in the control of lung tumor growth," The Journal of Immunology, vol. 162, 1999, pp. 6663-6670.

Mathiowitz et al., "Morphology of polyanhydride microsphere delivery systems," Scanning Microscopy, vol. 4, No. 2, 1990, pp. 329-340.

Mathiowitz et al., "Polyanhydride microspheres as drug carriers. I. Hot-melt microencapsulation," Journal of Controlled Release, vol. 5, 1987, pp. 13-22.

Mathiowitz et al., "Polyanhydride microspheres. IV. Morphology and characterization of systems made by spray drying," Journal of Applied Polymer Science, vol. 45, 1992, pp. 125-134.

Mathiowitz at al., "Novel microcapsules for delivery systems," Reactive Polymers, vol. 6, 1987, pp. 275-283.

Mathiowitz et al., "Polyanhydride microspheres as drug carriers. II. Microencapsulation by solvent removal," Journal of Applied Polymer Science, vol. 35, 1988, pp. 755-774.

Mayo Clinic, "Mayo Clinic Discovers Potential Marker for Aggressive Kidney Cancer," Science Daily, Dec. 9, 2004, 3 pages URL: http://www.sciencedaily.com/releases/2004/11/041130200858.htm.

Mazanet et al., "B7-H1 Is Expressed by Human Endothelial Cells and Suppresses T Cell Cytokine Synthesis," The Journal of Immunology, vol. 169, 2002, pp. 3581-3588.

McLachin et al., "Retroviral-mediated gene transfer," Progress in Nucleic Acid Research and Molecular Biology, (Editors: Cohn et al.), vol. 38, 1990, pp. 91-135.

Mehal et al., "Antigen presentation by liver cells controls intrahepatic T cell trapping, whereas bone marrow-derived cells preferentially promote intrahepatic T cell apoptosis," The Journal of Immunology, vol. 167, 2001, pp. 667-673.

Mehal et al., "TCR ligation on CD8+ T cells creates double-negative cells in vivo," The Journal of Immunology, vol. 161, 1998, pp. 1686-1693.

Melero et al., "Amplification of tumor immunity by gene transfer of the co-stimulatory 4-1BB ligand: synergy with the CD28 co-stimulatory pathway," Eur. J. Immunol., vol. 28, 1998, pp. 1116-1121, XP000914703.

Melero et al., "Monoclonal antibodies against the 4-1BB T-cell activation molecule eradicate established tumors," Nature Medicine, vol. 3, No. 6, Jun. 1997, pp. 682-685, XP002104261.

Melero et al., "NK1.1 Cells Express 4-1BB (CDw137) Costimulatory Molecule and Are Required for Tumor Immunity Elicited by Anti-4-1BB Monoclonal Antibodies," Cellular Immunology, vol. 190, Article No. CI981396, 1998, pp. 167-172.

Melero et al., "Palettes of Vaccines and Immunostimulatory Monoclonal Antibodies for Combination", Clin. Cancer. Res., vol. 15, No. 5, Mar. 1, 2009, pp. 1507-1509.

Melief et al., "Strategies for Immunotherapy of Cancer", Advances in Immunology, vol. 75, 2000, pp. 235-282, XP001027072.

Mellman, "Where Next for Cancer Immunotherapy?," The Scientist, vol. 20, Issue 1, 2006, pp. 47-56.

Merrill et al., "The role of biomarkers in the assessment of lupus", Best Practice & Research Clinical Rheumatology, vol. 19, No. 5, 2005, pp. 709-726.

Merrill, "Emergence of targeted immune therapies for systemic lupus," Expert Opin. Emerging Drugs, vol. 10, No. 1, 2005, pp. 53-65.

Miller et al., "Gene transfer by retrovirus vectors occurs only in cells that are actively replicating at the time of infection," Molecular and Cellular Biology, vol. 10, No. 8, Aug. 1990, pp. 4239-4242.

Miller et al., "Generation of helper-free amphotropic retroviruses that transduce a dominant-acting, methotrexate-resistant dihydrofolate reductase gene," Molecular and Cellular Biology, vol. 5, No. 3, Mar. 1985, pp. 431-437.

Miller et al., "Redesign of retrovirus packaging cell lines to avoid recombination leading to helper virus production," Molecular and Cellular Biology, vol. 6, No. 8, Aug. 1986, pp. 2895-2902.

Miller, "Human gene therapy comes of age," Nature, vol. 357, Jun. 11, 1992, pp. 455-460.

Misquitta et al., "Targeted disruption of gene function in *Drosophila* by RNA interference (RNA-i): A role for nautilus in embryonic somatic muscle formation," Proc. Natl. Acad. Sci. USA, vol. 96, Feb. 1999, pp. 1451-1456.

Mizuhara et al., "T cell activation-associated hepatic injury: mediation by tumor necrosis factors and protection by interleukin 6," J. Exp. Med., vol. 179, May 1994, pp. 1529-1537.

Mohan et al., "Interaction Between CD40 and Its Ligand gp39 in the Development of Murine Lupus Nephritis," The Journal of Immunology, vol. 154, 1995, pp. 1470-1480.

Montesano et al., "Genetic Alterations in Esophageal Cancer and Their Relevance to Etiology and Pathogenesis: A Review," Int. J. Cancer (Pred. Oncol.), vol. 69, 1996, pp. 225-235.

Morse et al., "Abnormalities Induced by the Mutant Gene Ipr: Expansion of a Unique Lymphocyte Subset," The Journal of Immunology, vol. 129, No. 6, Dec. 1982, pp. 2612-2615.

Moss et al., "Use of vaccinia virus as an infectious molecular cloning and expression vector," Gene Amplification and Analysis, (Editors: Papas et al.), vol. 3, Chapter 10, 1983, pp. 201-213.

Moss, "Poxvirus expression vectors," Current Topics in Microbiology and Immunology, vol. 158, 1992, pp. 25-38.

Moss, "Poxvirus vectors: cytoplasmic expression of transferred genes," Current Opinion in Genetics and Development, vol. 3, 1993, pp. 86-90.

Moss, "Vaccinia virus vectors," Vaccines: New Approaches to Immunological Problems, (Editor: Ellis), Butterworth-Heinemann, Chapter 15, 1992, pp. 345-362.

Moss, "Vaccinia virus: a tool for research and vaccine development," Science, vol. 252, Jun. 21, 1991, pp. 1662-1667.

Motzer et al., "Renal-Cell Carcinoma," New England Journal of Medicine, vol. 335, No. 12, Sep. 19, 1996, pp. 865-875.

MPSRCH search results (2008) us-11-245-713.1.rai, result 11, Sequence 4, U.S. Appl. No. 10/068,215, pp. 1-2.

Nabel et al., "Recombinant gene expression in vivo within endothelial cells of the arterial wall," Science, vol. 244, Jun. 16, 1989, pp. 1342-1344.

Nechiporuk et al., "The mouse SCA2 gene: cDNA sequence, alternative splicing and protein expression," Human Molecular Genetics, vol. 7, No. 8, 1998, pp. 1301-1309.

Needleman et al., "A general method applicable to the Search for similarities in the amino acid sequence of two proteins," J. Mol. Biol., vol. 48, 1970, pp. 443-453.

Nelson et al., "Tumor progression despite efficient tumor antigen cross-presentation and effective "arming" of tumor antigen-specific CTL," Journal of Immunology, vol. 166, 2001, pp. 5557-5566.

Neves et al., "Surgical Treatment of Renal Cancer with Vena Cava Extension," British Journal of Urology, vol. 59, 1987, pp. 390-395.

Newmark et al., "Preparation and properties of adducts of streptokinase and streptokinase-plasmin complex with polyethylene glycol and pluronic Polyol F38," Journal of Applied Biochemistry, vol. 4, 1982, pp. 185-189.

Nicolau et al., "In vivo expression of rat insulin after intravenous administration of the liposome-entrapped gene for rat insulin I," Proc. Natl. Acad. Sci. USA, vol. 80, Feb. 1983, pp. 1068-1072.

Nielsen et al., "Melanoma vaccines: the paradox of T cell activation without clinical response," Cancer Chemother. Pharmacol., vol. 46 (Suppl.), 2000, pp. S62-S66.

Nielsen et al., "Peptide nucleic acid (PNA). A DNA mimic with a peptide backbone," Bioconjugate Chem., vol. 5, 1994, pp. 3-7.

Nielsen et al., "Sequence-selective recognition of DNA by strand displacement with a thymine-substituted polyamide," Science, vol. 254, Dec. 6, 1991, pp. 1497-1500.

Nishimura et al., "Autoimmune Dilated Cardiomyopathy in PD-1 Receptor-Deficient Mice", Science, vol. 291, Jan. 12, 2001, pp. 319-322.

Nishimura et al., "Development of Lupus-like Autoimmune Diseases by Disruption of the PD-1 Gene Encoding an ITIM Motif-Carrying Immunoreceptor," Immunity, vol. 11, Aug. 1999, pp. 141-151.

Nishimura et al., "Immunological studies on PD-1-deficient mice: implication of PD-1 as a negative regulator for B cell responses," International Immunology, vol. 10, No. 10, 1998, pp. 1563-1572.

Nisonoff et al., "Separation of univalent fragments from the bivalent rabbit antibody molecule by reduction of disulfide bonds," Archives of Biochemistry and Biophysics, vol. 89, 1960, pp. 230-244.

Ohigashi et al., "Clinical Significance of Programmed Death-1 Ligand-1 and Programmed Death-1 Ligand-2 Expression in Human Esophageal Cancer," Clin Cancer Res, vol. 11, No. 8, Apr. 15, 2005, pp. 2947-2953.

Okazaki et al., "PD-1 and PD-1 ligands: from discovery to clinical application," International Immunology, vol. 19, No. 7, 2007, pp. 813-824.

Okudaira et al., "Blockade of B7-H1 or B7-DC induces an anti-tumor effect in a mouse pancreatic cancer model," International Journal of Oncology, vol. 35, No. 4, 2009, pp. 741-749.

Orlandi et al., "Cloning immunoglobulin variable domains for expression by the polymerase chain reaction," Proc. Natl. Acad. Sci. USA, vol. 86, May 1989, pp. 3833-3837.

Ostrov et al., "Structure of Murine CTLA-4 and Its Role in Modulating T Cell Responsiveness," Science, vol. 290, Oct. 27, 2000, pp. 816-819.

Ozkaynak et al., "Programmed death-1 targeting can promote allograft survival," The Journal of Immunology, vol. 169, 2002, pp. 6546-6553, XP002980100.

Pantuck et al., "The Changing Natural History of Renal Cell Carcinoma," The Journal of Urology, vol. 166, Nov. 2001, pp. 1611-1623.

Pardoll, "Spinning molecular immunology into successful immunotherapy," Nature Reviews I Immunology, vol. 2, Apr. 2002, pp. 227-238.

Parker et al., "Potential Utility of Uroplakin III, Thrombomodulin, High Molecular Weight Cytokeratin, and Cytokeratin 20 in Noninvasive, Invasive, and Metastatic Urothelial (Transitional Cell) Carcinoma," Am. J. Surg. Pathol., vol. 27, No. 1, 2003, pp. 1-3 and 5-9.

Peach et al., "Both extracellular immunoglobin-like domains of CD80 contain residues critical for binding T cell surface receptors CTLA-4 and CD28," The Journal of Biological Chemistry, vol. 270, No. 36, Sep. 8, 1995, pp. 21181-21187.

Peghini et al., "Immunophaenotyping in the diagnosis of lymphoma," Praxis, vol. 93, No. 41, Oct. 6, 2004, 1687-1692, Abstract only provided.

Penix et al., "Two Essential Regulatory Elements in the Human Interferon γ Promoter Confer Activation Specific Expression in T Cells," The Journal of Expirimental Medicine, vol. 178, Nov. 1993, pp. 1483-1496.

Perriman et al., "Effective ribozyme delivery in plant cells," Proc. Natl. Acad. Sci. USA, vol. 92, Jun. 1995, pp. 6175-6179.

Petroff et al., "B7 family molecules: Novel immunomodulators at the maternal-fetal interface," Placenta, vol. 23, Supplement A, Trophoblast Research 16, 2002, pp. S95-S101.

Piccini, "Vaccinia: virus, vector, vaccine," Advances in Virus Research, (Editors: Maramorosch et al.), vol. 34, 1988, pp. 43-64.

Plückthun et al., "Expression of functional antibody Fv and Fab fragments in *Escherichia coli*," Methods in Enzymology, vol. 178, 1989, pp. 497-515.

Poirier et al., "Protective immunity evoked by oral administration of attenuated aroA *Salmonella typhimurium* expressing cloned streptococcal M protein," Journal of Experimental Medicine, vol. 168, Jul. 1988, pp. 25-32.

Pollok et al., "4-1BB T-cell antigen binds to mature B cells and macrophages, and costimulates anti-μ-primed splenic B cells," Eur. J. Immunol., vol. 24, 1994, pp. 367-374.

Pollok et al., "Inducible T Cell Antigen 4-1BB," The Journal of Immunology, vol. 150, No. 3, Feb. 1, 1993, pp. 771-781.

Ponder et al., "Tertiary Templates for Proteins: Use of Packing Criteria in the Enumeration of Allowed Sequences for Different Structural Classes," J. Mol. Biol., vol. 193, 1987, pp. 775-791.

Porter, "The hydrolysis of rabbit γ-globulin and antibodies with crystalline papain," Biochem. J., vol. 73, 1959, pp. 119-126.

Prasad et al., "B7S1, a novel B7 family member that negatively regulates T cell activation," Immunity, vol. 18, Jun. 2003, pp. 863-873.

Prévost-Blondel et al., "Tumor-infiltrating lymphocytes exhibiting high ex vivo cytolytic activity fail to prevent murine melanoma tumor growth in vivo," The Journal of Immunology, vol. 161, 1998, pp. 2187-2194.

Radhakrishnan et al., "Dendritic Cells activated by cross-linking B7-DC (PD-L2) block inflammatory airway disease," J Allergy Clin Immunol, vol. 116, No. 3, 2005, pp. 668-674 (Published online Jun. 17, 2005).

Rajewsky et al., "Genetics, expression, and function of idiotypes," Ann. Rev. Immunol., vol. 1, 1983, pp. 569-607.

Rathmell et al., "The Central Effectors of Cell Death in the Immune System," Annu. Rev. Immunol., vol. 17, 1999, pp. 781-828.

Razi-Wolf, "Expression and function of the murine B7 antigen, the major costimulatory molecule expressed by peritoneal exudate cells," Proc. Nat. Acad. Sci. USA, vol. 89, May 1992, pp. 4210-4214.

Renauld et al., "Expression cloning of the murine and human interleukin 9 receptor cDNAs," Proc. Natl. Acad. Sci. USA, vol. 89, Jun. 1992, pp. 5690-5694.

Riechmann et al., "Reshaping human antibodies for therapy," Nature, vol. 332, Mar. 24, 1988, pp. 323-327.

Ritz et al., "Bioassay Analysis using R," Journal of Statistic Software, vol. 12, Issue 5, Jan. 2005, pp. 1-22.

Rivoltini et al., "Immunity to cancer: attack and escape in T lymphocyte-tumor cell interaction," Immunological Reviews, vol. 188, 2002, pp. 97-113.

Robison-Cox, "Multiple estimation of concentrations in immunoassay using logistic models," Journal of Immunological Methods, vol. 186, 1995, pp. 79-88.

Romano et al., "Quelling: transient inactivation of gene expression in *Neurospora crassa* by transformation with homologous sequences," Molecular Microbiology, vol. 6, No. 22, 1992, pp. 3343-3353.

Romero et al., "Ex vivo staining of metastatic lymph nodes by class I major histocompatibility complex tetramers reveals high numbers of antigen-experienced tumor-specific cytolytic T lymphocytes," J. Exp. Med., vol. 188, No. 9, Nov. 2, 1998, pp. 1641-1650.

Rosenberg, "Progress in human tumor immunology and immunotherapy," Nature, vol. 411, May 17, 2001, pp. 380-384.

Rosenfeld et al., "Adenovirus-mediated transfer of a recombinant αI-antitrypsin gene to the lung epithelium in vivo," Science, vol. 252, Apr. 19, 1991, pp. 431-433.

Rousseaux et al, "Optimal conditions for the preparation of proteolytic fragments from monoclonal IgG of different rat IgG subclasses," Methods in Enzymology, vol. 121, 1986, pp. 663-669.

Sadoff et al., "Oral *Salmonella typhimurium* vaccine expressing circumsporozoite protein protects against malaria," Science, vol. 240, Apr. 15, 1988, pp. 336-338.

Salama et al., "Critical role of the programmed death-1 (PD-1) pathway in regulation of experimental autoimmune encephalomyelitis," J. Exp. Med., vol. 198, No. 1, Jul. 7, 2003, pp. 71-78.

Salib et al "Utilization of sodium alginate in drug microencapsulation," Pharmazeutische Industrie, 1978, vol. 40, No. 11A, pp. 1230-1234.

Salih et al., "The role of leukemia-derived B7-H1 (PD-L1) in tumor-T-cell interactions in humans," Experimental Hematology, 2006, vol. 34, pp. 888-894.

Salih et al., "4-1BB ligand—just another costimulating molecule?" International Journal of Clinical Pharmacology and Therapeutics, vol. 40, No. 8, 2002, pp. 348-353.

Salomon et al., "Complexities of CD28/B7: CTLA-4 costimulatory pathway in autoimmunity and transplantation," Annu. Rev. Immunol., vol. 19, 2001, pp. 225-252.

Samuski et al., "Targeted integration of adeno-associated virus (AAV) into human chromosome 19," The EMBO Journal, vol. 10, No. 12, 1991, pp. 3941-3950.

Sandhu, "Protein Engineering of Antibodies," Critical Reviews in Biotechnology, vol. 12, No. 5/6, 1992, pp. 437-462.

Sanni et al., "Evolution of aminoacyl-tRNA synthetase quaternary structure and activity: *Saccharomyces cerevisiae* mitochondrial phenylalanyl-tRNA synthetase," Proc. Natl. Acad. Sci. USA, vol. 88, Oct. 1991, pp. 8387-8391.

Sawhney et al., "Bioerodible hydrogels based on photopolymerized poly(ethylene glycol)-copoly($\alpha$-hydroxy acid) diacrylate macromers," Macromolecules, vol. 26, No. 4, 1993, pp. 581-587.

Schafer et al., "Induction of a cellular immune response to a foreign antigen by a recombinant Listeria monocytogenes vaccine," J. Immunol., vol. 149, No. 1, Jul. 1, 1992, pp. 53-59.

Schmid et al., "Expression of AMPA Receptor Subunit Flip/Flop Splice Variants in the Rat Auditory Brainstem and Inferior Colliculus," J. Comparative Neurology, vol. 430 No. 2, 2001, pp. 160-171.

Schwartz et al., "Structural Basis for Co-stimulation by the Human CTLA-4/B7-2 Complex," Nature, vol. 410, Mar. 29, 2001, pp. 604-608.

Schwartz et al., "Structural Mechanisms of Costimulation," Nature Immunology, vol. 3, No. 5, May 2002, pp. 427-434.

Schwartz, "Costimulation of T Lymphocytes: The Role of CTLA-4, and B7/BB1 in Interleukin-2 Production and Immunotherapy," Cell, vol. 71, Dec. 24, 1992, pp. 1065-1068.

Selenko-Gebauer et al., "B7-H1 (Programmed Death-1 Ligand) on Dendritic Cells is Involved in the Induction and Maintenance of T Cell Anergy," J. Immunol., vol. 170, 2003, pp. 3637-3644.

Shaknovich et al., "The Promyelocytic Leukemia Zinc Finger Protein Affects Myeloid Cell Growth, Differentiation, and Apoptosis," Molecular and Cellular Biology, vol. 18, No. 9, Sep. 1998, pp. 5533-5545.

Sharon et al., "Preparation of Fv fragment from the mouse myeloma XRPC-25 immunoglobulin possessing antidinitrophenyl activity," Biochemistry, vol. 15, No. 7, 1976, pp. 1591-1594.

Sheather, "Density Estimation," Statistical Science, vol. 19, No. 4, 2004, pp. 588-597.

Shin et al., "Cooperative B7-I/2 (CD80/CD86) and B7-DC Costimulation of CD4+ T Cells Independent of the PD-1 Receptor," J. Exp. Med., vol. 198, No. 1, Jul. 7, 2003, pp. 31-38.

Sica et al., "B7-H4, a Molecule of the B7 Family, Negatively Regulates T Cell Immunity," Immunity, vol. 18, Jun. 2003, pp. 849-861.

Sica et al., "Biochemical and Immunological Characteristics of 4-1BB (CD137) Receptor and Ligand and Potential Applications in Cancer Therapy," Archivum Immunologiae et Therapiae Experimentalis, vol. 47, 1999, pp. 275-279.

Siddiqui et al., "Tumor Infiltrating Foxp3—CD4+CD25+ T Cells Predict Poor Survival in Renal Cell Carcinoma," Clin. Cancer Res., vol. 13, No. 7, Apr. 1, 2007, pp. 2075-2081.

Silverman, "Targeting of B cells in SLE: Rationale and Therapeutic Opportunities", Bulletin of the NYU Hospital for Joint Diseases, vol. 64, Nos. 1 and 2, 2006, pp. 51-56.

Simon et al., "B7-H4 is a Novel Membrane-Bound Protein and a Candidate Serum and Tissue Biomarker for Ovarian Cancer," Cancer Res., vol. 66, No. 3, Feb. 1, 2006, pp. 1570-1575.

Singer et al., "Optimal Humanization of 1B4, an Anti-CD18 Murine Monoclonal Antibody, is Achieved by Correct Choice of Human V-Region Framework Sequences," The Journal of Immunology, vol. 150, Apr. 1, 1993, pp. 2844-2857.

Skerra et al., "Assembly of a Functional Immunoglobulin Fv Fragment in *Escherichia coli*," Science, vol. 240, May 20, 1988, pp. 1038-1041.

Smith et al., "Pulmonary Deposition and Clearance of Aerosolized Alpha-1-Proteinase Inhibitor Administered to Dogs and to Sheep," J. Clin. Invest., vol. 84, Oct. 1989, pp. 1145-1154.

Smith, "Cancer and the Immune System," Clinical Immunology, vol. 41, No. 4, Aug. 1994, pp. 841-849.

Sneller et al., "A Novel Lymphoproliferative/Autoimmune Syndrome Resembling Murine Ipr/gld Disease," J. Clin. Invest., vol. 90, Aug. 1992, pp. 334-341.

Solares et al., "Autoimmune sensorineural hearing loss: an immunologic perspective," Journal of Neuroimmunology, vol. 138, 2003, pp. 1-7.

Sorge et al., "Amphotropic Retrovirus Vector System for Human Cell Gene Transfer," Molecular and Cellular Biology, vol. 4, No. 9, Sep. 1984, pp. 1730-1737.

Soriano et al., "Targeted and nontargeted liposomes for in vivo transfer to rat liver cells of a plasmid containing the preproinsulin I gene," Proc. Natl. Acad. Sci. USA, vol. 7128-7131.

Stammers et al., "BTL-II: A polymorphic locus with homology to the butyrophilin gene family, located at the border of the major histocompatibility complex class II and class III regions in human and mouse," Immunogenetics, vol. 51, 2000, pp. 373-382.

Stamper et al., "Crystal structure of the B7-1/CTLA-4 complex that inhibits human immune responses," Nature, vol. 410, Mar. 29, 2001, pp. 308-311.

Stanton et al., "Epidermal growth factor receptor expression by human squamous cell carcinomas of the head and neck, cell lines and xenografts," Br. J. Cancer, vol. 70, 1994, pp. 427-433.

Steinman et al., "Immunotherapy: Bewitched, Bothered, and Bewildered No More," Science, vol. 305, Jul. 9, 2004, pp. 197-200.

Stites et al., "Medical Immunology," 9th Ed., Appleton & Lange, Stamford, Connecticut, 1997, pp. 123 and 635.

Strome et al., "B7-H1 Blockade Augments Adoptive T-Cell Immunotheapy for Squamous Cell Carcinoma1," Cancer Research, vol. 63, Oct. 1, 2003, pp. 6501-6505.

Subudhi et al., "Local rejection of B7-H1 promotes organ-specific autoimmunity and transplant rejection," J. Clin. Invest., vol. 113, No. 5, Mar. 2004, pp. 694-700.

Suda et al., "Why do defects in the Fas-Fas ligand system cause autoimmunity?", J. Allergy Clin. Immunol., vol. 100, 1997, pp. S97-S101.

Summerton et al., "Morpholino Antisense Oligomers: Design, Preparation, and Properties," Antisense & Nucleic Acid Drug Development, vol. 7, 1997, pp. 187-195.

Sun et al., "Administration of Agonistic Anti-4-1BB Monoclonal Antibody Leads to the Amelioration of Experimental Autoimmune Encephalomyelitis," The Journal of Immunology, vol. 168, 2002, pp. 1457-1465.

Sun et al., "Costimulatory molecule-targeted antibody therapy of a spontaneous autoimmune disease," Nature Medicine, vol. 8, No. 12, Dec. 2002 (Published online Nov. 11, 2002), pp. 1405-1413.

Sun et al., "Signaling of 4-1BB Leads to Amelioration of Experimental Autoimmune Encephalomyelitis," FASEB J., 2001, 5:A1210, Abstract 950.9.

Sutter et al., "Nonreplicating vaccina vector efficiently expresses recombinant genes," Proc. Natl. Acad. Sci. USA, vol. 89, Nov. 1992, pp. 10847-10851.

Suzuki et al., "T cell-Specific Loss of Pten Leads to Defects in Central and Peripheral Tolerance," Immunity, vol. 14, May 2001, pp. 523-534.

Suzuki et al., "The dual functions of Fas ligand in the regulation of peripheral CD8+ and CD4+ T cells," Proc. Natl. Acad. Sci. USA, vol. 97, No. 4, Feb. 15, 2000, pp. 1707-1712.

Takahashi et al., "Cutting Edge: 4-1BB is a Bona Fide CD8 T Cell Survival Signal," The Journal of Immunology, vol. 162, No. 9, 1999, pp. 5037-5040.

Takeda et al., "Critical contribution of liver natural killer T cells to a murine model of hepatitis," Proc. Natl. Acad. Sci. USA, vol. 97, No. 10, May 9, 2000, pp. 5498-5503.

Tamura et al., "B7-H1 costimulation preferentially enhances CD28-independent T-helper cell function," Blood, vol. 97, No. 6, Mar. 15, 2001, pp. 1809-1816.

Taylor et al., "Human immunoglobulin transgenes undergo rearrangement, somatic mutation and class switching in mice that lack endogenous IgM," Int. Immunol., vol. 6, No. 4, 1994, pp. 579-591.

Tazi-Ahnini et al., "Cloning, localization, and structure of new members of the butyrophilin gene family in the juxta-telomeric region of the major histocompatibility complex," Immunogenetics, vol. 47, 1997, pp. 55-63.

Temin, "Safety Considerations in Somatic Gene Therapy of Human Disease with Retrovirus Vectors," Human Gene Therapy, vol. 1, 1990, pp. 111-123.

Templeton et al., "Improved DNA: liposome complexes for increased systemic delivery and gene expression," Nature Biotechnology, vol. 15, Jul. 1997, pp. 647-652.

Theofilopoulos et al., "Etiopathogenesis of Murine SLE," Immunological Rev., vol. 55, 1981, pp. 179-216.

Theofilopoulos et al., "Tumour necrosis factor and other cytokines in murine lupus," Ann. Rheum. Dis., vol. 58, Suppl. 1, 1999, pp. 149-155.

Therneau et al., "Modeling Survival Data, Extending the Cox Model," Ed. 1, Springer-Verlag, Ann Arbor, 2000, two cover pages.

Thompson et al., "cis-Acting Sequences Required for Inducible Interleukin-2 Enhancer Function Bind a Novel Ets-Related Protein, Elf-1," Molecular and Cellular Biology, vol. 12, No. 3, Mar. 1992, pp. 1043-1053.

Thompson et al., "Tumor B7-H1 is Associated with Poor Prognosis in Renal Cell Carcinoma Patients with Long-Term Follow-up," Cancer Res., vol. 66, No. 7, Apr. 1, 2006, pp. 3381-3385.

Thompson et al., "B7-H1 Glycoprotein Blockade: A Novel Strategy to Enhance Immunotherapy in Patients With Renal Cell Carcinoma," Urology, vol. 66, Suppl 5A, 2005, pp. 10-14.

Thompson et al., "Costimulatory B7-H1 in renal cell carcinoma patients: Indicator of tumor aggressiveness and potential therapeutic target," Proc. Natl. Acad. Sci. USA, vol. 101, No. 49, Dec. 7, 2004, pp. 17174-17179.

Thompson et al., "Costimulatory Molecule B7-H1 in Primary and Metastatic Clear Cell Renal Cell Carcinoma," Cancer, vol. 104, 2005, pp. 2084-2091.

Thompson et al., "Implications of B7-H1 Expression in Clear Cell Carcinoma of the Kidney for Prognostication and Therapy," Clin. Cancer Res., vol. 13, 2 Suppl., Jan. 15, 2007, pp. 709s-715s.

Tiegs et al., "A T cell-dependent Experimental Liver Injury in Mice Inducible by Concanavalin A," J. Clin. Invest., vol. 90, 1992, pp. 196-203.

Titomirov et al., "In vivo electroporation and stable transformation of skin cells of newborn mice by plasmid DNA," Biochimica et Biophysica Acta, vol. 1088, 1991, pp. 131-134.

Todd et al., "Transcription of the Interleukin 4 Gene Is Regulated by Multiple Promoter Elements," J. Exp. Med., vol. 177, Jun. 1993, pp. 1663-1674.

Townsend et al., "Tumor Rejection After Direct Costimulation of CD8+ T Cells by B7-Transfected Melanoma Cells," Science, vol. 259, Jan. 15, 1993, pp. 368-370.

Trabattoni et al., "B7-H1 is up-regulated in HIV infection and is a novel surrogate marker of disease progression," Blood, vol. 101, No. 7, Apr. 1, 2003, pp. 2514-2520.

Tringler et al., "B7-H4 Is Highly Expressed in Ductal and Lobular Breast Cancer," Clinical Cancer Research, vol. 11, Mar. 1, 2005, pp. 1842-1848.

Tseng et al., "B7-DC, a New Dendritic Cell Molecule with Potent Costimulatory Properties for T Cells," J. Exp. Med., vol. 193, No. 7, Apr. 2, 2001, pp. 839-845.

Ueda et al., "Sequence-specific DNA damage induced by reduced mitomycin C and 7-N-(p-hydroxyphenyl)mitomycin) C," Nucleic Acids Res., vol. 12, No. 17, 1984, pp. 6673-6683.

Uhlig et al., "Is rheumatoid arthritis disappearing?", Annals of the Rheumatic Diseases, vol. 64, 2005, pp. 7-10.

Verhoeyen et al., "Reshaping Human Antibodies: Grafting an Antilysozyme Activity," Science, vol. 239, 1988, pp. 1534-1536.

Vinay et al., "Role of 4-1BB in immune responses," Seminars in Immunology, vol. 10, No. 6, 1998, pp. 481-489.

Wahl et al., "Improved Radioimaging and Tumor Localization with Monoclonal F(ab')2," J. Nucl. Med., vol. 24, 1983, pp. 316-325.

Walunas et al., "CTLA-4 Ligation Blocks CD28-dependent T Cell Activation," J. Exp. Med., vol. 183, Jun. 1996, pp. 2541-2550.

Wang et al., "Costimulation of T cells by B7-H2, a B7-like molecule that binds ICOS," Blood, vol. 96, No. 8, Oct. 15, 2000, pp. 2808-2813.

Wang et al., "Ligand Binding Sites of Inducible Costimulator and High Avidity Mutants with Improved Function," J. Exp. Med., vol. 195, No. 8, Apr. 15, 2002, pp. 1033-1041.

Wang et al., "Molecular Modeling and Functional Mapping of B7-H1 and B7-DC Uncouple Costimulatory Function from PD-1 Interaction," J. Exp. Med., vol. 197, No. 9, May 5, 2003, pp. 1083-1091.

Wang et al., "pH-sensitive immunoliposomes mediate target-cell-specific delivery and controlled expression of a foreign gene in mouse," Proc. Natl. Acad. Sci. USA, vol. 84, Nov. 1987, pp. 7851-7855.

Weiss, "Hot Prospect for New Gene Amplifier: Ligase chain reaction, a combination DNA amplifier and genetic screen, could do for DNA diagnostics what PCR has done for basic molecular biology," Science, vol. 254, Nov. 1991, pp. 1292-1293.

Wick et al., "The hepatic Immune System," Critical Reviews in Immunology, vol. 22, No. 1, 2002, pp. 47-103.

Wilcox et al., "B7-H1 (PD-L1, CD274) suppresses host immunity in T-cell lymphoproliferative disorders," Blood, vol. 114, No. 10, Sep. 3, 2009, pp. 2149-2158.

Wilcox et al., "Provision of antigen and CD137 signaling breaks immunological ignorance, promoting regression of poorly immunogenic tumors," J. Clin. Invest., vol. 109, No. 5, Mar. 2002, pp. 651-659.

Williams et al., "Introduction of foreign genes into tissues of living mice by DNA-coated microprojectiles," Proc. Natl. Proc. Sci. USA, vol. 88, Apr. 1991, pp. 2726-2730.

Williams et al., "The Immunoglobulin Superfamily—Domains for Cell Surface Recognition," Ann. Rev. Immunol., vol. 6, 1988, pp. 381-405.

Williams et al., "Nitric Oxide Synthase Plays a Signaling Role in TCR-Triggered Apoptotic Death," The Journal of Immunology, vol. 161, 1998, pp. 6526-6531.

Winter et al., "Man-made antibodies," Nature, vol. 349, Jan. 24, 1991, pp. 293-299.

Winter et al., "Making Antibodies by Phage Display Technology," Ann. Rev. Immunol., vol. 12, 1994, pp. 433-455.

Wintterle et al., "Expression of the B7-Related Molecule B7-H1 by Glioma Cells: A Potential Mechanism of Immune Paralysis," Cancer Research, vol. 63, Nov. 1, 2003, pp. 7462-7467.

Wofsy et al., "The Proliferating Cells in Autoimmune MRL/ 1pr Mice Lack L3T4, an Antigen on "Helper" T Cells that Is Involved in the Response to Class II Major Histocompatibility Antigens," The Journal of Immunology, vol. 132, No. 6, Jun. 1984, pp. 2686-2689.

Wofsy, "Treatment of Murine Lupus with Anti-CD4 Morioclonal Antibodies," Immunol. Ser., vol. 59, 1993, pp. 221-236.

Wolff et al., "Direct Gene Transfer into Mouse Muscle in Vivo," Science, vol. 247, Mar. 23, 1990, pp. 1465-1468.

Wong et al., "Human GM-CSF: Molecular Cloning of the Complementary DNA and Purification of the Natural and Recombinant Proteins," Science, vol. 228, May 17, 1985, pp. 810-815.

Wu et al. "Kupffer Cell Suppression of CD8+ T Cells in Human Hepatocellular Carcinoma is Mediated by B7-H1/Programmed Death-1 Interactions," Cancer Res., vol. 69, No. 20, Oct. 15, 2009, pp. 8067-8075.

Wu et al., "Receptor-mediated Gene Delivery and Expression in Vivo," The Journal of Biological Chemistry, vol. 263, No. 29, Oct. 1988, pp. 14621-14624.

Wu et al., "Targeting Genes: Delivery and Persistent Expression of a Foreign Gene Driven by Mammalian Regulatory Elements in Vivo," The Journal of Biological Chemistry, vol. 264, Oct. 1989, pp. 16985-16987.

Yamazaki et al., "Expression of Programmed Death 1 Ligands by Murine T Cells and APC," The Journal of Immunology, vol. 169, 2002, pp. 5538-5545.

Yang et al., "In Vitro Priming of Tumor-Reactive Cytolytic T Lymphocytes by Combining IL-10 with B7-CD28 Costimulation," The Journal of Immunology, vol. 155, 1995, pp. 3897-3903.

Yang et al., "In vivo and in vitro gene transfer to mammalian somatic cells by particle bombardment," Proc. Natl. Acad. Sci. USA, vol. 87, Dec. 1990, pp. 9568-9572.

Yang, "Gene Transfer into Mammalian Somatic Cells in Vivo," Critical Reviews in Biotechnology, vol. 12, No. 4, 1992, pp. 335-356.

Yoshinaga et al., "T-cell co-stimulation through B7RP-1 and ICOS," Nature, vol. 402, Dec. 16, 1999, pp. 827-832.

Youngnak et al., "Differential binding properties of B7-H1 and B7-DC to programmed death-1," Biochemical and Biophysical Research Communications, vol. 307, No. 3, 2003, pp. 672-677.

Zang et al., "B7x: A widely expressed B7 family member that inhibits T cell activation," Proc. Natl. Acad. Sci. USA, vol. 100, No. 18, Sep. 2, 2003, pp. 10388-10392.

Zelenin et al., "Genetic transformation of mouse cultured cells with the help of high-velocity mechanical DNA injection," FEBS Lett., vol. 244, No. 1, Feb. 1989, pp. 65-67.

Zelenin et al., "High-velocity mechanical DNA transfer of the chloramphenicolacetyl transferase gene into rodent liver, kidney and mammary gland cells in organ explants and in vivo," FEBS Lett., vol. 280, No. 1, Mar. 1991, pp. 94-96.

Zhang et al., "B7-H1-targeted immunotherapy for head and neck cancer," Expert Opinion on Biological Therapy, vol. 4, No. 10, 2004, pp. 1577-1583.

Zhou et al., "Inducible-costimulator-mediated suppression of human immunodeficiency virus type 1 replication in CD4+ T lymphocytes," Virology, vol. 325, No. 2, 2004, pp. 252-263.

Zips et al., "New Anticancer Agents: In Vitro and In Vivo Evaluation," In Vivo, vol. 19, 2005, pp. 1-7.

Zumla et al., "Granulomatous Infections: Etiology and Classification," Clinical Infectious Diseases, vol. 23, 1996, pp. 146-158.

Zwiebel et al., "Drug Delivery by Genetically Engineered Cell Implants," Ann. N.Y. Acad Sci., vol. 618, 1991, pp. 394-404.

```
CCCACGCGTCCGCAGCTTCCCGAGGCTCCGCACCAGCCGCGCTTCTGTCCGCC
TGCAGGGCATTCCAGAAAGATGAGGATATTTGCTGTCTTTATATTCATGACCT
ACTGGCATTTGCTGAACGCATTTACTGTCACGGTTCCCAAGGACCTATATGTG
GTAGAGTATGGTAGCAATATGACAATTGAATGCAAATTCCCAGTAGAAAAAC
AATTAGACCTGGCTGCACTAATTGTCTATTGGGAAATGGAGGATAAGAACAT
TATTCAATTTGTGCATGGAGAGGAAGACCTGAAGGTTCAGCATAGTAGCTAC
AGACAGAGGGCCCGGCTGTTGAAGGACCAGCTCTCCCTGGGAAATGCTGCAC
TTCAGATCACAGATGTGAAATTGCAGGATGCAGGGGTGTACCGCTGCATGAT
CAGCTATGGTGGTGCCGACTACAAGCGAATTACTGTGAAAGTCAATGCCCCA
TACAACAAAATCAACCAAAGAATTTTGGTTGTGGATCCAGTCACCTCTGAAC
ATGAACTGACATGTCAGGCTGAGGGCTACCCCAAGGCCGAAGTCATCTGGAC
AAGCAGTGACCATCAAGTCCTGAGTGGTAAGACCACCACCACCAATTCCAAG
AGAGAGGAGAAGCTTTTCAATGTGACCAGCACACTGAGAATCAACACAACA
ACTAATGAGATTTTCTACTGCACTTTTAGGAGATTAGATCCTGAGGAAAACCA
TACAGCTGAATTGGTCATCCCAGAACTACCTCTGGCACATCCTCCAAATGAA
AGGACTCACTTGGTAATTCTGGGAGCCATCTTATTATGCCTTGGTGTAGCACT
GACATTCATCTTCCGTTTAAGAAAAGGGAGAATGATGGATGTGAAAAAATGT
GGCATCCAAGATACAAACTCAAAGAAGCAAAGTGATACACATTTGGAGGAG
ACGTAATCCAGCATTGGAACTTCTGATCTTCAAGCAGGGATTCTCAACCTGTG
GTTTAGGGGTTCATCGGGGCTGAGCGTGACAAGAGGAAGGAATGGACCCGTG
GGATGCAGGCAATGTGGGACTTAAAAGGCCCAAGCACTGAAAATGGAACCT
GGCGAAAGCAGAGGAGGAGAATGAAGAAAGATGGAGTCAAACAGGGAGCC
TGGAGGGAGACCTTGATACTTTCAAATGCCTGAGGGGCTCATCGACGCCTGT
GACAGGGAGAAAGGATACTTCTGAACAAGGAGCCTCCAAGCAAATCATCCAT
TGCTCATCCTAGGAAGACGGGTTGAGAATCCCTAATTTGAGGGTCAGTTCCTG
CAGAAGTGCCCTTTGCCTCCACTCAATGCCTCAATTTCTTTTCTGCATGACTG
AGAGTCTCAGTGTTGGAACGGGACAGTATTTATGTATGAGTTTTCCTATTTA
TTTTGAGTCTGTGAGGTCTTCTTGTCATGTGAGTGTGGTTGTGAATGATTTCTT
TTGAAGATATATTGTAGTAGATGTTACAATTTTGTCGCCAAACTAAACTTGCT
GCTTAATGATTTGCTCACATCTAGTAAAACATGGAGTATTTGTAAGGTGCTTG
GTCTCCTCTATAACTACAAGTATACATTGGAAGCATAAAGATCAAACCGTTG
GTTGCATAGGATGTCACCTTTATTTAACCCATTAATACTCTGGTTGACCTAAT
CTTATTCTCAGACCTCAAGTGTCTGTGCAGTATCTGTTCCATTTAAATATCAG
CTTTACAATTATGTGGTAGCCTACACACATAATCTCATTTCATCGCTGTAACC
ACCCTGTTGTGATAACCACTATTATTTTACCCATCGTACAGCTGAGGAAGCAA
ACAGATTAAGTAACTTGCCCAAACCAGTAAATAGCAGACCTCAGACTGCCAC
CCACTGTCCTTTTATAATACAATTTACAGCTATATTTTACTTTAAGCAATTCTT
TTATTCAAAAACCATTTATTAAGTGCCCTTGCAATATCAATCGCTGTGCCAGG
CATTGAATCTACAGATGTGAGCAAGACAAAGTACCTGTCCTCAAGGAGCTCA
TAGTATAATGAGGAGATTAACAAGAAATGTATTATTACAATTTAGTCCAGT
GTCATAGCATAAGGATGATGCGAGGGGAAAACCCGAGCAGTGTTGCCAAGA
GGAGGAAATAGGCCAATGTGGTCTGGGACGGTTGGATATACTTAAACATCTT
AATAATCAGAGTAATTTTCATTTACAAAGAGAGGTCGGTACTTAAAATAACC
CTGAAAAATAACACTGGAATTCCTTTTCTAGCATTATATTTATTCCTGATTTGC
```

FIG. 1A

```
CTTTGCCATATAATCTAATGCTTGTTTATATAGTGTCTGGTATTGTTTAACAGT
TCTGTCTTTTCTATTTAAATGCCACTAAATTTTAAATTCATACCTTTCCATGAT
TCAAAATTCAAAAGATCCCATGGGAGATGGTTGGAAAATCTCCACTTCATCC
TCCAAGCCATTCAAGTTTCCTTTCCAGAAGCAACTGCTACTGCCTTTCATTCA
TATGTTCTTCTAAAGATAGTCTACATTTGGAAATGTATGTTAAAAGCACGTAT
TTTTAAAATTTTTTTCCTAAATAGTAACACATTGTATGTCTGCTGTGTACTTTG
CTATTTTTATTTATTTTAGTGTTTCTTATATAGCAGATGGAATGAATTTGAAGT
TCCCAGGGCTGAGGATCCATGCCTTCTTTGTTTCTAAGTTATCTTTCCCATAGC
TTTTCATTATCTTTCATATGATCCAGTATATGTTAAATATGTCCTACATATACA
TTTAGACAACCACCATTTGTTAAGTATTTGCTCTAGGACAGAGTTTGGATTTG
TTTATGTTTGCTCAAAAGGAGACCCATGGGCTCTCCAGGGTGCACTGAGTCA
ATCTAGTCCTAAAAAGCAATCTTATTATTAACTCTGTATGACAGAATCATGTC
TGGAACTTTTGTTTTCTGCTTTCTGTCAAGTATAAACTTCACTTTGATGCTGTA
CTTGCAAAATCACATTTTCTTTCTGGAAATTCCGGCAGTGTACCTTGACTGCT
AGCTACCCTGTGCCAGAAAAGCCTCATTCGTTGTGCTTGAACCCTTGAATGCC
ACCAGCTGTCATCACTACACAGCCCTCCTAAGAGGCTTCCTGGAGGTTTCGA
GATTCAGATGCCCTGGGAGATCCCAGAGTTTCCTTTCCCTCTTGGCCATATTC
TGGTGTCAATGACAAGGAGTACCTTGGCTTTGCCACATGTCAAGGCTGAAGA
AACAGTGTCTCCAACAGAGCTCCTTGTGTTATCTGTTTGTACATGTGCATTTG
TACAGTAATTGGTGTGACAGTGTTCTTTGTGTGAATTACAGGCAAGAATTGTG
GCTGAGCAAGGCACATAGTCTACTCAGTCTATTCCTAAGTCCTAACTCCTCCT
TGTGGTGTTGGATTTGTAAGGCACTTTATCCCTTTTGTCTCATGTTTCATCGTA
AATGGCATAGGCAGAGATGATACCTAATTCTGCATTTGATTGTCACTTTTTGT
ACCTGCATTAATTTAATAAATATTCTTATTTATTTTGTTACTTGGTAAAAAA
AAAAAAAAAAAAAAAAAAAAAAAAAAAAAAAAAAA
```

FIG. 1B

```
                                                       Signal peptide
  1  MRIFAVFIFMTYWHLLNAFTVTVPKDLYVVEYGSNMTIECKFPVEKQLDL
                                      *
                       Ig-V-like
 51  AALIVYWEMEDKNIIQFVHGEEDLKVQHSSYRQRARLLKDQLSLGNAALQ 101  ITDVKLQDAGVYRCMISYGGADYKRITVKVNAPYNKINQRILVVDPVTSE
                       Ig-C-like
151  HELTCQAEGYPKAEVIWTSSDHQVLSGKTTTTNSKREEKLFNVTSTLRIN
              *                                     *
201  TTTNEIFYCTFRRLDPEENHTAELVIPELPLPLAHPPNERTHLVILGAILLC
                              *
251  LGVALTFIFLRLRKGRMMDVKKCGIQDTNSKKQSDTHLEET
         TM
```

FIG. 2A

```
                              *
B7-H1   50  VEYGSNMTIECKFPVEKQLDLAALIVYWEM
B7-1    43     KEVATLSCGHNVS-VEELAQTRIYWQK
B7-2    30  AYFNETADLPCQFANSQNQSLSELVVFWQD

80  EDKNIIQFVHGEED-LKVQHSSYRQRARLL
        68  EKKMVLTMMSGDMN----IWPEYKNRTIFD
        60  QENLVLNEVYLGKEKFDSVHSKYMGRTSFD

*
        89  KDQLSLGNAALQITDVKLQDAGVYRCMISY
        95  IT----NNLSIVILALRPSDEGTYECVVLK
        90  S-----DSWTLRIHNLQIKDKGLYQCIIHH

119  GGADYKR----ITVKVNAPYNKINQRILVV
       121  YEKDAFKREHLAEVTLSVKADFPTPSISDF
       115  KKPTGMIRIHQMNSELSVLANFSQPEIVPI

*
       145  DPVTSEHEL--TC-QAEGYPKA-EVIWTSS
       151  EIPTSNIRR-IICSTSGGFPEP-HLSWLEN
       145  SNITENVYINLTCSSIHGYPEPKKMSVLLR

171  DHQ---VLSGKTTTTNSKREEKLFNVTSTL
       179  GE----ELNAINTTVSQDPETELYAVSSKL
       175  TKNSTIEYDGIMQK-SQDNVTELYDVSISL

*
       198  RIN---TTTNEIFYCTFRRLDPEENHTAEL
       205  DFN---MTTNHSFMCLIKYGHLRVN--QTF
       204  SVSFPDVTSNMTIFCILETDKTRLLS-SPE

226  VIPELPLAHPPNERT
       230  NWNTTKQEHFPDNLL
       233  STELEDPQPPPDHIP              FIG. 2B
```

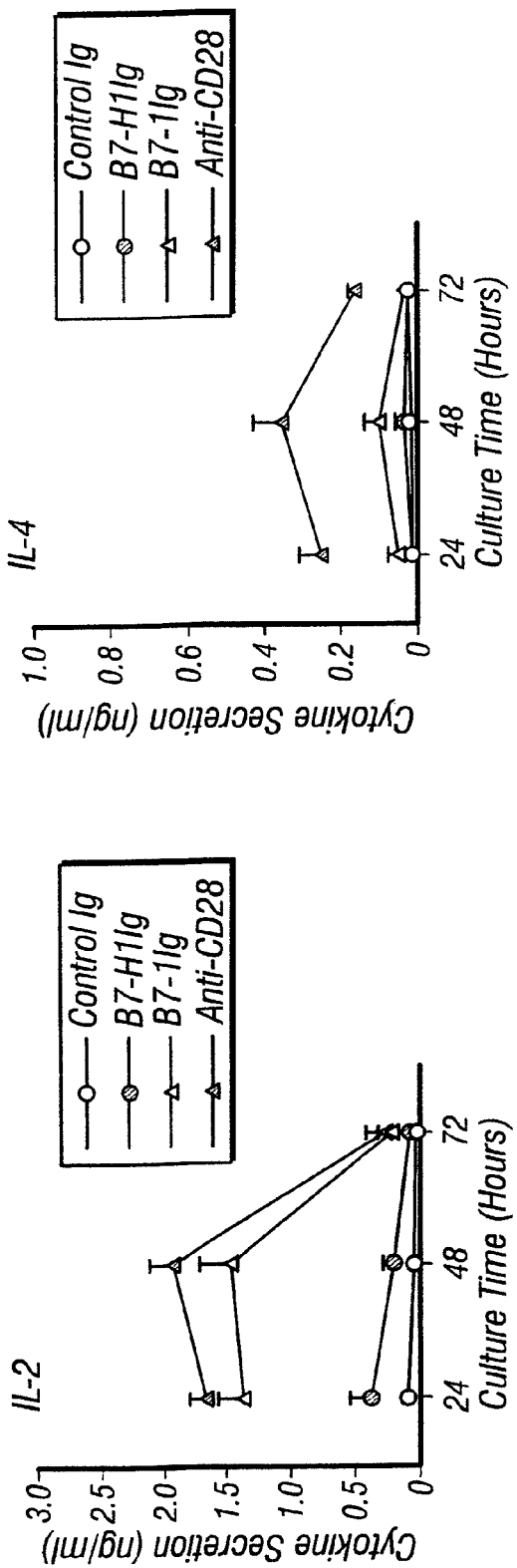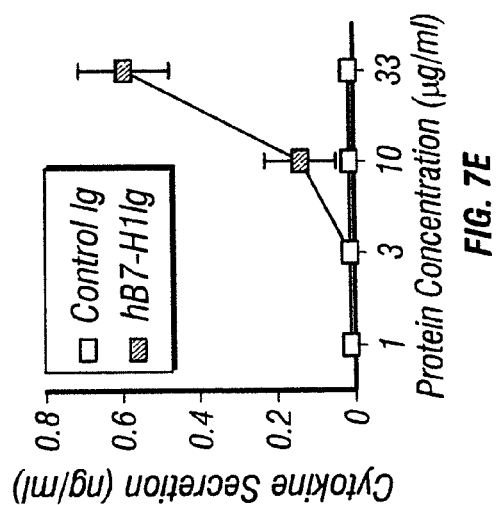
FIG. 7D
FIG. 7E
FIG. 7C

ATGAGGATATTTGCTGGCATTATATTCACAGCCTGCTGTCACTTGCTACGGGC
GTTTACTATCACGGCTCCAAAGGACTTGTACGTGGTGGAGTATGGCAGCAAC
GTCACGATGGAGTGCAGATTCCCTGTAGAACGGGAGCTGGACCTGCTTGCGT
TAGTGGTGTACTGGGAAAAGGAAGATGAGCAAGTGATTCAGTTTGTGGCAGG
AGAGGAGGACCTTAAGCCTCAGCACAGCAACTTCAGGGGGAGAGCCTCGCT
GCCAAAGGACCAGCTTTTGAAGGGAAATGCTGCCCTTCAGATCACAGACGTC
AAGCTGCAGGACGCAGGCGTTTACTGCTGCATAATCAGCTACGGTGGTGCGG
ACTACAAGCGAATCACGCTGAAAGTCAATGCCCCATACCGCAAAATCAACCA
GAGAATTTCCGTGGATCCAGCCACTTCTGAGCATGAACTAATATGTCAGGCC
GAGGGTTATCCAGAAGCTGAGGTAATCTGGACAAACAGTGACCACCAACCCG
TGAGTGGGAAGAGAAGTGTCACCACTTCCCGGACAGAGGGGATGCTTCTCAA
TGTGACCAGCAGTCTGAGGGTCAACGCCACAGCGAATGATGTTTTCTACTGT
ACGTTTTGGAGATCACAGCCAGGGCAAAACCACACAGCGGAGCTGATCATCC
CAGAACTGCCTGCAACACATCCTCCACAGAACAGGACTCACTGGGTGCTTCT
GGGATCCATCCTGTTGTTCCTCATTGTAGTGTCCACGGTCCTCCTCTTCTTGAG
AAAACAAGTGAGAATGCTAGATGTGGAGAAATGTGGCGTTGAAGATACAAG
CTCAAAAAACCGAAATGATACACAATTCGAGGAGACGTAA

FIG. 10

MRIFAGIIFTACCHLLRAFTITAPKDLYVVEYGSNVTMECRFPVERELDLLALVV
YWEKEDEQVIQFVAGEEDLKPQHSNFRGRASLPKDQLLKGNAALQITDVKLQDA
GVYCCIISYGGADYKRITLKVNAPYRKINQRISVDPATSEHELICQAEGYPEAEVI
WTNSDHQPVSGKRSVTTSRTEGMLLNVTSSLRVNATANDVFYCTFWRSQPGQN
HTAELIIPELPATHPPQNRTHWVLLGSILLFLIVVSTVLLFLRKQVRMLDVEKCGV
EDTSSKNRNDTQFEET

FIG. 11

```
                    ———signal peptide———
mouse B7-H1   1  MRIFAGIIFTACCHLLRAFTITAPKDLYVVEYGSN    35
human B7-H1   1  MRIFAVFIFMTYWHLLNAFTVTVPKDLYVVEYGSN    35
                          ———IgV-like domain———
mouse B7-H1  36  VTMECRFPVERELDLLALVVYWEKEDEQVIQFVAG     70
human B7-H1  36  MTIECKFPVEKQLDLAALIVYWEMEDKNIIQFVHG     70 mouse B7-H1  71  EEDLKPQHSNFRGRASLPKDQLLKGNAALQITDVK    105
human B7-H1  71  EEDLKVQHSSYRQRARLLKDQLSLGNAALQITDVK    105 mouse B7-H1 106  LQDAGVYCCIISYGGADYKRITLKVNAPYRKINQR    140
human B7-H1 106  LQDAGVYRCMISYGGADYKRITVKVNAPYNKINQR    140
                          ———IgC-like domain———
mouse B7-H1 141  IS-VDPATSEHELICQAEGYPEAEVIWTNSDHQPV    174
human B7-H1 141  ILVVDPVTSEHELTCQAEGYPKAEVIWTSSDHQVL    175 mouse B7-H1 175  SGKRSVTTSRTEGMLLNVTSSLRVNATANDVFYCT    209
human B7-H1 176  SGKTTTTNSKREEKLFNVTSTLRINTTTNEIFYCT    210
```

*FIG. 12A-1*

```
mouse B7-H1 210 FWRSQPGQNHTAELIIPELPATHPPQNRTHWVLLG 244
human B7-H1 211 FRRLDPEENHTAELVIPELPLAHPPNERTHLVILG 245
                                            ————TM————
mouse B7-H1 245 SILFLIVSTVLLFLRKQVRMLDVEKCGVEDTSS 279
human B7-H1 246 AILCLGVALTFIFRLRKG-RMMDVKKCGIQDTNS 279
                 cytoplasmic
mouse B7-H1 280 KNRNDTQFEET 290
human B7-H1 280 KKQSDTHLEET 290
```

*FIG. 12A-2*

```
mB7-H1        1                MRIFAG..............................IIFTACC  13
mB7-1         1           MACNCQLMQDT.......PLLKFPCPRLILLFVL               27
mB7-2         1               MDPRCTMG...........LAILIFVT                  16
mB7h/B7RP-1   1  MQLKCPCFVSLGTRQPVWKKLHVSSGFFSGLGLFL                        35
                         C              *               IL mB7-H1       14  HLLRAFTITAPKDLYVVEYGSNVTMECRFPVEREL                        48
mB7-1        28  LIRISQVSSDVDEQLSKSVKDKVLLPCRYNSPHED                        62
mB7-2        17  VLLISDAVSVETQAYFNGT...AYLPCPETKAQNI                        48
mB7h/B7RP-1  36  LLLSSLCAASAETEVGAMVGSNVLSCIDPHRRHF                         70
                  LL S                    V L C mB7-H1       49  DLLALVVYWEK...EDEQVIQ.FVAGEEDLKPQHSN                        80
mB7-1        63  .ESEDRIYWQK...HDKVVLS...VIAGKLK.VWPE                        90
mB7-2        49  SLSELVFWQD...QQKLVLYEHYLGTEKLDSVNAK                        81
mB7h/B7RP-1  71  NLSGLYVYWQIENPEVSVTYLPYKSPGIN.VDSS                         104
                   LS L VYWQ               V      L V  * mB7-H1       81  FRGRASLPKDQLLKGNAALQITDVKLQDAGVYCCI                        115
nB7-1        91  YKNR...TLYDNT....TYSLIILGLVLSDRGTYSCV                      120
mB7-2        82  YLGR...TSFDRN...NWTLRLHNVQIKDMGSYDCF                       111
mB7h/B7RP-1 105  YKNRGHLSLDSMKQGNFSLYLKNVTPQDTQEFTCR                        139
                  Y R    D       N L     V   D G Y C
```

FIG. 12B-1

| | | | |
|---|---|---|---|
| mB7-H1 | 116 | IS......YGGADYKRITKVNAPYRKINQRISVD | 144 |
| mB7-1 | 121 | VQKKERGTYEVKHLALVKLSIKADFSTPNITESGN | 155 |
| mB7-2 | 112 | IQKKPPTGSIILQQTLTELSVIANFSEPEIKLAQN | 146 |
| mB7h/b7RP-1 | 140 | VFMNTATELVKILEEVVRLRVAANFSTPVISTSDS | 174 |
| | | L V A F S P I S | |
| | | * | |
| mB7-H1 | 145 | PATSE.HEIICQAE...GYPEAE...VIWNSDHQPVS | 175 |
| mB7-1 | 156 | PSADT.KRITCFASGGFPKPR..FSWLENGRELPG | 187 |
| mB7-2 | 147 | VTGNSGINLTCTSKQGHPKPKKMYFLITNSTNEYG | 181 |
| mB7h/b7RP-1 | 175 | SNPGQERTYTCMSKNGYPEPN...LYWINITDNSLI | 207 |
| | | TC G P P W | |
| mB7-H1 | 176 | GKRSVTT...SRTEGMLNVTSSLRVNA....TANDV | 205 |
| mB7-1 | 188 | INTTIS....QDPESELYTISSQLDFNT....TRNHT | 216 |
| mB7-2 | 182 | DNMQIS....QDNVTELFSISNSLSFPDGVWHMT | 213 |
| mB7h/b7RP-1 | 208 | DTALQNNTVYLNKLGLYDVISTLRLPW....TSRGD | 239 |
| | | L S L T | |
| | | * | |
| mB7-H1 | 206 | FYCTFWRSQPGQNHT......AELIIPELPATHPPQN | 236 |
| mB7-1 | 217 | IKCLIKYGDAHVS.......EDFTWEKPPEDPPDS | 244 |
| mB7-2 | 214 | VVCVLETESMKISSK....PLNFTQEFP..SPQ... | 240 |
| mB7h/b7RP-1 | 240 | VLCCVENVALHQNITSISQAESFTGNNTK.NPQE. | 272 |
| | | C E FT E P P | |

*FIG. 12B-2*

```
mB7-H1         237  R..THWVLLGSILFLIVSTVLLFL.....RKQVR  265
mB7-1          245  KNTLVLFGAGFGAVITVVIIKCFCKHRSCFR     279
mB7-2          241  ..TYWKEITASVTVALLIVMLIIVCHKKPNQPSR  273
mB7h/B7RP-1    273  ..THNNELKVLVPVLAVLAAAAFVS.....FIIYR 300
                              T          V                R mB7-H1         266  ........MLDVEKCGVEDTSSKNR..NDTQFEET        290
mB7-1          280  ........RNE.ASRETNNSLTFGPEALAEQIVFL        306
mB7-2          274  PSNTASKLERDSNADRETINLKELEPQIASAKPNAE       308
mB7h/b7RP-1    301  ........RTR.PHRSYTGPKTV..QLEITDHA          322
                              R     RE      K             R
```

FIG. 12B-3 anti-mB7-1-FITC ⟶ anti-mB7H/PE ⟶

B7-H1 ANTIBODIES AND METHOD OF USE

CROSS-REFERENCE TO RELATED APPLICATIONS

The present application is a 37 C.F.R. §1.53(b) continuation of U.S. application Ser. No. 12/421,310 filed Apr. 9, 2009, which is a 37 C.F.R. §1.53(b) continuation of U.S. application Ser. No. 12/347,492 filed Dec. 31, 2008, which is a 37 C.F.R. §1.53(b) continuation of U.S. application Ser. No. 09/649,108 filed Aug. 28, 2000 (abandoned), which is a 37 C.F.R. §1.53(b) continuation-in-part of U.S. application Ser. No. 09/451,291 filed Nov. 30, 1999 (now U.S. Pat. No. 6,803,192 issued Oct. 12, 2004). The contents of each of these applications is hereby incorporated by reference.

STATEMENT OF FEDERALLY FUNDED RESEARCH

This invention was made with government support under grant number CA079915 awarded by the National Institutes of Health. The government has certain rights in the invention.

REFERENCE TO SEQUENCE LISTING

This application contains a Sequence Listing submitted in electronic and print form. The electronic and print form of the Sequence Listing are identical to each other pursuant to 37 C.F.R. §1.52(e)(4), contains the following file "SEQUENCE LISTING.txt," having a size in bytes of 30.49 KB, recorded on Apr. 9, 2009. The information contained in the Sequence Listing is hereby incorporated by reference in its entirety pursuant to 37 C.F.R. §1.52(e)(5).

BACKGROUND OF THE INVENTION

The invention is generally in the field of immunoregulation, and specifically T cell response regulation.

Mammalian T lymphocytes recognize antigenic peptides bound to major histocompatibility complex (MHC) molecules on the surface of antigen presenting cells (APC). The antigenic peptides are generated by proteolytic degradation of protein antigens within the APC. The interaction of the T cells with the APC and the subsequent response of the T cells are qualitatively and quantitatively regulated by interactions between cell surface receptors on the T cells with both soluble mediators and ligands on the surface of APC.

SUMMARY OF THE INVENTION

The invention is based on the cloning of human and mouse cDNA molecules encoding novel homologous molecules that co-stimulate the T cell responses of both species and on the functional characterization of the polypeptides that the cDNA molecules encode. The human polypeptide is designated hB7-H1 and the mouse polypeptide mB7-H1. Text that refers to B7-H1 without specifying human versus mouse is pertinent to both forms of B7-H1. The invention features DNA molecules encoding the hB7-H1, mB7-H1 polypeptides, functional fragments of the polypeptides, and fusion proteins containing the polypeptides or functional fragments of the polypeptides, hB7-H1 and mB7-H1 and functional fragments of both, vectors containing the DNA molecules, and cells containing the vectors. Also included in the invention are antibodies that bind to the B7-H1 polypeptides. The invention features in vitro, in vivo, and ex vivo methods of co-stimulating T cell responses, methods of screening for compounds that inhibit or enhance T cell responses, and methods for producing the above polypeptides and fusion proteins.

Specifically the invention features an isolated DNA including: (a) a nucleic acid sequence that (i) encodes a B7-H1 polypeptide with the ability to co-stimulate a T cell, and (ii) hybridizes under stringent conditions to the complement of a sequence that encodes a polypeptide with an amino acid sequence with SEQ ID NO:1 or SEQ ID NO:3; or (b) a complement of this nucleic acid sequence. The nucleic acid sequence included in the isolated DNA will be at least 10 bp, 15 bp, 25 bp, 50 bp, 75 bp, 100 bp, 125 bp, 150 bp, 175 bp, 200 bp, 250 bp, 300 bp, 350 bp, 400 bp, 450 bp, 500 bp, 550 bp, 600 bp, 650 bp, 700 bp, 750, by 800 bp, 850 bp, or 870 bp long. The nucleic acid sequence can encode a B7-H1 polypeptide that includes an amino sequence with SEQ ID NO:1 or SEQ ID NO:3 or it can have a nucleotide sequence with SEQ ID NO:2 or SEQ ID NO:4. The nucleic acid sequence can also encode functional fragments of these B7-H1 polypeptides.

The invention also embodies an isolated B7-H1 polypeptide encoded by a DNA that includes a nucleic acid sequence that (i) encodes a polypeptide with the ability to co-stimulate a T cell and (ii) hybridizes under stringent conditions to the complement of a sequence that encodes a polypeptide with an amino acid sequence with SEQ ID NO:1 or SEQ ID NO:3. The B7-H1 polypeptide can include an amino sequence of amino acid residue 20, 21, 22, 23, 24, 25, 26, 27, 28, 29, 30, 31, or 32, to amino acid residue 290 of SEQ ID NO:1 or SEQ ID NO:3. The invention also encompasses B7-H1 polypeptides that include an amino acid sequence with SEQ ID NO:1 or SEQ ID NO:3, or either of these amino acid sequences but differing solely by one or more conservative substitutions. The polypeptides of the invention include fusion proteins containing a first domain and at least one additional domain. The first domain can be any of the B7-H1 polypeptides described above or a functional fragment of any of these polypeptides. The at least one additional domain can be a heterologous targeting or leader sequence, an amino acid sequence that facilitates purification, detection, or solubility of the fusion protein. The second domain can be, for example, all or part of an immunoglobulin (Ig) heavy chain constant region. Also included are isolated nucleic acid molecules encoding the fusion proteins.

The invention features vectors containing any of the DNAs of the invention and nucleic acid molecules encoding the fusion proteins of the invention. The vectors can be expression vectors in which the nucleic acid coding sequence or molecule is operably linked to a regulatory element which allows expression of the nucleic acid sequence or molecule in a cell. Also included in the invention are cells (e.g., mammalian, insect, yeast, fungal, or bacterial cells) containing any of the vectors of the invention.

Another embodiment of the invention is a method of co-stimulating a T cell that involves contacting the T cell with any of the B7-H1 polypeptides of the invention, functional fragments thereof, or fusion proteins of the invention; these 3 classes of molecule are, for convenience, designated "B7-H1 agents". The contacting can be by culturing any of these B7-H1 agents with the T cell in vitro. Alternatively, the T cell can be in a mammal and the contacting can be, for example, by administering any of the B7-H1 agents to the mammal or administering a nucleic acid encoding the B7-H1 agent to the mammal. In addition, the method can be an ex vivo procedure that involves providing a recombinant cell which is the progeny of a cell obtained from the mammal and has been transfected or transformed ex vivo with a nucleic acid encoding any of the B7-H1 agents so that the cell expresses the B7-H1 agent; and administering the cell to the mammal. In this ex vivo procedure, the cell can be an antigen presenting cell (APC) that expresses the B7-H1 agent on its surface. Furthermore, prior to administering to the mammal, the APC can be pulsed with an antigen or an antigenic peptide. In any of the above methods, the mammal can be suspected of having, for example, an immunodeficiency disease, an inflammatory condition, or an autoimmune disease. In addition, in any of the methods, the T cell can be a helper T cell, e.g., a T cell that helps an effector (e.g., a cytotoxic T lymphocyte (CTL) or B cell antibody) response. An antibody response can be, for example, an IgM, IgG1, IgG2a, IgG2b, IgG3, IgG4, IgE, or IgA antibody response. Co-stimulation of a T cell by any of the B7-H1 agents can result in an increase in the level of CD40 ligand on the surface of the T cell.

The invention includes a method of identifying a compound that inhibits an immune response. The method involves: providing a test compound; culturing, together, the compound, one or more B7-H1 agents, a T cell, and a T cell activating stimulus; and determining whether the test compound inhibits the response of the T cell to the stimulus, as an indication that the test compound inhibits an immune response. The invention also embodies a method of identifying a compound that enhances an immune response. The method involves: providing a test compound; culturing, together, the compound, one or more of B7-H1 agents, a T cell, and a T cell activating stimulus; and determining whether the test compound enhances the response of the T cell to the stimulus, as an indication that the test compound enhances an immune response. In both these methods, the stimulus can be, for example, an antibody that binds to a T cell receptor or a CD3 polypeptide. Alternatively, the stimulus can be an alloantigen or an antigenic peptide bound to a major histocompatibility complex (MHC) molecule on the surface of an antigen presenting cell (APC). The APC can be transfected or transformed with a nucleic acid encoding the B7-H1 agent and the B7-H1 agent can be expressed on the surface of the APC.

The invention also features an antibody (e.g., a polyclonal or a monoclonal antibody) that binds to any of the B7-H1 polypeptides of the invention, e.g., the polypeptide with SEQ ID NO:1 or SEQ ID NO:3.

The invention also features a method of producing any of the B7-H1 polypeptides of the invention, functional fragments thereof, or fusion proteins of the invention. The method involves culturing a cell of the invention and purifying the relevant B7-H1 protein from the culture.

"Polypeptide" and "protein" are used interchangeably and mean any peptide-linked chain of amino acids, regardless of length or post-translational modification. The invention also features B7-H1 polypeptides with conservative substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The term "isolated" polypeptide or peptide fragment as used herein refers to a polypeptide or a peptide fragment which either has no naturally-occurring counterpart (e.g., a peptidomimetic), or has been separated or purified from components which naturally accompany it, e.g., in tissues such as pancreas, liver, spleen, ovary, testis, muscle, joint tissue, neural tissue, gastrointestinal tissue, or body fluids such as blood, serum, or urine. Typically, the polypeptide or peptide fragment is considered "isolated" when it is at least 70%, by dry weight, free from the proteins and naturally-occurring organic molecules with which it is naturally associated. Preferably, a preparation of a polypeptide (or peptide fragment thereof) of the invention is at least 80%, more preferably at least 90%, and most preferably at least 99%, by dry weight, the polypeptide (or the peptide fragment thereof), respectively, of the invention. Thus, for example, a preparation of polypeptide x is at least 80%, more preferably at least 90%, and most preferably at least 99%, by dry weight, polypeptide x. Since a polypeptide that is chemically synthesized is, by its nature, separated from the components that naturally accompany it, the synthetic polypeptide or nucleic acid is "isolated."

An isolated polypeptide (or peptide fragment) of the invention can be obtained, for example, by extraction from a natural source (e.g., from human tissues or bodily fluids); by expression of a recombinant nucleic acid encoding the peptide; or by chemical synthesis. A peptide that is produced in a cellular system different from the source from which it naturally originates is "isolated," because it will be separated from components which naturally accompany it. The extent of isolation or purity can be measured by any appropriate method, e.g., column chromatography, polyacrylamide gel electrophoresis, or HPLC analysis.

An "isolated DNA" means DNA free of one or both of the genes that flank the gene containing the DNA of interest in the genome of the organism in which the gene containing the DNA of interest naturally occurs. The term therefore includes a recombinant DNA incorporated into a vector, into an autonomously replicating plasmid or virus, or into the genomic DNA of a prokaryote or eukaryote. It also includes a separate molecule such as: a cDNA where the corresponding genomic DNA has introns and therefore a different sequence; a genomic fragment; a fragment produced by polymerase chain reaction (PCR); a restriction fragment; a DNA encoding a non-naturally occurring protein, fusion protein, or fragment of a given protein; or a nucleic acid which is a degenerate variant of a naturally occurring nucleic acid. In addition, it includes a recombinant nucleotide sequence that is part of a hybrid gene, i.e., a gene encoding a fusion protein. Also included is a recombinant DNA that includes a portion of SEQ ID NO:2, SEQ ID NO:4, or SEQ ID NO:5. It will be apparent from the foregoing that isolated DNA does not mean a DNA present among hundreds to millions of other DNA molecules within, for example, cDNA or genomic DNA libraries or genomic DNA restriction digests in, for example, a restriction digest reaction mixture or an electrophoretic gel slice.

As used herein, a polypeptide that "co-stimulates" a T cell is a polypeptide that, upon interaction with a cell-surface molecule on the T cell, enhances the response of the T cell. The T cell response that results from the interaction will be greater than the response in the absence of the polypeptide. The response of the T cell in the absence of the co-stimulatory polypeptide can be no response or it can be a response significantly lower than in the presence of the co-stimulatory polypeptide. It is understood that the response of the T cell can be an effector (e.g., CTL or antibody-producing B cell) response, a helper response providing help for one or more effector (e.g., CTL or antibody-producing B cell) responses, or a suppressive response.

As used herein, an "activating stimulus" is a molecule that delivers an activating signal to a T cell, preferably through the antigen specific T cell receptor (TCR). The activating stimulus can be sufficient to elicit a detectable response in the T cell. Alternatively, the T cell may require co-stimulation (e.g., by a B7-H1 polypeptide) in order to respond detectably to the activating stimulus. Examples of activating stimuli include, without limitation, antibodies that bind to the TCR or to a polypeptide of the CD3 complex that is physically associated with the TCR on the T cell surface, alloantigens, or an antigenic peptide bound to a MHC molecule.

As used herein, a "fragment" of a B7-H1 polypeptide is a fragment of the polypeptide that is shorter than the full-length polypeptide. Generally, fragments will be five or more amino acids in length. An antigenic fragment has the ability to be recognized and bound by an antibody.

As used herein, a "functional fragment" of a B7-H1 polypeptide is a fragment of the polypeptide that is shorter than the full-length polypeptide and has the ability to co-stimulate a T cell. Methods of establishing whether a fragment of an B7-H1 molecule is functional are known in the art. For example, fragments of interest can be made by either recombinant, synthetic, or proteolytic digestive methods. Such fragments can then be isolated and tested for their ability to co-stimulate T cells by procedures described herein.

As used herein, "operably linked" means incorporated into a genetic construct so that expression control sequences effectively control expression of a coding sequence of interest.

As used herein, the term "antibody" refers not only to whole antibody molecules, but also to antigen-binding fragments, e.g., Fab, F(ab')$_2$, Fv, and single chain Fv fragments. Also included are chimeric antibodies.

As used herein, an antibody that "binds specifically" to an isolated B7-H1 polypeptide encoded by a DNA that includes a nucleic acid sequence that (i) encodes a polypeptide with the ability to co-stimulate a T cell and (ii) hybridizes under stringent conditions to the complement of a sequence that encodes a polypeptide with an amino acid sequence with SEQ ID NO:1 or SEQ ID NO:3, is an antibody that does not bind to B7-1 or B7-2 polypeptides.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., enhancing immune responses in mammalian subjects, will be apparent from the following description, from the drawings and from the claims.

BRIEF DESCRIPTION OF THE DRAWINGS

FIG. 1 is a depiction of the nucleotide sequence of a cDNA fragment (SEQ ID NO: 5) that includes the coding sequence (nucleotides 72-870 of SEQ ID NO:5) (SEQ ID NO:2) of hB7-H1.

FIG. 2a is a depiction of the amino acid sequence of hB7-H1 (SEQ ID NO:1). The signal peptide, Ig-V-like domain, Ig-C-like domain, and transmembrane ("TM") domain are indicated. Potential N-linked glycosylation sites are indicated by *.

FIG. 2b is a depiction of the amino acid sequences of the extracellular domains of hB7-H1 (SEQ ID NO:10), human B7-1 (hB7-1; SEQ ID NO:11), and human B7-2 (hB7-2; SEQ ID NO:12) aligned for maximum homology. Identical amino acid residues are shaded in bold and conserved residues are boxed. Conserved cysteine residues are indicated by *.

FIGS. 7a-7d are a series of line graphs showing the ability of hB7-H1Ig, human B7-1Ig, or antibody specific for human CD28 to co-stimulate the production of interleukin-(IL-)10 (FIG. 7a), interferon-γ (IFN-γ) (FIG. 7b), IL-2 (FIG. 7c), or IL-4 (FIG. 7d) by human T cells responding to immobilized antibody specific for CD3. FIG. 7e is a line graph showing the ability of various concentrations of hB7-H1Ig to co-stimulate the production of IL-2 by human T cells responding to immobilized antibody specific for CD3.

FIG. 10 is a depiction of the nucleotide sequence of cDNA encoding mB7-H1 (SEQ ID NO:4).

FIG. 11 is a depiction of the amino acid sequence of mB7-H1 (SEQ ID NO:3). FIG. 12a is a depiction of the amino acid sequence of mB7-H1 (SEQ ID NO:3) aligned with the amino acid sequence of hB7-H1 (SEQ ID NO:1). The signal peptide, IgV-like domain, IgC-like domain, transmembrane ("TM") domain, and cytoplasmic domain ("cytoplasmic") of mB7-H1 are indicated.

FIG. 12b is a depiction of the amino acid sequences of mB7-H1, mouse B7-1 (mB7-1; SEQ ID NO:13), mouse B7-2 (mB7-2: SEQ ID NO:14), and mB7h/B7KF-1 (SEQ ID NO:15) aligned for maximum homology. Identical amino acid residues are shaded and conserved amino acid residues are boxed. Conserved cysteine residues are indicated by *.

DETAILED DESCRIPTION

Figure 3:
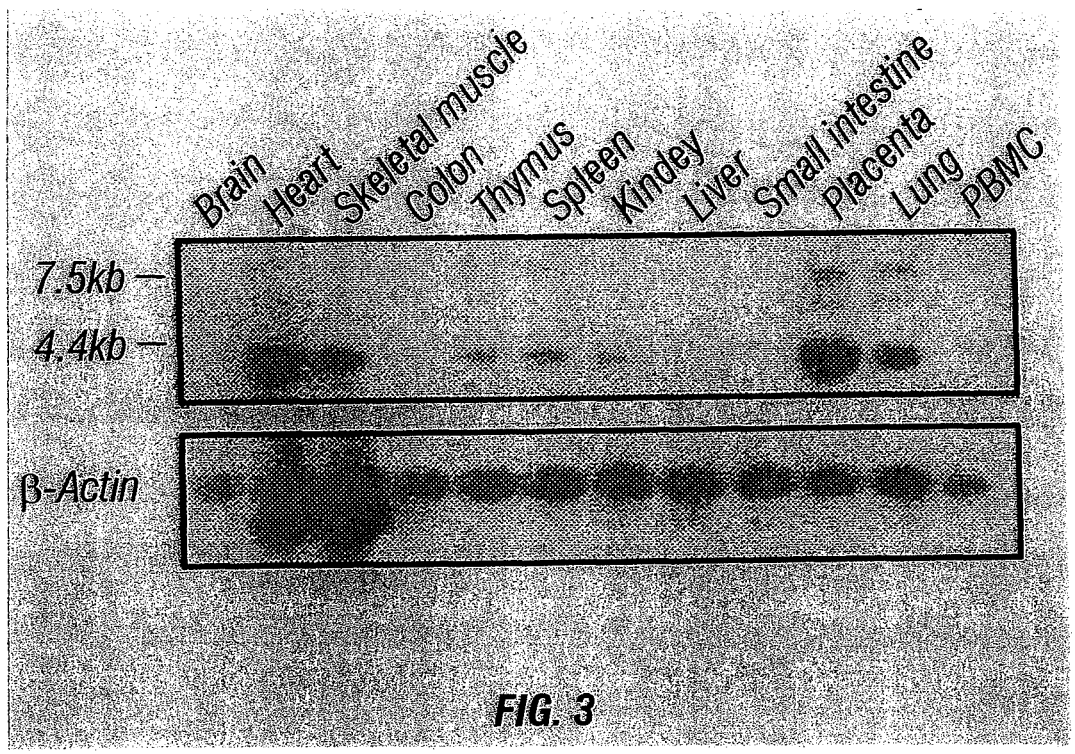
FIG. 3 is a photograph of a Northern blot showing expression of hB7-H1 mRNA in various human tissues.

Using PCR primers with sequences derived from an expressed sequence tag (EST) that had significant homology to human B7-1 and B7-2 and a human cDNA library as a source of template, cDNA sequences corresponding to regions of a transcript 5' and 3' of the EST were identified. A cDNA molecule (SEQ ID NO:5) that included a open reading frame (orf) (SEQ ID NO:2) encoding a novel B7-related molecule was then generated using PCR primers with sequences derived from the 3' and 5' ends and cloned.

Translation of the cDNA sequence indicated that the polypeptide (SEQ ID NO:1) that it encoded (hB7-H1) is a type I transmembrane protein of 290 amino acids containing an immunoglobulin (Ig) V-like domain, Ig C-like domain, a transmembrane domain and a cytoplasmic domain of 30 amino acids. Northern blot analysis showed strong expression of the gene encoding hB7-H1 in heart, skeletal muscle, placenta, and lung, and weak expression in thymus, spleen, kidney, and liver. Expression was undetectable in brain, colon, small intestine, and peripheral blood mononuclear cells (PBMC).

Using an antiserum produced by immunization of mice with a recombinantly produced fusion protein that included the hB7-H1 protein, expression by fluorescence flow cytometry indicated negligible expression on resting T and B cells. On the other hand, about 16% of CD14+ monocytes constitutively expressed the molecule on their surface. Activation of T cells increased expression such that about 30% expressed cell-surface hB7-H1.

Activation resulted in about 90% of monocytes expressing hB7-1H, but only about 6% of B cells expressed it after activation.

Transfection of 293 cells resulted in an hB7-H1 expressing cell line (hB7-H1/293) which was used for binding experiments. These experiments and others with a CD28 expressing cell line indicated that neither CTLA4, ICOS, nor CD28 were receptors for hB7-H1.

In vitro experiments with isolated human T cells and the hB7-H1-containing fusion protein indicated that hB7-H1 had no direct activity on T cells, it enhanced ("co-stimulated") T cell proliferative responses induced by both antibody specific for human CD3 and MHC alloantigens. This co-stimulatory activity was significantly more potent when the hB7-H1 was immobilized in the plastic tissue culture wells used for the cultures than when it was in solution. Similar experiments indicated that hB7-H1 had a dramatic and selective enhancing effect on the production of interleukin (IL)-10 induced by T cell activation. Moreover this IL-10 enhancing activity appeared to be dependent on at least low amounts of IL-2. Analysis of T cells activated by anti-CD3 antibody and hB7-H1Ig indicated that hB7-H1 enhances apoptosis and expression of Fas and FasL.

In addition, using a strategy similar to that used to clone hB7-H1 cDNA, a cDNA molecule containing an orf encoding mouse B7-H1 (mB7-H1) was cloned, the nucleotide sequence of the orf (SEQ ID NO:4) was obtained, and the amino acid sequence of the encoded sequence (SEQ ID NO:3) was derived. mB7-H1 is exactly the same length (290 amino acids) and has the same domain structure as hB7-H1. Moreover, mB7-H1 has a similar tissue distribution to hB7-H1. mB7-H1 co-stimulated the response of mouse T cells with its effect being more potent on CD4+ than on CD8+ T cells. In addition, like hB7-H1, mB7-H1 co-stimulates the production of high levels of IL-10 by T cells. mB7-H1 also enhanced the production of both interferon-γ (IFN-γ) and granulocyte macrophage-colony stimulating factor (GM-CSF) by T cells. While mB7-H1 showed no significant ability to enhance CTL responses, it did greatly increase antibody responses and, in particular, IgG2a antibody responses. Finally, co-stimulation of T cells with mB7-H1 caused an increase in the level of CD40 ligand (CD40L) on the surface of the T cells.

B7-H1 can be useful as an augmenter of immune responses (e.g., helper T cell and antibody responses) both in vivo and in vitro. Furthermore, in light of (a) its ability to selectively enhance IL-10 production, (b) its ability to enhance apoptosis, and (c) its expression in placenta and lung, both organs normally protected from unneeded cellular-mediated immune and inflammatory responses, B7-H1 can be useful in controlling pathologic cell-mediated conditions (e.g., those induced by infectious agents such *Mycobacterium tuberculosis* or *M leprae*) or other pathologic cell-mediated responses such as those involved in autoimmune diseases (e.g., rheumatoid arthritis (RA), multiple sclerosis (MS), or insulin-dependent diabetes mellitus (IDDM)).

B7-H1 Nucleic Acid Molecules

The B7-H1 nucleic acid molecules of the invention can be cDNA, genomic DNA, synthetic DNA, or RNA, and can be double-stranded or single-stranded (i.e., either a sense or an antisense strand). Segments of these molecules are also considered within the scope of the invention, and can be produced by, for example; the polymerase chain reaction (PCR) or generated by treatment with one or more restriction endonucleases. A ribonucleic acid (RNA) molecule can be produced by in vitro transcription. Preferably, the nucleic acid molecules encode polypeptides that, regardless of length, are soluble under normal physiological conditions the membrane forms would not be soluble.

The nucleic acid molecules of the invention can contain naturally occurring sequences, or sequences that differ from those that occur naturally, but, due to the degeneracy of the genetic code, encode the same polypeptide (for example, the polypeptides with SEQ ID NOS:1 and 3). In addition, these nucleic acid molecules are not limited to coding sequences, e.g., they can include some or all of the non-coding sequences that lie upstream or downstream from a coding sequence. They include, for example, the nucleic acid molecule with SEQ ID NO:5.

The nucleic acid molecules of the invention can be synthesized (for example, by phosphoramidite-based synthesis) or obtained from a biological cell, such as the cell of a mammal. Thus, the nucleic acids can be those of a human, non-human primate (e.g., monkey) mouse, rat, guinea pig, cow, sheep, horse, pig, rabbit, dog, or cat.

In addition, the isolated nucleic acid molecules of the invention encompass segments that are not found as such in the natural state. Thus, the invention encompasses recombinant nucleic acid molecules, (for example, isolated nucleic acid molecules encoding hB7-H1 or mB7-H1) incorporated into a vector (for example, a plasmid or viral vector) or into the genome of a heterologous cell (or the genome of a homologous cell, at a position other than the natural chromosomal location). Recombinant nucleic acid molecules and uses therefor are discussed further below.

Certain nucleic acid molecules of the invention are antisense molecules or are transcribed into antisense molecules. These can be used, for example, to down-regulate translation of B7-H1 mRNA within a cell.

Techniques associated with detection or regulation of genes are well known to skilled artisans and such techniques can be used to diagnose and/or treat disorders associated with aberrant B7-H1 expression. Nucleic acid molecules of the invention are discussed further below in the context of their therapeutic utility.

A B7-H1 family gene or protein can be identified based on its similarity to the relevant B7-H1 gene or protein, respectively. For example, the identification can be based on sequence identity. The invention features isolated nucleic acid molecules which are at least 50% (or 55%, 65%, 75%, 85%, 95%, or 98%) identical to: (a) a nucleic acid molecule that encodes the polypeptide of SEQ ID NO:1 or 3; (b) the nucleotide sequence of SEQ ID NO:2 or 4; or (c) a nucleic acid molecule which includes a segment of at least 30 (e.g., at least 50, 60, 100, 125, 150, 175, 200, 250, 300, 325, 350, 375, 400, 425, 450, 500, 550, 600, 650, 700, 800, or 865) nucleotides of SEQ ID NO:2 or SEQ ID NO:4.

The determination of percent identity between two sequences is accomplished using the mathematical algorithm of Karlin and Altschul, *Proc. Natl. Acad. Sci. USA* 90, 5873-5877, 1993. Such an algorithm is incorporated into the BLASTN and BLASTP programs of Altschul et al. (1990) *J. Mol. Biol.* 215, 403-410. BLAST nucleotide searches are performed with the BLASTN program, score=100, wordlength=12 to obtain nucleotide sequences homologous to B7-H1-encoding nucleic acids. BLAST protein searches are performed with the BLASTP program, score=50, wordlength=3 to obtain amino acid sequences homologous to B7-H1. To obtain gapped alignments for comparative purposes, Gapped BLAST is utilized as described in Altschul et al. (1997) *Nucleic Acids Res.* 25, 3389-3402. When utilizing BLAST and Gapped BLAST programs, the default parameters of the respective programs (e.g.,) (BLAST and NBLAST) are used (See http://www.ncbi.nlm.nih.gov).

Hybridization can also be used as a measure of homology between two nucleic acid sequences. A B7-H1-encoding nucleic acid sequence, or a portion thereof, can be used as hybridization probe according to standard hybridization techniques. The hybridization of a B7-H1 probe to DNA from a test source (e.g., a mammalian cell) is an indication of the presence of B7-H1 DNA in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C., followed by one or more washes in 1×SSC, 0.1% SDS at 50-60° C. Highly stringent conditions are defined as equivalent to hybridization in 6× sodium chloride/sodium citrate (SSC) at 45° C., followed by one or more washes in 0.2×SSC, 0.1% SDS at 50-65° C.

The invention also encompasses: (a) vectors that contain any of the foregoing B7-H1-related coding sequences and/or their complements (that is, "antisense" sequence); (b) expression vectors that contain any of the foregoing B7-H1-related coding sequences operatively associated with any transcriptional/translational regulatory elements (examples of which are given below) necessary to direct expression of the coding sequences; (c) expression vectors containing, in addition to sequences encoding a B7-H1 polypeptide, nucleic acid sequences that are unrelated to nucleic acid sequences encoding B7-H1, such as molecules encoding a reporter, marker, or a signal peptide, e.g., fused to B7-H1; and (d) genetically engineered host cells that contain any of the foregoing expression vectors and thereby express the nucleic acid molecules of the invention.

Recombinant nucleic acid molecules can contain a sequence encoding hB7-H1 or mB7-H1, or B7-H1 having an heterologous signal sequence. The full length B7-H1 polypeptide, a domain of B7-H1, or a fragment thereof may be fused to additional polypeptides, as described below. Similarly, the nucleic acid molecules of the invention can encode the mature form of B7-H1 or a form that includes an exogenous polypeptide which facilitates secretion.

The transcriptional/translational regulatory elements referred to above and which are further described below, include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences, for example, sequences that function as a marker or reporter. Examples of marker or reporter genes include (β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, additional sequences that can serve the function of a marker or reporter. Generally, the hybrid polypeptide will include a first portion and a second portion; the first portion being a B7-H1 polypeptide and the second portion being, for example, the reporter described above or an Ig constant region or part of an Ig constant region, e.g., the CH2 and CH3 domains of IgG2a heavy chain.

The expression systems that may be used for purposes of the invention include, but are not limited to, microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, *Saccharomyces* and *Pichia*) transformed with recombinant yeast expression vectors containing the nucleic acid molecules of the invention (preferably containing the nucleic acid sequence encoding B7-H1 (contained within SEQ ID NOS:1 or 3); insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing B7-H1 nucleotide sequences; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal, transfected with a plasmid vector or infected with a viral vector.

Polypeptides and Polypeptide Fragments

The polypeptides of the invention include hB7-H1, mB7-H1, and functional fragments of these polypeptides. The polypeptides embraced by the invention also include fusion proteins which contain either full-length B7-H1 or a functional fragment of it fused to unrelated amino acid sequence. The unrelated sequences can be additional functional domains or signal peptides. Signal peptides are described in greater detail and exemplified below. The polypeptides can be any of those described above but with one or more (e.g., one, two, three, four, five, six, seven, eight, nine, 10, 12, 14, 17, 20, 25, 30, 35, 40, 50, 60, 70, 80, 90, 100 or more) conservative substitutions.

The polypeptides can be purified from natural sources (e.g., blood, serum plasma, tissues or cells such as T cells or any cell that naturally produces B7-H1). Smaller peptides (less than 50 amino acids long) can also be conveniently synthesized by standard chemical means. In addition, both polypeptides and peptides can be produced by standard in vitro recombinant DNA techniques and in vivo recombination/genetic recombination (e.g., transgenesis), using the nucleotide sequences encoding the appropriate polypeptides or peptides. Methods well known to those skilled in the art can be used to construct expression vectors containing relevant coding sequences and appropriate transcriptional translational control signals. See for example, the. techniques described in Sambrook et al., Molecular Cloning: A Laboratory Manual (2nd Ed.) [Cold Spring Harbor Laboratory, N.Y., 1989], and Ausubel et al., Current Protocols in Molecular Biology, [Green Publishing Associates and Wiley Interscience, N.Y., 1989].

Polypeptides and fragments of the invention also include those described above, but modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or noncovalently coupled to pharmaceutically acceptable "carrier" proteins prior to administration.

Also of interest are peptidomimetic compounds that are designed based upon the amino acid sequences of the functional peptide fragments. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to co-stimulate T cells in a manner qualitatively identical to that of the B7-H1 functional peptide fragment from which the peptidomimetic was derived. Peptidomimetic compounds can have additional characteristics that enhance their therapeutic utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Methods of Co-Stimulating a T Cell

The methods of the invention involve contacting a T cell with a B7-H1 polypeptide of the invention, or a functional fragment thereof, in order to co-stimulate the T cell. Such polypeptides or functional fragments can have amino acid sequences identical to wild-type sequences or they can contain one or more (e.g., one, two, three, four, five, six, seven, eight, nine, 10, 12, 14, 17, 20, 25, 30, 35, 40, 50, 60, 70, 80, 90, 100 or more) conservative substitutions. The contacting can occur before, during, or after activation of the T cell. Contacting of the T cell with the B7-H1 polypeptide will preferably be at substantially the same time as activation. Activation can be, for example, by exposing the T cell to an antibody that binds to the TCR or one of the polypeptides of the CD3 complex that is physically associated with the TCR. Alternatively, the T cell can be exposed to either an alloantigen (e.g., a MHC alloantigen) on, for example, an antigen presenting cell (APC) (e.g., a dendritic cell, a macrophage, a monocyte, or a B cell) or an antigenic peptide produced by processing of a protein antigen by any of the above APC and presented to the T cell by MHC molecules on the surface of the APC. The T cell can be a CD4+ T cell or a CD8+ T cell. The B7-H1 molecule can be added to the solution containing the cells, or it can be expressed on the surface of an APC, e.g., an APC presenting an alloantigen or an antigen peptide bound to an MHC molecule. Alternatively, if the activation is in vitro, the B7-H1 molecule can be bound to the floor of a the relevant culture vessel, e.g. a well of a plastic microtiter plate.

The methods can be performed in vitro, in vivo, or ex vivo. In vitro application of B7-H1 can be useful, for example, in basic scientific studies of immune mechanisms or for production of activated T cells for use in either studies on T cell function or, for example, passive immunotherapy. Furthermore, B7-H1 could be added to in vitro assays (e.g., in T cell proliferation assays) designed to test for immunity to an antigen of interest in a subject from which the T cells were obtained. Addition of B7-H1 to such assays would be expected to result in a more potent, and therefore more readily detectable, in vitro response. However, the methods of the invention will preferably be in vivo or ex vivo (see below).

The B7-H1 proteins and variants thereof are generally useful as immune response-stimulating therapeutics. For example, the polypeptides of the invention can be used for treatment of disease conditions characterized by immunosuppression: e.g., cancer, AIDS or AIDS-related complex, other virally or environmentally-induced conditions, and certain congenital immune deficiencies. The compounds may also be employed to increase immune function that has been impaired by the use of radiotherapy of immunosuppressive drugs such as certain chemotherapeutic agents, and therefore are particularly useful when given in conjunction with such drugs or radiotherapy. In addition, in view of the ability of B7-H1 to co-stimulate the production of especially high levels of IL-10, B7-H1 molecules can be used to treat conditions involving cellular immune responses, e.g., inflammatory conditions, e.g., those induced by infectious agents such *Mycobacterium tuberculosis* or *M leprae*, or other pathologic cell-mediated responses such as those involved in autoimmune diseases (e.g., rheumatoid arthritis (RA), multiple sclerosis (MS), or insulin-dependent diabetes mellitus (IDDM)).

These methods of the invention can be applied to a wide range of species, e.g., humans, non-human primates, horses, cattle, pigs, sheep, goats, dogs, cats, rabbits, guinea pigs, hamsters, rats, and mice.

In Vivo Approaches

In one in vivo approach, the B7-H1 polypeptide (or a functional fragment thereof) itself is administered to the subject. Generally, the compounds of the invention will be suspended in a pharmaceutically-acceptable carrier (e.g., physiological saline) and administered orally or by intravenous infusion, or injected subcutaneously, intramuscularly, intraperitoneally, intrarectally, intravaginally, intranasally, intragastrically, intratracheally, or intrapulmonarily. They are preferably delivered directly to an appropriate lymphoid tissue (e.g. spleen, lymph node, or mucosal-associated lymphoid tissue (MALT)). The dosage required depends on the choice of the route of administration, the nature of the formulation, the nature of the patient's illness, the subject's size, weight, surface area, age, and sex, other drugs being administered, and the judgment of the attending physician. Suitable dosages are in the range of 0.01-100.0 µg/kg. Wide variations in the needed dosage are to be expected in view of the variety of polypeptides and fragments available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2- or 3-, 4-, 6-, 8-, 10-, 20-, 50-,100-, 150-, or more fold). Encapsulation of the polypeptide in a suitable delivery vehicle (e.g., polymeric microparticles or implantable devices) may increase the efficiency of delivery, particularly for oral delivery.

Alternatively, a polynucleotide containing a nucleic acid sequence encoding the B7-H1 polypeptide or functional fragment can be delivered to an appropriate cell of the animal. Expression of the coding sequence will preferably be directed to lymphoid tissue of the subject by, for example, delivery of the polynucleotide to the lymphoid tissue. This can be achieved by, for example, the use of a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 µm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 µm and preferably larger than 20 µm.

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), *J. Mol. Med.* 73, 479]. Alternatively, lymphoid tissue-specific targeting can be achieved by the use of lymphoid tissue-specific transcriptional regulatory elements (TRE) such as a B lymphocyte, T lymphocyte, or dendritic cell specific TRE. Lymphoid tissue specific TRE are known [Thompson et al. (1992), *Mol. Cell. Biol.* 12, 1043-1053; Todd et al. (1993), *J. Exp. Med.* 177, 1663-1674; Penix et al. (1993), *J. Exp. Med.* 178, 1483-1496]. Delivery of "naked DNA" (i.e., without a delivery vehicle) to an intramuscular, intradermal, or subcutaneous site, is another means to achieve in vivo expression.

In the relevant polynucleotides (e.g., expression vectors) the nucleic acid sequence encoding the B7-H1 polypeptide or functional fragment of interest with an initiator methionine and optionally a targeting sequence is operatively linked to a promoter or enhancer-promoter combination.

Short amino acid sequences can act as signals to direct proteins to specific intracellular compartments. For example, hydrophobic signal peptides (e.g., MAISGVPVLGFFIIAV-LMSAQESWA (SEQ ID NO:6)) are found at the amino terminus of proteins destined for the ER. While the sequence KFERQ (SEQ ID NO:7) (and other closely related sequences) is known to target intracellular polypeptides to lysosomes, other sequences (e.g., MDDQRDLISNNEQLP (SEQ ID NO:8) direct polypeptides to endosomes. In addition, the peptide sequence KDEL (SEQ ID NO:9) has been shown to act as a retention signal for the ER. Each of these signal peptides, or a combination thereof, can be used to traffic the B7-H1 polypeptides or functional fragments of the invention as desired. DNAs encoding the B7-H1 polypeptides or functional fragments containing targeting signals will be generated by PCR or other standard genetic engineering or synthetic techniques.

A promoter is a TRE composed of a region of a DNA molecule, typically within 100 basepairs upstream of the point at which transcription starts. Enhancers provide expression specificity in terms of time, location, and level. Unlike a promoter, an enhancer can function when located at variable distances from the transcription site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles which are suitable for administration to a human, e.g., physiological saline. A therapeutically effective amount is an amount of the polynucleotide which is capable of producing a medically desirable result (e.g., an enhanced T cell response) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

Ex Vivo Approaches

Peripheral blood mononuclear cells (PBMC) can be withdrawn from the patient or a suitable donor and exposed ex vivo to an activating stimulus (see above) and a B7-H1 polypeptide or polypeptide fragment (whether in soluble form or attached to a sold support by standard methodologies). The PBMC containing highly activated T cells are then introduced into the same or a different patient.

An alternative ex vivo strategy can involve transfecting or transducing cells obtained from the subject with a polynucleotide encoding an B7-H1 polypeptide or functional fragment-encoding nucleic acid sequences described above. The transfected or transduced cells are then returned to the subject. While such cells would preferably be hemopoietic cells (e.g., bone marrow cells, macrophages, monocytes, dendritic cells, or B cells) they could also be any of a wide range of types including, without limitation, fibroblasts, epithelial cells, endothelial cells, keratinocytes, or muscle cells in which they act as a source of the B7-H1 polypeptide or functional fragment for as long as they survive in the subject. The use of hemopoietic cells, that include the above APC, would be particularly advantageous in that such cells would be expected to home to, among others, lymphoid tissue (e.g., lymph nodes or spleen) and thus the B7-H1 polypeptide or functional fragment would be produced in high concentration at the site where they exert their effect, i.e., enhancement of an immune response. In addition, if APC are used, the APC expressing the exogenous B7-H1 molecule can be the same APC that presents an alloantigen or antigenic peptide to the relevant T cell.

The B7-H1 can be secreted by the APC or expressed on its surface. Prior to returning the recombinant APC to the patient, they can optionally be exposed to sources of antigens or antigenic peptides of interest, e.g., those of tumors, infectious microorganisms, or autoantigens. The same genetic constructs and trafficking sequences described for the in vivo approach can be used for this ex vivo strategy. Furthermore, tumor cells, preferably obtained from a patient, can be transfected or transformed by a vector encoding a B7-H1 polypeptide or functional fragment thereof. The tumor cells, preferably treated with an agent (e.g., ionizing irradiation) that ablates their proliferative capacity, are then returned to the patient where, due to their expression of the exogenous B7-H1 (on their cell surface or by secretion), they can stimulate enhanced tumoricidal T cell immune responses. It is understood that the tumor cells which, after transfection or transformation, are injected into the patient, can also have been originally obtained from an individual other than the patient.

The ex vivo methods include the steps of harvesting cells from a subject, culturing the cells, transducing them with an expression vector, and maintaining the cells under conditions suitable for expression of the B7-H1 polypeptide or functional fragment. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced are then selected, for example, for expression of the coding sequence or of a drug resistance gene. The cells may then be lethally irradiated (if desired) and injected or implanted into the patient.

Methods of Screening for Compounds that Inhibit or Enhance Immune Responses.

The invention provides methods for testing compounds (small molecules or macromolecules) that inhibit or enhance an immune response. Such a method can involve, e.g., culturing a B7-H1 polypeptide of the invention (or a functional fragment thereof) with T cells in the presence of a T cell stimulus (see above). Useful B7-H1 polypeptides include those with amino acid sequences identical to wild-type sequences or they can contain one or more (e.g., one, two, three, four, five, six, seven, eight, nine, 10, 12, 14, 17, 20, 25, 30, 35, 40, 50, 60, 70, 80, 90, 100 or more) conservative substitutions. The B7-H1 polypeptide can be in solution or membrane bound (e.g., expressed on the surface of the T cells) and it can be natural or recombinant. Compounds that inhibit the T cell response will likely be compounds that inhibit an immune response while those that enhance the T cell response will likely be compounds that enhance an immune response.

The invention also relates to using B7-H1 or functional fragments thereof to screen for immunomodulatory compounds that can interact with B7-H1. One of skill in the art would know how to use standard molecular modeling or other techniques to identify small molecules that would bind to T cell interactive sites of B7-H1. One such example is provided in Broughton (1997) *Curr. Opin. Chem. Biol.* 1, 392-398.

A candidate compound whose presence requires at least 1.5-fold (e.g., 2-fold, 4-fold, 6-fold, 10-fold, 150-fold, 1000-fold, 10,000-fold, or 100,000-fold) more B7-H1 in order to achieve a defined arbitrary level of T cell activation than in the absence of the compound can be useful for inhibiting an immune response. On the other hand, a candidate compound whose presence requires at least 1.5 fold (e.g., 2-fold, 4-fold, 6-fold, 10-fold, 100-fold, 1000-fold, 10,000 fold, or 100,000-fold) less B7-H1 to achieve a defined arbitrary level of T cell activation than in the absence of the compound can be useful for enhancing an immune response. Compounds capable of interfering with or modulating B7-H1 function are good candidates for immunosuppressive immunoregulatory agents, e.g., to modulate an autoimmune response or suppress allogeneic or xenogeneic graft rejection.

B7-H1 Antibodies

The invention features antibodies that bind to either or both of the B7-H1 polypeptides or fragments of such polypeptides. Such antibodies can be polyclonal antibodies present in the serum or plasma of animals (e.g., mice, rabbits, rats, guinea pigs, sheep, horses, goats, cows, or pigs) which have been immunized with the relevant B7-H1 polypeptide or peptide fragment using methods, and optionally adjuvants, known in the art. Such polyclonal antibodies can be isolated from serum or plasma by methods known in the art. Monoclonal antibodies that bind to the above polypeptides or fragments are also embodied by the invention. Methods of making and screening monoclonal antibodies are well known in the art.

Once the desired antibody-producing hybridoma has been selected and cloned, the resultant antibody can be produced in a number of methods known in the art. For example, the hybridoma can be cultured in vitro in a suitable medium for a suitable length of time, followed by the recovery of the desired antibody from the supernatant. The length of time and medium are known or can be readily determined.

Additionally, recombinant antibodies specific for B7-H1, such as chimeric and humanized monoclonal antibodies comprising both human and non-human portions, are within the scope of the invention. Such chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) *Science* 240, 1041-43; Liu et al. (1987) *J. Immunol.* 139, 3521-26; Sun et al. (1987) *PNAS* 84, 214-18; Nishimura et al. (1987) *Canc. Res.* 47, 999-1005; Wood et al. (1985) *Nature* 314, 446-49; Shaw et al. (1988) *J. Natl. Cancer Inst.* 80, 1553-59; Morrison, (1985) *Science* 229, 1202-07; Oi et al. (1986) *BioTechniques* 4, 214; Winter, U.S. Pat. No. 5,225,539; Jones et al. (1986) *Nature* 321, 522-25; Veroeyan et al. (1988) *Science* 239, 1534; and Beidler et al. (1988) *J. Immunol.* 141, 4053-60.

Also included within the scope of the invention are antibody fragments and derivatives which contain at least the functional portion of the antigen binding domain of an antibody that binds specifically to B7-H1. Antibody fragments that contain the binding domain of the molecule can be generated by known techniques. For example, such fragments include, but are not limited to: $F(ab')_2$ fragments which can be produced by pepsin digestion of antibody molecules; Fab fragments which can be generated by reducing the disulfide bridges of $F(ab')_2$ fragments; and Fab fragments which can be generated by treating antibody molecules with papain and a reducing agent. See, e.g., National Institutes of Health, 1 *Current Protocols In Immunology*, Coligan et al., ed. 2.8, 2.10 (Wiley Interscience, 1991). Antibody fragments also include Fv (e.g., single chain Fv (scFv)) fragments, i.e., antibody products in which there are no constant region amino acid residues. Such fragments can be produced, for example, as described in U.S. Pat. No. 4,642,334, which is incorporated herein by reference in its entirety.

The following examples are meant to illustrate, not limit, the invention.

EXAMPLES

Example 1

Materials and Methods

Cloning of hB7-H1 cDNA and construction of Ig fusion proteins. The 5' and 3' ends of hB7-H1 cDNA were amplified by PCR from a human placenta cDNA library synthesized by SMART PCR cDNA synthesis kit (Clontech, Palo Alto, Calif.). The primer pairs used for the PCR were derived from the placenta library plasmid and from the expressed sequence tag (EST) clone AA292201. A cDNA clone that included an orf encoding hB7-H1 of hB7-H1 cDNA was amplified by PCR from the same cDNA library by specific primers and cloned into the pcDNA3 vector (Invitrogen, Carlsbad, Calif.) and sequenced. The amino acid sequences of hB7-H1, B7-1 and B7-2 were analyzed using the ClustalW algorithm with BLOSUM 30 matrix (MacVector, Oxford Molecular Group). The hB7-H1Ig fusion protein was prepared by fusing the extracellular domain of hB7H-1 to the CH2-CH3 domain of mouse IgG2a in the expression plasmid pmIgV and the resulting construct was transfected into CHO cells. An analogous method was also used for preparation of B7-1Ig, CTLA4Ig and ICOSIg fusion proteins. The fusion proteins were purified from culture supernatants by passage over a Protein G-Sepharose affinity columns (Pharmacia, Uppsala, Sweden) and the purified fusion proteins were dialyzed into endotoxin-free PBS.

DNA transfection. Plasmids containing nucleic acid sequences encoding full length hB7-H1 (pcDNA3-hB7-H1), B7-1 (pCDM8-B7.1) or control parental vectors without coding sequences were transfected into 293 cells or COS cells by calcium phosphate or DEAE-Dextran transfection (Promega, Madison, Wis.). After 48 hours of incubation, the expression levels of hB7-H1 or B7-1 on transfectants were determined by fluorescence flow cytometry (FFC) with an antiserum specific for hB7-H1 or anti-B7-1 monoclonal antibody (mAb) (PharMingen), respectively.

Mice and cell lines. Female C57BL/6 (B6), DBA/2, and BALB/c mice were purchased from the National Cancer Institute (Frederick, Md.). CD28$^{-/-}$ mice with a B6 genetic background were kindly provided by Dr. Moses Rodrigues (Department of Immunology, Mayo Clinic, Rochester, Minn.). P815 mastocytoma, L1210 lymphoma, EL4 mouse T-cell lymphoma and 293 human kidney epithelial cells were purchased from the American Type Culture Collection (Manassas, Va.). Cell lines were maintained in a complete medium containing RPMI-1640 (Life Technologies, Rockville, Md.) supplemented with 10% fetal bovine serum (FBS) (HyClone, Logan, Utah), 25 mM HEPES, penicillin G (100 U/ml) and streptomycin sulfate (100 µg/ml).

T-cell and cytokine assays. For human T cell studies, PBMC were isolated from the blood of healthy human volunteer donors by Ficoll-Hypaque gradient centrifugation. The PBMC were passed through a nylon wool column to obtain purified T cells (~85% of CD3$^+$ cells), or were subjected to further purification (>95% of CD3$^+$ cells) using an anti-CD4/8 MACS magnetic bead system (Miltenyi Biotec, Germany). For co-stimulation assays, purified T cells at a concentration of 1×10$^5$ cells/well were cultured in triplicate in 96-well flat-bottomed microtiter tissue culture plates that were pre-coated overnight with antibody specific for human CD3 (HIT3a, PharMingen, Palo Alto, Calif.) and either hB7-H1Ig (5 µg/ml) or control Ig (purified mouse IgG2a or murine 4-1BBIg fusion protein). In some experiments, the microtiter wells were coated with only antibody specific for CD3 and B7-1 or hB7-H1-transfected COS cells were used (10$^4$ cells/well) as a source of the co-stimulatory molecules. To measure cytokine production, supernatants were collected at 24, 48 and 72 hours after initiation of the cultures and the concentrations of IL-2, IL-4, IFN-γ and IL-10 were determined by sandwich ELISA (PharMingen) according to the manufacturer's instructions. Wells containing B7-1Ig or antibody specific for human CD28 (CD28.2, PharMingen) were included for comparison or as a positive control, respectively. T cell proliferation was determined by the addition of 1.0 µCi [$^3$H]-thymidine per well on day 2 followed by at least 18 hours of additional culture. Incorporated [$^3$H]-thymidine was determined using a MicroBeta TriLux liquid scintillation counter (Wallac, Finland).

For mixed lymphocyte reaction (MLR) assays, purified human T cells (2×10$^5$ cells/well) were co-cultured in triplicate with allogeneic human PBMC (4000 Rad-irradiated) at 2×10$^5$ cells/well in the presence of soluble hB7-H1Ig or control Ig. Four days later, T cell proliferation was determined by [$^3$H]-thymidine incorporation. Neutralizing mAb specific for human IL-2 (Clone MQ1-17H12, PharMingen) was added at 8 µg/ml in the beginning of T cell cultures. Polymyxin B (10 µg/ml) was also included in the assays of cell proliferation and cytokine secretion to completely neutralize any contaminating endotoxin.

For mouse T cell studies, T cells were purified by passing lymph node or spleen cells through a nylon wool column. CD4+ or CD8+ T cells were positively selected by magnetic sorting using FITC-conjugated mAb against CD4 or CD8 and microbeads coated with antibody specific for fluorescein isothiocyanate (FITC) (MiltenyiBiotec, Auburn, Calif.) according to the manufacturer's instructions. The purity of isolated CD4$^+$ and CD8$^+$ T cells was >95% by FFC with mAb specific for mouse CD4 and CD8, respectively. Purified T cells at 2×10$^6$/ml from mouse spleens were cultured in 96-well plates that were pre-coated with mAb specific for mouse CD3 in the presence of mB7-H1Ig or control mouse IgG2a ("control Ig") also coated onto the culture well bottoms. mAb specific for mouse CD28 (2.5 µg/ml) was used in soluble form as a positive control co-stimulator. Proliferation of T cells was determined by incorporation of [$^3$H]-thymidine (1.0 µCi/well) added 15 h before harvesting of the 3-day cultures. [$^3$H]-thymidine incorporation was determined by a MicroBeta TriLux liquid scintillation counter (Wallac, Turku, Finland). To detect cytokines, supernatants were collected between 18-72 h of culture and the concentrations of IFN-γ, IL-2, IL-10, IL-4, and GM-CSF were measured by sandwich ELISA following the manufacturer's (PharMingen) instructions.

Nucleic acid analysis. Northern blot analysis of human RNA was carried out using commercially available human multiple tissue Northern blot membranes (Clontech, Palo Alto, Calif.). Membranes were incubated in ExpressHyb hybridization solution (Clontech) for 30 min at 68° C. The random-primed cDNA probe was full length hB7-H1 encoding cDNA (870 bp) labeled using [$^{32}$P]-dCTP. A $^{32}$P-labeled human β-actin cDNA probe (2.0 kb) was used as a control. Hybridization was carried out for 1 hr at 68° C., the membranes were washed 3 times in 2×SSC containing 0.05% SDS, and were then exposed at −80° C. to x-ray film.

Tissue distribution of mB7-H1 mRNA was carried out using commercially available multiple tissue mouse RNA dot blot membranes (Clontech) according to the manufacturer's instructions. The random-primed cDNA probe was full-length mB7-H1 encoding cDNA and was labeled using [$^{32}$P]-dCTP. The hybridization was performed for 16 h at 65° C.

After washing four times with 2×SSC containing 0.05% SDS, the membranes were exposed at −80° C. to x-ray films.

Antibodies and fusion proteins. Rabbit antibodies against mB7-H1 protein were prepared by Cocalico Biologicals (Reamstown, Pa.) by immunization of rabbits with a keyhole limpet hemocyanin (KLH)-conjugated hydrophilic peptide spanning amino acids 95-119 of mB7-H1 ("peptide 95-119") (GNAALQITDVKLQDAGVYCCIISYG) (SEQ ID NO:16). Polyclonal antibody was purified from rabbit serum using an affinity column containing insoluble matrix material conjugated with the peptide 95-119. Both ELISA and FFC analysis of COS cells transfected with an expression vector containing cDNA encoding mB7-H1 demonstrated that the polyclonal antibody bound specifically to mB7-H1. Purified mAb specific for mouse CD3 and mouse CD28 and FITC-conjugated mAb specific for mouse CD4, mouse CD8, and mouse CD40L, phycoerythrin (PE)-conjugated mAb specific for mouse CD3, mouse B220 and mouse Mac-1 were purchased from PharMingen (San Diego, Calif.). FITC-conjugated goat antibody specific for rabbit IgG was purchased from Southern Biotechnology Associates (Birmingham, Ala.). Purified rabbit IgG and hamster IgG were purchased from Rockland (Gilbertsville, Pa.).

To prepare the mB7-H1 1 g fusion protein, cDNA encoding the mB7-H1 extracellular domain was generated by RT-PCR using the sense primer 5'-CAGGAATTCACCATGAG-GATATTTGCTG-3' (SEQ ID NO:17) and the anti-sense primer 5'-CATCAGATCTATGTGAGTCCTGTTCTGTG-3' (SEQ ID NO:18) from mouse T cell mRNA. After digestion with EcoRI and BglII, the PCR products were fused to the CH2-CH3 domain of mouse IgG2a heavy chain in the expression plasmid pmIgV [Dong et al. (1999) *Nature Med.* 5, 1365-1369]. The resulting plasmid, pmB7-H1Ig, was transfected into CHO cells. Stably transfected cells were cultured in serum-free CHO media (Life Technologies). The mB7-H1Ig in the supernatants was purified using a protein G-Sepharose column (Pierce, Rockford, Ill.) and dialyzed into LPS-free PBS. The endotoxin concentration was less than 1 µg/mg of purified protein according to the *limulus amebocyte* lysate assays (CAPE COD, Woods Hole, Mass.). The mB7-1Ig fusion protein containing the extra cellular domain of mB7-1 fused to the CH2-CH3 domain of mouse IgG-2a heavy chain was prepared by an analogous method.

Fluorescence flow cytometry analysis. To prepare an antiserum specific for hB7-H1, mice were immunized with purified hB7-H1Ig emulsified in complete Freund's adjuvant (Sigma) and boosted three times with hB7-H1Ig in incomplete Freund's adjuvant. Serum was collected and the specificity was determined by ELISA and by FACS staining (1:1000 dilution) of hB7-H1 cDNA-transfected 293 cells or COS cells. Pre-injection mouse serum was used as a control.

To prepare activated human T and B cells, freshly isolated human PBMC ($10 \times 10^6$ cells/ml) were activated with 5 µg/ml of PHA (Sigma) or 10 µg/ml of LPS (Sigma), respectively. For preparation of activated monocytes, adherent PBMCs were cultured in 1,500 IU/ml of recombinant human IFN-γ (Biosource, Camarillo, Calif.) and 100 ng/ml of LPS. All cultures were harvested and analyzed at 48 hours. For direct immunofluorescence staining, T cells were incubated at 4° C. with 1 µg of either fluorescein-(FITC) or phycoerythrin-(PE) conjugated mAb for 30 min and analyzed by FACScan flow cytometry (Becton Dickinson, Mountain View, Calif.) with Cell Quest software (Becton Dickinson) as described previously. The mAb specific for CD3 (UCHT1), CD4 (RPA-T4), CD8 (RPA-T8), CD14 (M5E2), CD19 (B43), CD28 (CD28.2), CD80 (BB1) were purchased from PharMingen. For indirect immunofluorescence staining, cells were first incubated with anti-hB7-H1 antibody (1:1000), 5 µg of ICOSIg or CTLA4Ig at 4° C. After 30 min, the cells were washed and further incubated with FITC- (Biosource, Camarillo, Calif.) or PE-conjugated (Southern Biotechnology Associates, Inc., Birmingham, Ala.) goat anti-human or anti-mouse IgG F(ab')$_2$ for 30 min at 4° C. The human or mouse IgG1 protein (Sigma) or mouse 4-1BBIg (mouse 4-1BB extracellular domain fused with the Fc of human IgG1 or mouse IgG2a) was used as control Ig. In some experiments, Fc receptors were blocked by human or mouse Ig before incubation with FITC- or PE-conjugated mAbs.

For indirect immunofluorecence analysis of mouse cells, the cells were incubated with the antibodies at 4° C. for 30 min in the presence of blocking mAb specific for CD16/32 (Fc receptor) (Pharmingen). The cells were washed and further incubated with FITC-conjugated anti-rabbit IgG. The cells were then stained with PE-conjugated mAb specific for mouse CD3, mouse B220, or mouse Mac-1. Fluorescence was analyzed with a FACS Calibur flow cytometer and analyzed with Cell Quest software (Becton Dickinson, Mountain View, Calif.). To prepare activated mouse T cells, nylon-wool-purified mouse T cells (>75% CD3$^+$ cells) at a concentration of $2 \times 10^6$/ml were cultured with mAb specific for mouse CD28 (5 µg/ml) and mouse CD3 (5 µg/ml). For preparation of activated mouse B cells, mouse splenocytes were cultured with LPS (10 µg/ml; Sigma, St. Louis, Mo.). Mouse macrophages were obtained from the peritoneal cavities of mice which had been injected with thioglycoilate 7 days before. For activation, the mouse peritoneal exudate cells (PEC) were cultured with IFN-γ (10 U/ml) and LPS (100 ng/ml). All cultures were harvested and the cells analyzed at 48 h. To detect CD40L expression, CD4$^+$ T cells were purified by magnetic sorting (see above), cultured as indicated, and incubated with FITC-conjugated mAb to CD40L.

Cytotoxic T-lymphocyte (CTL) generation. To generate alloantigen-specific CTL activity in vitro, nylon wool purified T cells ($2.5 \times 10^6$/ml) from B6 splenocytes were stimulated in 24-well tissue culture plates with irradiated (10,000 rads) mock.P815, mB7-1$^+$ P815, or mB7-H1$^+$ P815 cells ($2.5 \times 10^5$/ml) for 5 days. After the 5-day stimulation, CTL activities against P815 (H-2$^d$) and EL4 (H-2$^b$) were measured in a standard $^{51}$Cr release assay [Chen et al. (1994) *J. Exp. Med.* 179, 523-532; Li et al. (1996) *J. Exp. Med.* 183, 639-644].

To generate tumor-specific CTL activity in vivo, DBA/2 mice were inoculated subcutaneously (s.c.) with $1 \times 10^6$ mock.P815, mB7-1$^+$ P815, or mB7-H1$^+$ P815 cells. The draining lymph nodes were removed 7-10 d after tumor injection and the suspended lymph node cells ($3 \times 10^6$/ml) were re-stimulated in 24 well tissue culture plates with wild type irradiated (10,000 rads) P815 cells ($3 \times 10^5$/ml) for 5 days. The cells were harvested and their CTL activity was measured in a standard $^{51}$Cr release assay against wild type P815 tumor target cells.

In vivo induction and assay of TNP-specific antibody. Trinitrophenol (TNP) conjugated to KLH (TNP-KLH; 100 µg/mouse) (Biosearch Technologies, Novato, Calif.) in phosphate buffered saline (PBS) was injected i.p. into B6 mice on day 0. On days 1 and 4, the mice were injected i.p. with 100 µg of control Ig, mB7-1Ig, or mB7-H1Ig. Sera were collected on days 7 and 14. To measure TNP-specific antibodies in the sera, 0.3 mg/ml TNP-BSA (Biosearch Technologies) was coated onto the well-bottoms of 96-well ELISA plates overnight at 4° C. Non-specific binding sites in the ELISA plates were blocked with 10% FBS in PBS for 90 min at room temperature. After extensive washing, samples (diluted by 1/200-1/2000 with PBS) were added and incubated for 2 h.

The plates were then washed and biotinylated rat antibodies specific for mouse IgM, IgG1, IgG2a, IgG2b, or IgG3 (PharMingen) were added to the wells. The plates were further incubated for 1 h at room temperature. After washing the plates, horseradish peroxidase (HRP)-conjugated streptavidin (Caltag Laboratories, Burlingame, Calif.) was added to the wells and the plates were incubated for 1 h at room temperature. The plates were washed and the solutions in all wells was measured. 3,3',5,5'-tetramethyl-benzidine substrate (Sigma) was added to the wells. The $OD_{450}$ for the solutions in all wells was measured.

T cell proliferation in response to KLH. B6 mice were immunized with 100 µg TNP-KLH in IFA s.c. or in PBS i.p. on day 0 and were injected i.p. with 100 µg of either mB7-H1Ig or control Ig on days 1 and 4. To detect T cell responses to KLH, draining lymph nodes and spleens were removed from immunized mice on day 7 and 14, respectively. Suspended lymph node or spleen cells were cultured with KLH at 1.56-100 µg/ml as indicated. T cell proliferation in response to KLH was determined by addition of 1 µCi/well [$^3$H]-thymidine 15 h before harvesting of the 3-day cultures. [$^3$H]-thymidine incorporation was measured with a MicroBeta TriLux liquid scintillation counter (Wallac).

Example 2

Molecular Cloning and Expression Pattern of the hB7-H1 Gene

A homology search of the human cDNA EST database using published human B7-1 and B7-2 amino acid sequences revealed an EST sequence (GeneBank #AA292201) encoding a homologue to human B7-1 and B7-2 molecules. The 5'- and 3'-sequences were obtained by several independent reverse transcriptase-coupled polymerase chain reactions (RT-PCR) from a human placenta cDNA library utilizing vector and EST sequences as primers. A 3,616 bp fragment that included the hB7-H1 encoding orf was cloned and sequenced (SEQ ID NO:5) (FIG. 1). The coding sequence for hB7-H1 (SEQ ID NO:2) spans nucleotides 72-951 of SEQ ID NO:5. The amino acid sequence of full-length hB7-H1 (SEQ ID NO:1) is shown in FIG. 2a. The extracellular domain of hB7-H1 has greater homology to B7-1 (20% amino acid identity) than to B7-2 (15%) (FIG. 2b) whereas its cytoplasmic domain is highly divergent from that of B7-1 and B7-2 based on analysis using the McVector 6.5 software. The open reading frame of the gene encodes a type I transmembrane protein of 290 amino acids consisting of a 22 amino acid signal peptide, Ig V-like domain, and Ig C-like domains, a hydrophobic transmembrane domain and a cytoplasmic tail of 30 amino acids (FIG. 2a). Four structural cysteines (labeled by stars in FIG. 2b), which are apparently involved in forming the disulfide bonds of the Ig V and Ig C domains are well conserved in all B7 members (FIG. 2b) [Fargeas, C. A. et al. (1995) *J. Exp. Med.* 182, 667-675; Bajorath, J. et al. (1994) *Protein Sci.* 3, 2148-50; Linsley, P. S. et al. (1994) *Immunity* 1, 793-801; Inaba, K. et al. (1994) *J. Exp. Med.* 180, 1849-60; Freeman, G. J. et al. (1995) *Immunity* 2, 523-532]. In addition, the tyrosine residue in B7-1 (at position 87) and in B7-2 (at position 82) of the Ig V-like domain is conserved in hB7-H1 (at position 81) (FIG. 2b).

Northern blot analysis revealed that expression of the hB7-H1 mRNA was abundant in heart, skeletal muscle, placenta and lung but was weak in thymus, spleen, kidney and liver (FIG. 3). The hB7-H1 mRNA was not detectable in brain, colon, small intestine and peripheral blood mononuclear cells (PBMC). In most of the tissues in which hB7-H1 mRNA was detectable, two transcripts of approximately 4.1 and 7.2 kb were found.

Figure 4A:
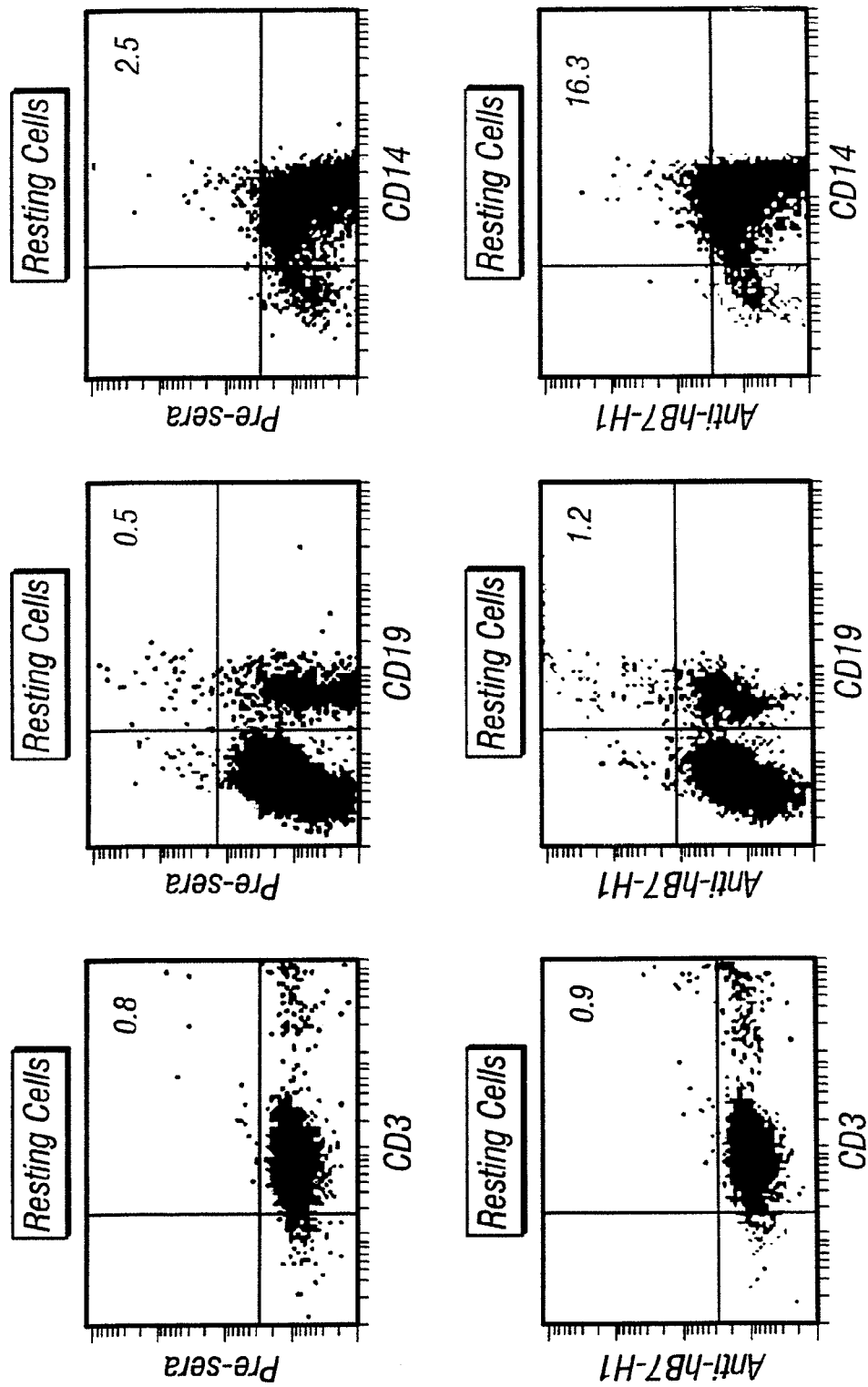
FIG. 4 is a series of two-dimensional fluorescence flow cytometry histograms showing cell surface expression of hB7-H1 on resting and activated CD3+ T cells, CD19+ B cells, and CD 14+ monocytes.
Figure 4B:
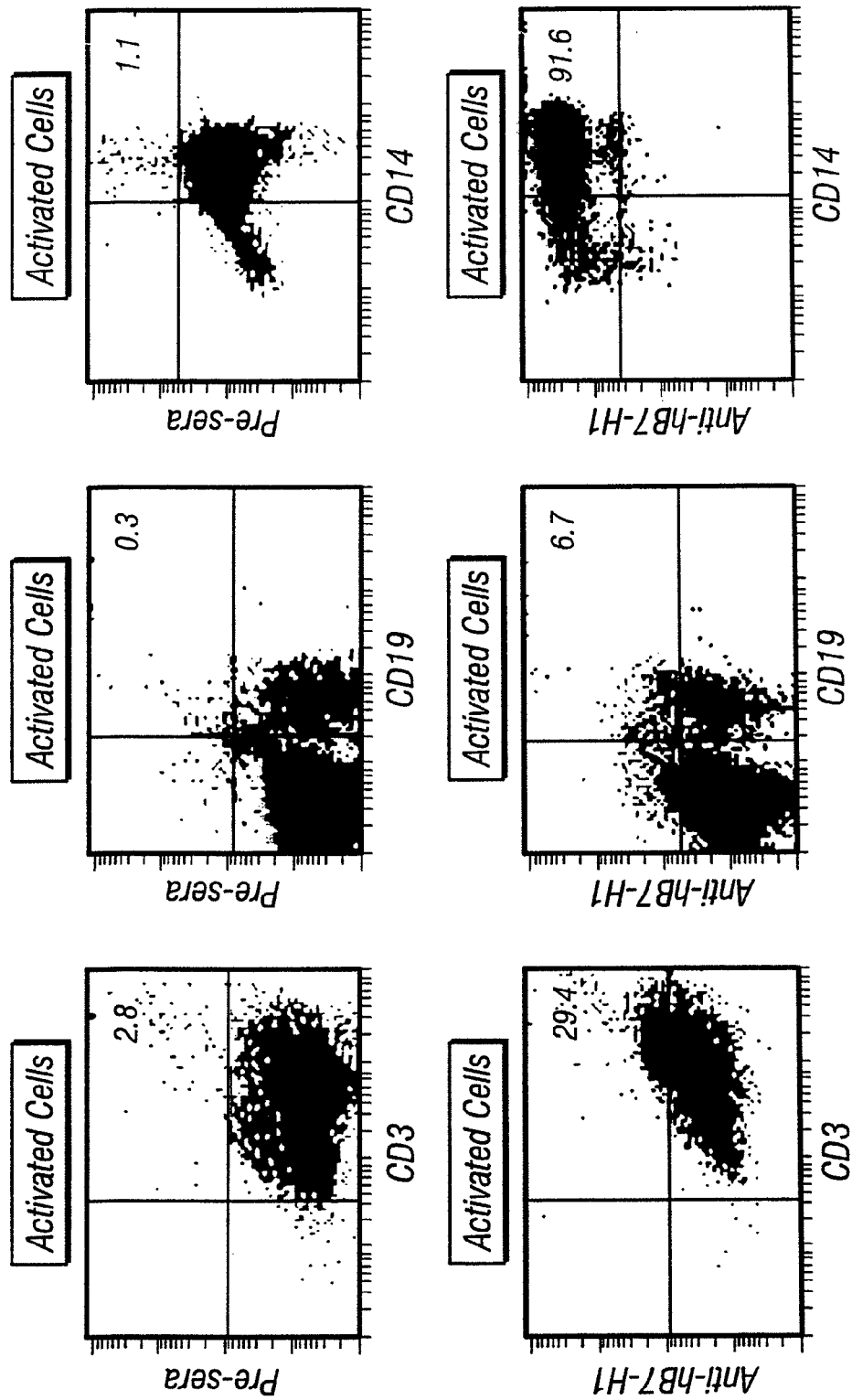

An expression plasmid containing the extracellular domain of hB7-H1 fused in frame with the Fc portion (CH2 and CH3-domains) of the mouse IgG2a was constructed. The resulting product, hB7-H1Ig fusion protein, was purified from the supernatants of CHO cells transfected with the plasmid and was used for immunization of the mice to prepare a hB7-H1-specific antiserum. Fluorescence flow cytometry analysis using the hB7-H1-specific antiserum showed that freshly isolated CD3+ T and CD 19+ B cells express negligible levels of hB7-H1 while a fraction (~16%) of CD14+ monocytes constitutively express hB7-H1. hB7-H1 can, however, be up-regulated by cell activation. Approximately 30% of PHA-treated CD3+ T cells and 90% of CD14+ monocytes (treated with IFN-γ and LPS) express hB7-H1. Only 6% of CD19+ B cells after LPS activation express hB7-H1 (FIG. 4). Confirmatory results were obtained by RT-PCR analysis.

Figure 5A:
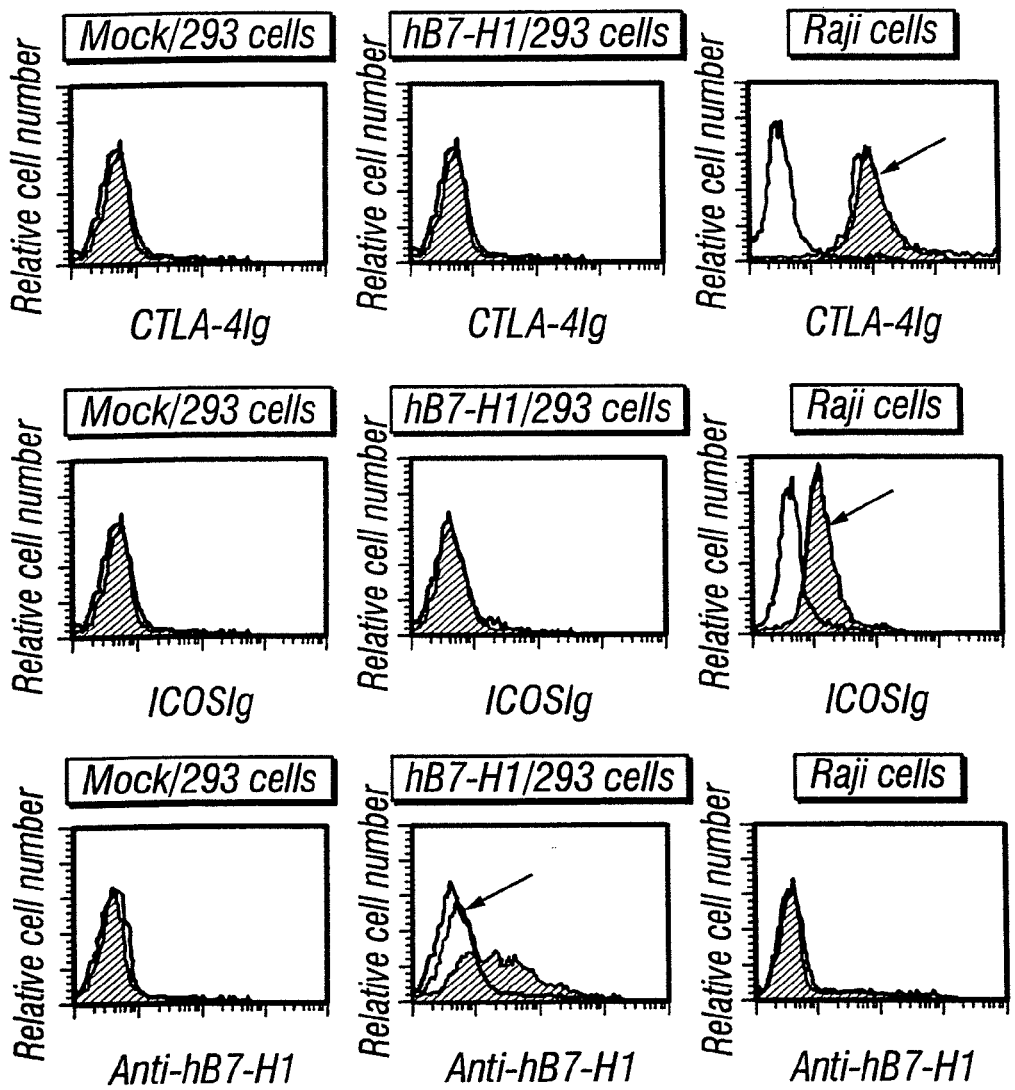
FIG. 5a is a series of fluorescence flow cytometry histograms showing binding of CTLA-4Ig, ICOSIg, and antibody specific for hB7-H1 to 293 cells transfected with either a control vector ("Mock/293 cells") or a vector containing a cDNA insert encoding hB7-H1 ("hB7-H1/293 cells"), or Raji cells.
Figure 5B:
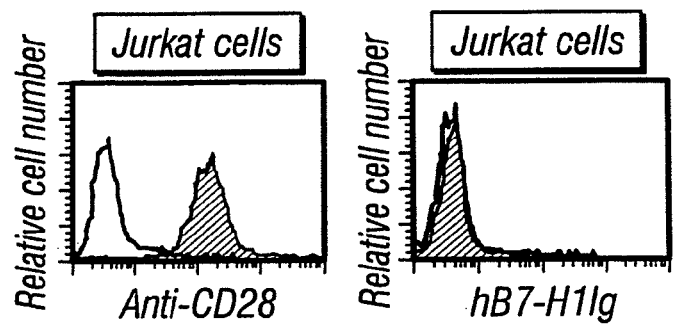
FIG. 5b is a series of fluorescence flow cytometry histograms showing the binding of hB7-H1Ig and antibody to CD28 to Jurkat cells.

Transfection of the plasmid pcDNA3-hB7-H1 into 293 cells (B7-H1/293 cells) led to the expression of hB7-H1 as detected by hB7-H1-specific antiserum (FIG. 5a). The binding of antibody was eliminated by the inclusion of soluble hB7-H1Ig in the staining mixture (FIG. 5a, arrow), thereby demonstrating specificity of the antiserum. Neither CTLA4Ig nor ICOSIg bound to hB7-H1/293 cells. Although both CTLA4Ig and ICOSIg bound to Raji cells, the binding was not blocked by the inclusion of hB7-H1Ig (FIG. 5a, arrows). Taken together with the observation that hB7-H1Ig did not bind to Jurkat cells (FIG. 5b, right panel), despite their constitutive expression of CD28 (FIG. 5b, left panel), the above results indicate that hB7-H1 is not a ligand for CD28, CTLA-4, or ICOS.

Example 3

Co-Stimulation of T Cell Proliferation by hB7-H1

Figure 6A:
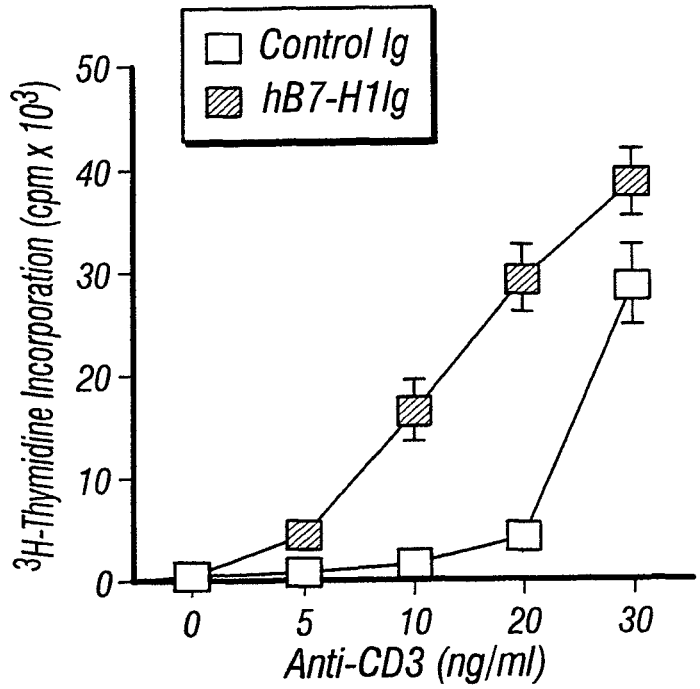
FIG. 6a is a line graph showing the ability of immobilized hB7-H1Ig to co-stimulate the proliferative response of human T cells to immobilized antibody specific for human CD3.
Figure 6B:
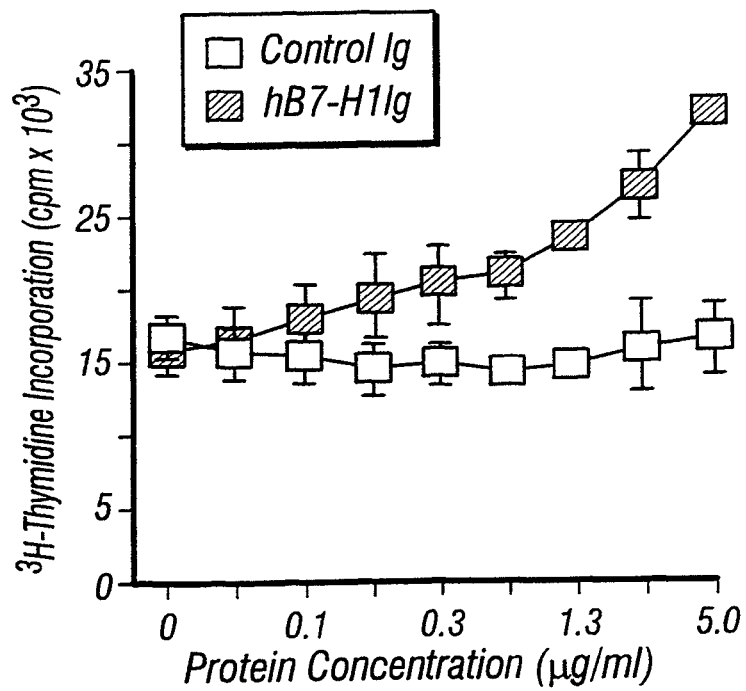
FIG. 6b is a line graph showing the ability of soluble hB7-H1Ig to co-stimulate the proliferative response of human T cells to irradiated allogeneic PBMC.

To assess whether hB7-H1 co-stimulates T-cell growth, T cells purified (>95% purity) from PBMC of healthy human donors were stimulated with hB7-H1Ig in the presence of suboptimal doses of mAb specific for human CD3. T cell proliferation in 3-day cultures was determined by incorporation of [$^3$H]-thymidine. hB7-H1Ig, immobilized on culture plates, enhanced T cell proliferation up to 10-fold compared to the control Ig in the presence of 5-20 ng/ml of mAb specific for human CD3, also immobilized on the culture plates. In the absence of mAb specific for human CD3, hB7-H1Ig at a concentration up to 5 µg/ml induced no T cell proliferation (FIG. 6a). If hB7-H1Ig was included in the cultures without immobilization, its co-stimulatory effect was significantly decreased. Consistent with this observation, the inclusion of soluble hB7-H1Ig at levels of 0.6-5 µg/ml in allogeneic MLR moderately (~2-fold) increased the proliferation of T cells (FIG. 6b). Thus, hB7-H1 can promote and co-stimulate proliferative responses of T cells to polyclonal T cell stimuli and to allogeneic antigens.

Example 4 hB7-H1 Co-Stimulation Preferentially Induces the Production of IL-10 and the Co-Stimulatory Effect Requires IL-2

Figure 7B:
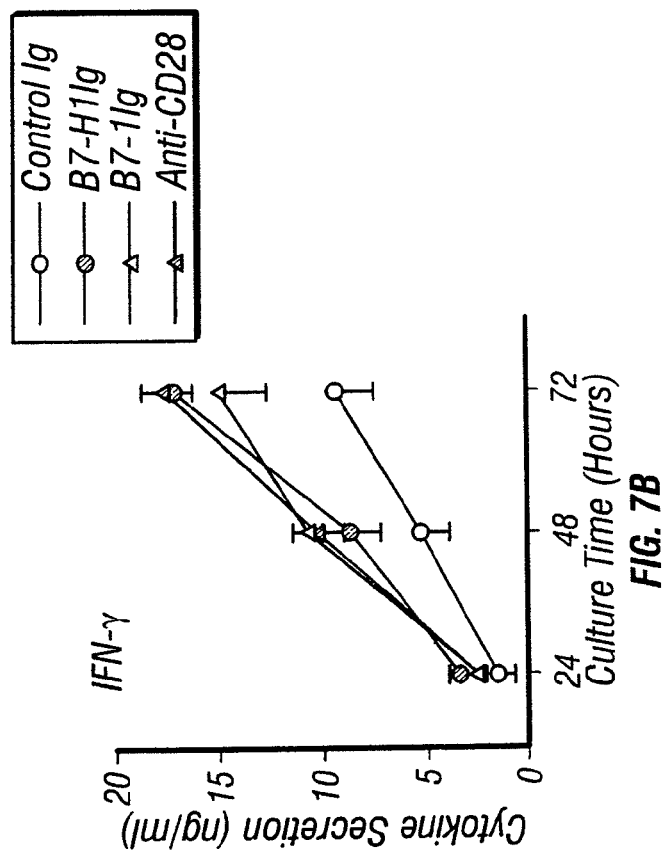
Figure 7A:
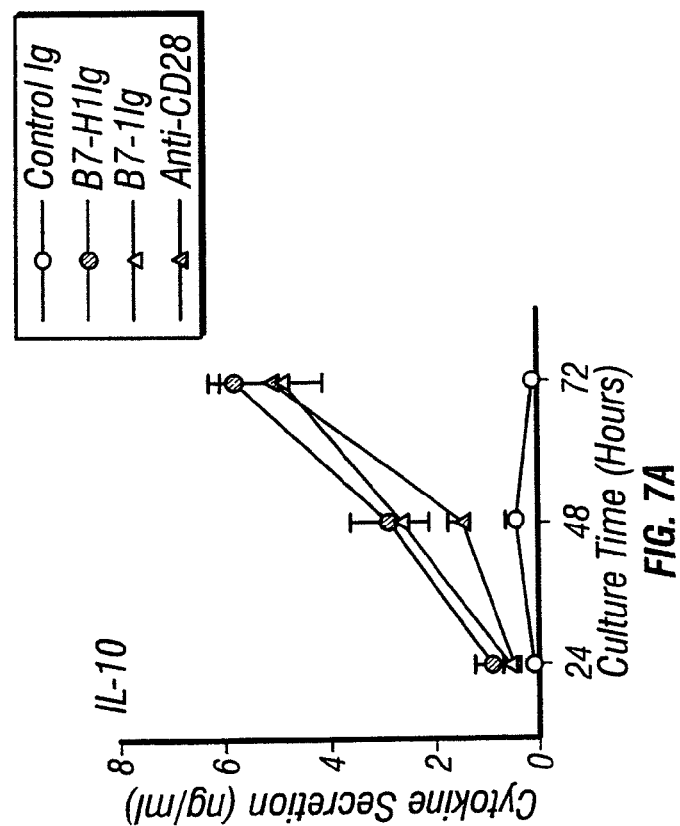

The levels of IL-2, IL-4, IFN-γ, and IL-10 produced by T cells after co-stimulation with hB7-H1Ig, B7-1Ig, or mAb specific for human CD28 in the presence of mAb specific for human CD3 (FIG. 7a-7d) were measured. Similar to B7-1Ig and anti-CD28, immobilized hB7-H1Ig antibody dramatically increased the production of IL-10 by T cells in response to immobilized mAb specific for human CD3 after stimulation for 48 and 72 hours (FIG. 7a). IL-10 was not detected if T cells were co-stimulated with immobilized control Ig. The level of IFN-γ was also significantly elevated by co-stimulation with immobilized hB7-H1Ig (FIG. 7b). In contrast to B7-1Ig and mAb specific for human CD28, hB7-H1Ig co-stimulated low or negligible levels of IL-2 (FIG. 7c) and IL-4 (FIG. 7d), respectively. These observations were reproducible in six independent experiments. These results show that co-stimulation by hB7-H1 preferentially stimulates the production of IL-10.

Figure 8A:
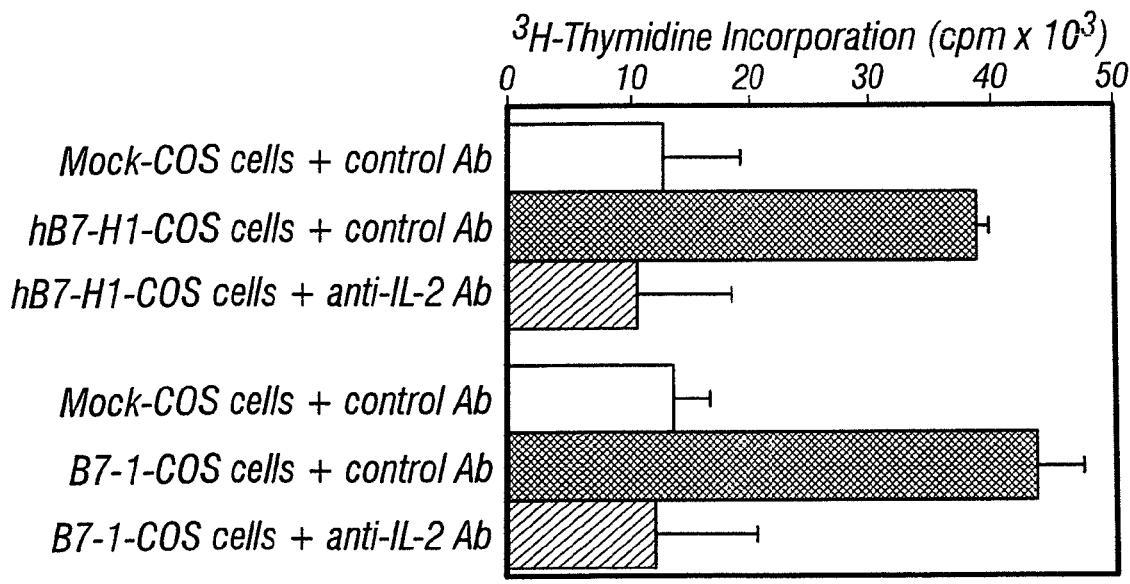
FIG. 8a is a bar graph showing the ability of antibody specific for human IL-2 to inhibit the proliferation of human T cells induced by antibody specific for human CD3 and co-stimulated by COS cells transfected with and expressing either hB7-H1 or human B7-1.
Figure 8B:
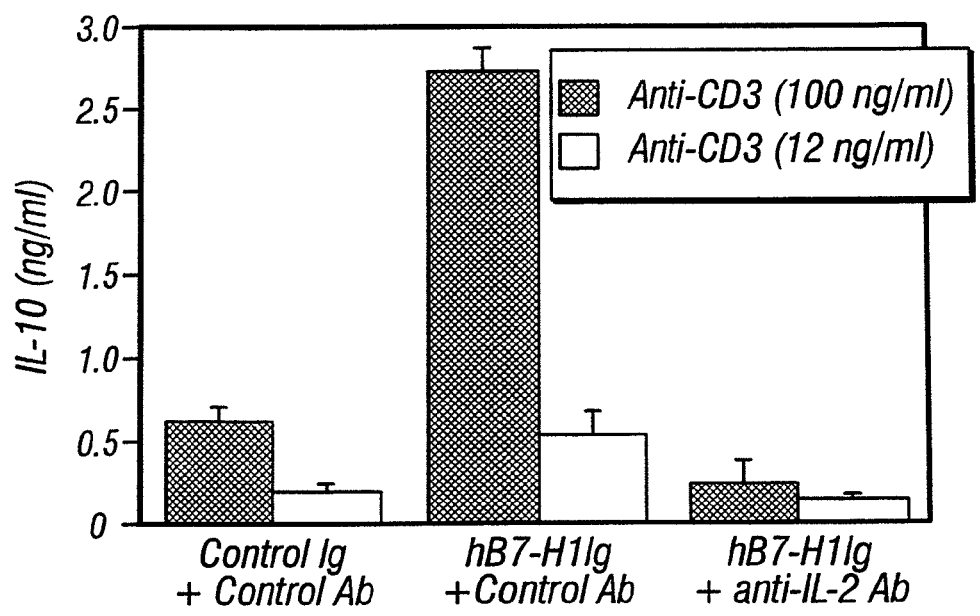
FIG. 8b is a bar graph showing the ability of antibody specific for human IL-2 to inhibit the production of IL-10 by human T cells stimulated by immobilized antibody specific for human CD3 and co-stimulated by either hB7-H1Ig or B7-1Ig.

The production of IL-2, although low, peaked at 24 hours upon hB7-H1 co-stimulation (FIG. 7c), while IL-10 secretion started to increase only after 48 and 72 hours (FIG. 7a). Increasing concentrations of hB7-H1Ig led to a small increase (<1 ng/ml) of IL-2 secretion (FIG. 7e). To determine the roles of the early-produced IL-2, the effects of mAb specific for human IL-2 on T cell proliferation and IL-10 production in B7H-mediated co-stimulation were tested. Similar to T cell proliferation induced by B7-1-COS cells and immobilized mAb specific for human CD3, T cell proliferation induced by hB7-H1-COS cells and mAb specific for human CD3 was blocked by inclusion of mAb specific for human IL-2 (FIG. 8a). Furthermore, IL-10 secretion from hB7-H1Ig-co-stimulated T cells was also inhibited by mAb specific for human IL-2 (FIG. 8b). Therefore, the hB7-H1 co-stimulation of both T cell growth and IL-10 secretion is an IL-2-dependent process.

Example 5 hB7-H1 Co-Stimulation Increases Apoptosis of Activated T Cells

Figure 9A:
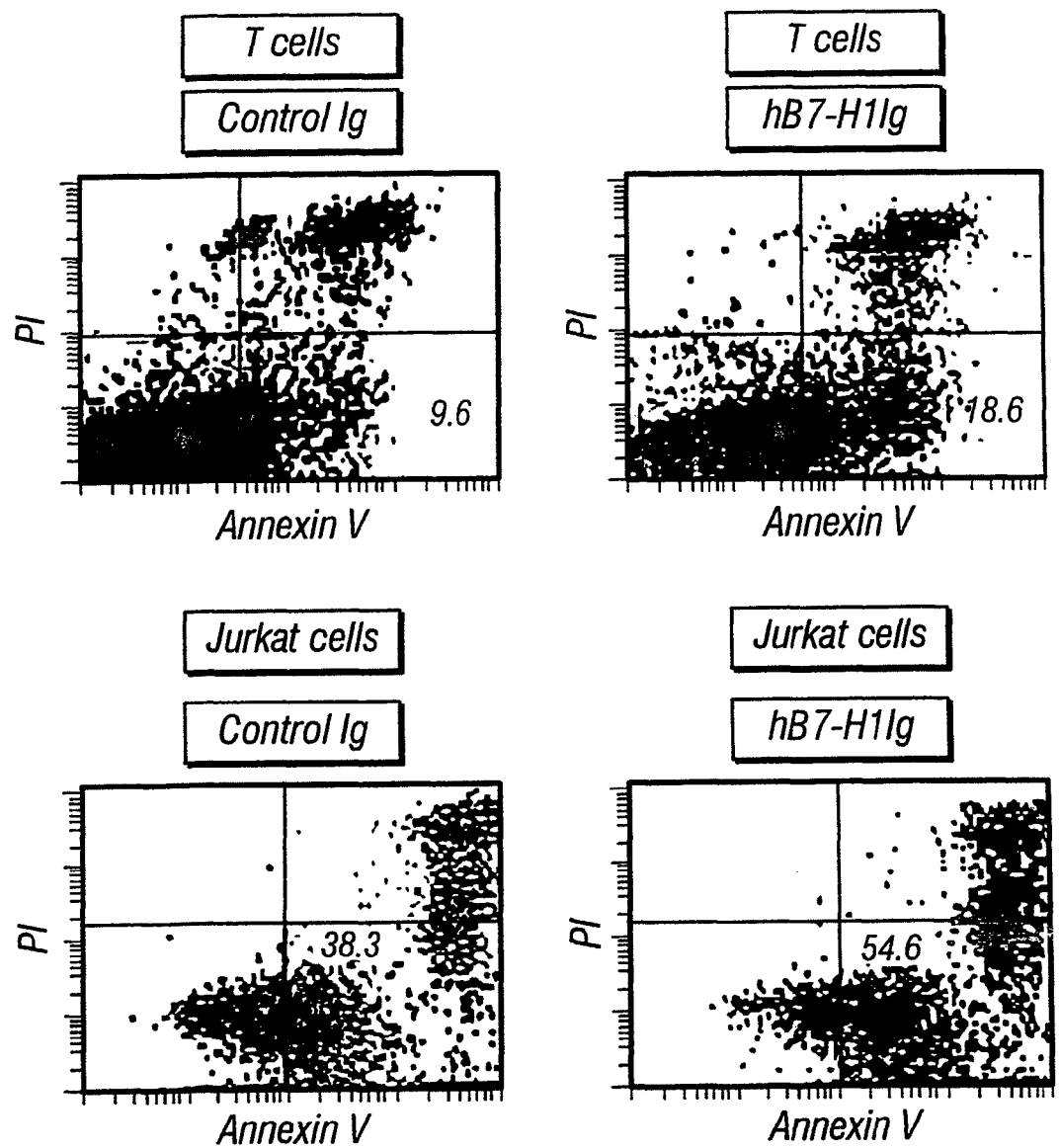
FIG. 9a is a series of two-dimensional fluorescence flow cytometry profiles showing the relative proportion of T cells in early (annexin V-positive, propidium iodide (PI)-negative) and late (annexin V-positive, PI-positive) apoptosis following activation by immobilized antibody specific for human CD3 and co-stimulation with either control Ig or hB7-H1Ig.
Figure 9B:
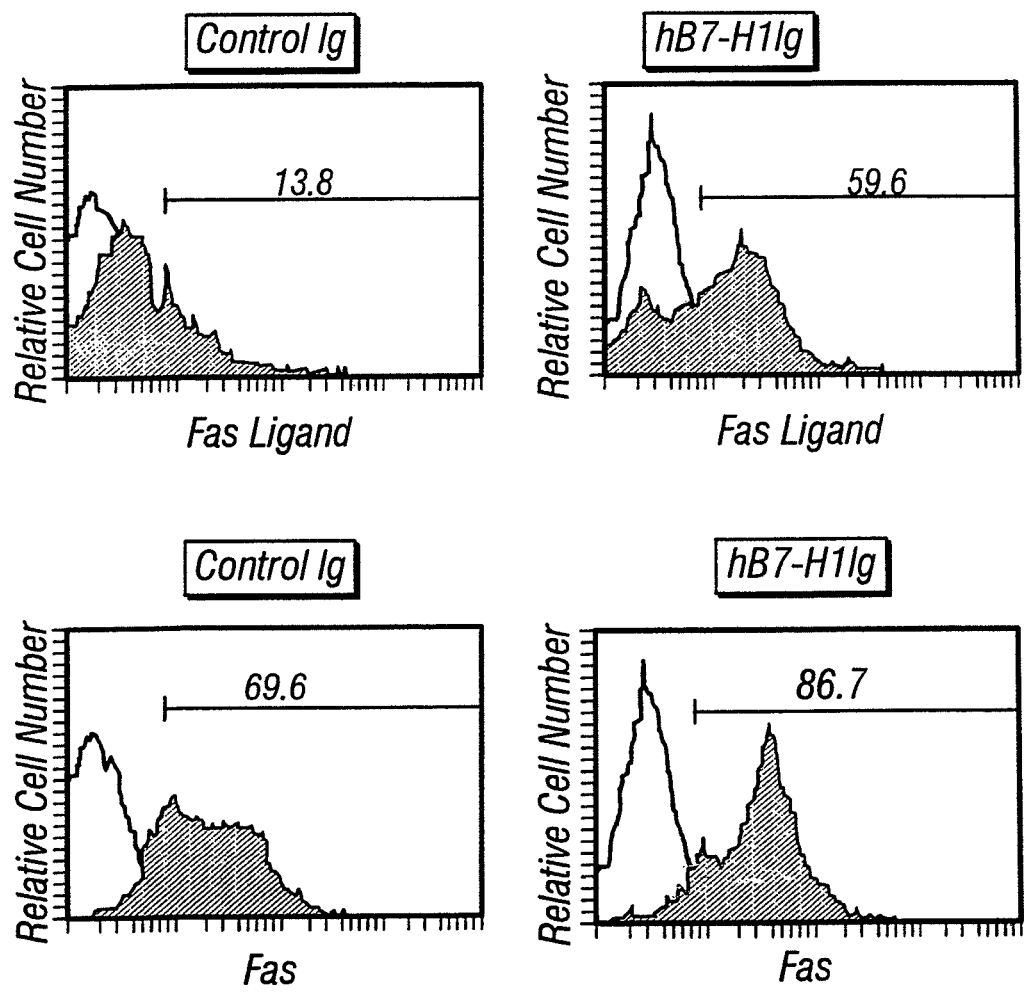
FIG. 9b is series of fluorescence flow cytometry profiles showing expression of Fas and FasL on human T cells following activation by immobilized antibody specific for human CD3 and co-stimulation with either control Ig or hB7-H1Ig.

To determine the effect of hB7-H1 ligation on the viability of activated T cells, the proportion of live T cells remaining after activation with an optimally activating dose of mAb specific for human CD3 in the presence of immobilized hB7-H1Ig was determined by trypan blue staining. A consistent decrease of alive T cells was observed. At the end of culture, T cells were stained with annexin V and propidium iodide (PI) to distinguish the early phase and late phase of apoptosis, respectively. The apoptotic cells in early phase (annexin V-positive, PI-negative) were significantly increased to 24.8% in the presence of hB7-H1Ig compared to 14.2% in the absence of hB7-H1Ig in 5 experiments (P=0.001). A representative experiment is shown in FIG. 9a (upper panel). Similar results were obtained using hB7-H1Ig-treated Jurkat cells (control Ig: 38.3% vs. hB7-H1Ig: 54.6%) (FIG. 9a, lower panel). The increased apoptosis was associated with upregulation of Fas and FasL expression on hB7-H1 co-stimulated T cells (FIG. 9b). These results indicated that hB7-H1 co-stimulation increased activation-induced T cell apoptosis moderately, and the increased apoptosis was associated with elevated expression of Fas and FasL.

Example 6

Production of Monoclonal Antibodies Specific for hB7-H1

Using standard protocols, BALB/c mice were immunized with purified hB7-H1Ig and splenocytes from the immunized mice were fused with X63-AG8.653 mouse myeloma cells. Five hybridoma lines were found to secrete antibodies specific for hB7-H1 in that, as detected by fluorescence flow cytometry, culture supernatants from these hybridoma lines positively stained hB7-H1/293 cells but did not stain control vector/293 cells. Furthermore, some of the antibodies inhibited the co-stimulatory activity of hB7-H1.

Example 7

Molecular Cloning and Expression Pattern of a Mouse B7-H1 (mB7-H1) Gene

Starting with two overlapping mouse EST clones (AA823166 and AA896104), and using a strategy similar to that for the hB7-H1 gene, a cDNA fragment that included an orf encoding mB7-H1 was cloned. The coding sequence for mB7-H1 (SEQ ID NO:4) (FIG. 10) was obtained and the amino acid sequence of mB7-H1 (SEQ ID NO: 3) (FIG. 11) was derived from it. The length of mB7-H1 is identical to that of hB7-H1 and it has the same conserved cysteine residues found in hB7-H1 (see Example 2). A cDNA fragment encoding full-length mB7-H1 was cloned into the pcDNA3 vector (Invitrogen, Carlsbad, Calif.) to give mB7-H1.pcDNA3.

mB7-H1, like hB7-H1, is a type I transmembrane protein of 290 amino acids that has 69% overall amino acid homology to hB7-H1 (FIG. 12a). Similar to other members of B7 family, mB7-H1 consists of an Ig V-like domain, an Ig C-like domain, a hydrophobic transmembrane domain and a cytoplasmic tail. mB7-H1 shares 20% homology to mouse B7-1, 14% to mouse B7-2, and 19% to mouse B7h/B7RP-1, based on analysis using McVector 6.5 software (Clustal W Program) (FIG. 12b).

RNA analysis revealed that mB7-H1 mRNA is abundant in mouse heart, spleen, lung, skeletal muscle and liver, and less abundant but present in mouse kidney, liver, thymus, and thyroid. Thus, the expression pattern of mB7-H1 mRNA is similar to that of human B7-H1 mRNA. Negligible expression of the mB7-H1 mRNA was observed in pancreas and testis.

Figure 13:
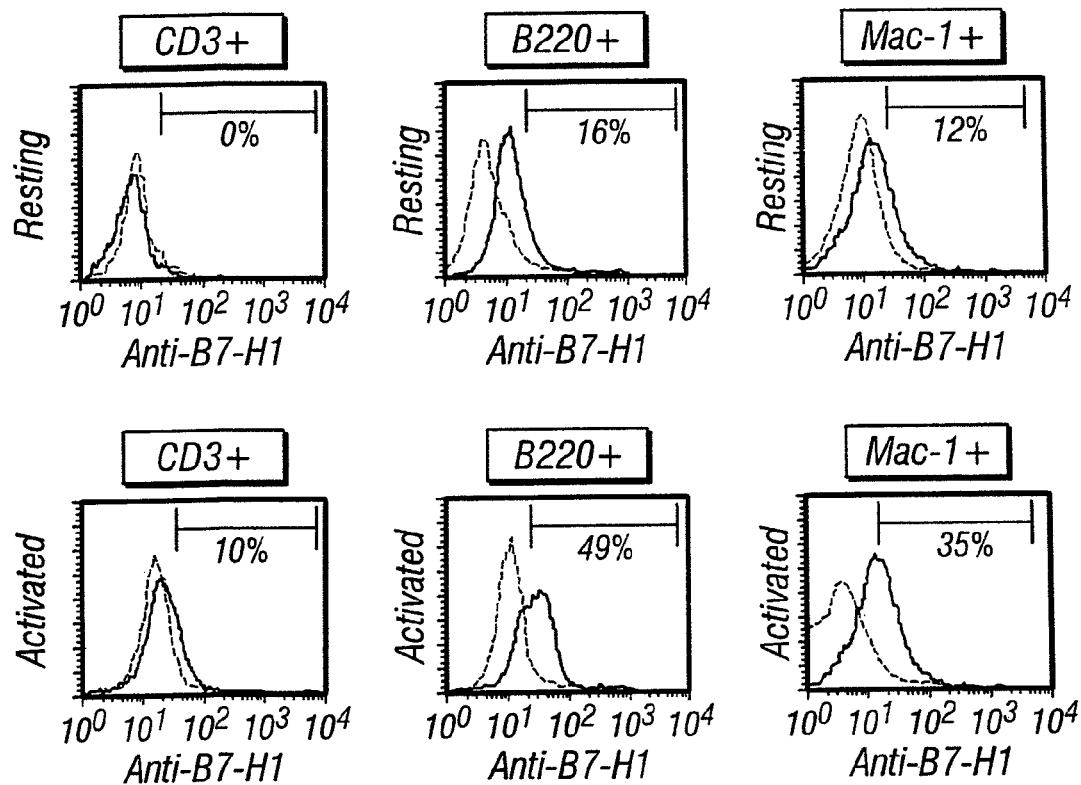
FIG. 13 is a series of fluorescence flow cytometry histograms showing relative levels of cell surface expression of mB7-H1 on resting and activated mouse CD3+ T cells, mouse B220+ B cells, and Mac-1+ mouse macrophages.

FFC analysis using the anti-mB7-H1 antibody showed that resting mouse CD3$^+$ T cells do not express mB7-H1 (FIG. 13, upper panel). However, a small fraction of B220$^+$ mouse B cells and Mac-1$^+$ mouse macrophages expressed a low level of mB7-H1 (FIG. 13, upper panel). Stimulation of mouse T cells with antibodies specific for mouse CD3 and mouse CD28 moderately increased the mB7-H1 expression on T cells. Activation of mouse B cells with LPS and macrophages with LPS plus IFN-γ significantly increased the expression of mB7-H1 on their surfaces (FIG. 13, lower panel). Thus, mB7-H1, like hB7-H1, is an inducible cell surface molecule.

Example 8

Co-Stimulation of Mouse T Cell Proliferation by mb7-H1

Figure 14A:
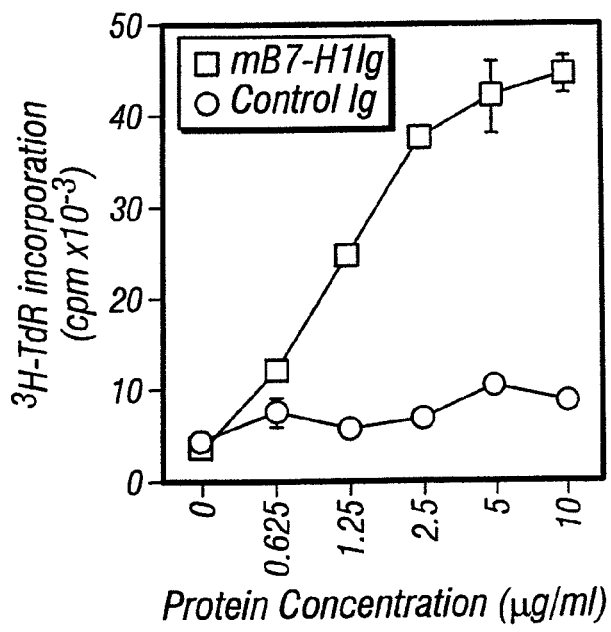
FIG. 14a is a line graph showing the ability of various concentrations of immobilized mB7-H1Ig or immobilized control Ig to co-stimulate the in vitro proliferative response of mouse T cells to a suboptimal dose of immobilized antibody specific for mouse CD3.

To investigate the costimulatory effect of mB7-H1, nylon-wool purified mouse T cells were activated with a suboptimal dose of mAb specific for mouse CD3 (coated onto culture well bottoms at a concentration of 200 ng/ml) and co-stimulated with various concentrations of mB7-H1Ig. mB7-H1Ig enhanced T cell proliferation by up to 5-fold compared to control Ig (FIG. 14a). The costimulatory effect of the mB7-H1Ig was dose-dependent and dependent on the presence of mAb specific for mouse CD3 since in the absence of mAb specific for mouse CD3, mB7-H1Ig (up to a concentration of mB7-H1Ig 10 ng/ml) failed to stimulate the proliferation of T cells. When nylon-wool purified mouse T cells were cultured with 293 cells transfected with either mB7-H1.pcDNA3 or control vector in the presence of suboptimal doses of mAb specific for mouse CD3, mB7-H1-transfected 293 cells also enhanced T cell proliferation substantially compared to the T cell proliferation in the presence of the control vector-transfected 293 cells. Thus, similar to hB7-H1, mB7-H1 costimulates T cell proliferation.

Figure 14B:
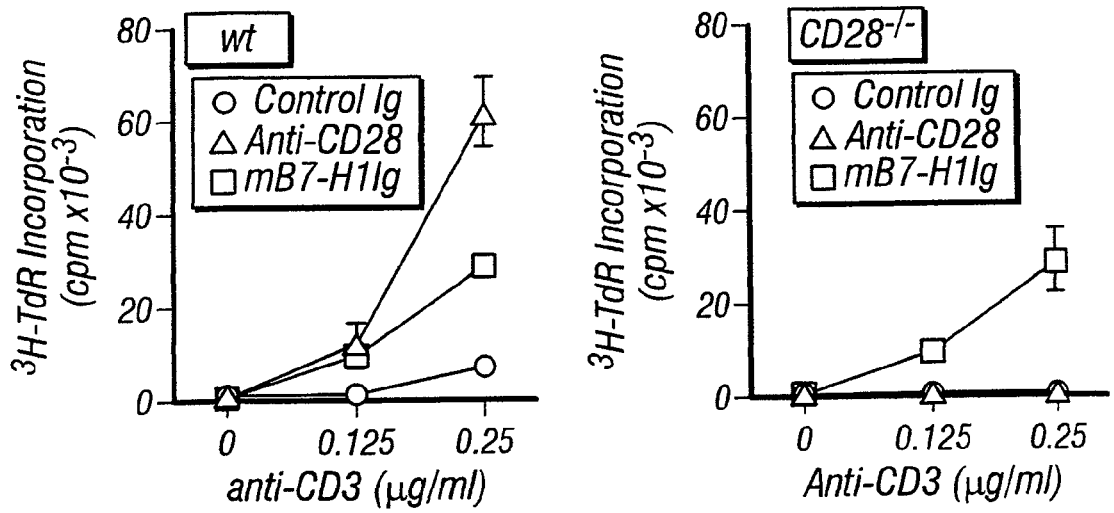
FIG. 14b is a pair of line graphs showing the ability of immobilized mB7-H1Ig, immobilized control Ig, or soluble antibody specific for mouse CD28 to co-stimulate the in vitro proliferative response of wild type ("wt") C57BL/6 mouse (left graph) or CD28-deficient ("CD28$^{-/-}$") C57BL/6 mouse (right graph) T cells to two suboptimal doses of immobilized antibody specific for mouse CD3.

The role of CD28 in mB7-H1 costimulation was evaluated by comparing the effects of mB7-H1Ig costimulation on T cells isolated from $CD28^{-/-}$ mice and from normal mice. Nylon wool purified mouse T cells were activated with two suboptimal doses of antibody specific for mouse CD3 (coated onto the well bottoms of 96 well tissue culture plates at a concentration of 0.125 µg/ml or 0.25 µg/ml) and either soluble antibody specific for mouse CD28 (2.5 µg/ml) or mB7-H1Ig or control Ig (both coated onto the well bottoms of 96 well tissue culture plates at a concentration of 10 µg/ml). As shown in FIG. 14b, while there was no co-stimulatory effect of anti-CD28 mAb on $CD28^{-/-}$ T cells, mB7-H1Ig, induced the proliferation of both $CD28^{-/-}$ (FIG. 14b, right panel) and $CD28^{+/+}$ ("wt"; FIG. 14b, left panel) T cells to a similar degree. Therefore, mB7-H1 can co-stimulate T cell growth in a CD28-independent fashion.

Figure 14C:
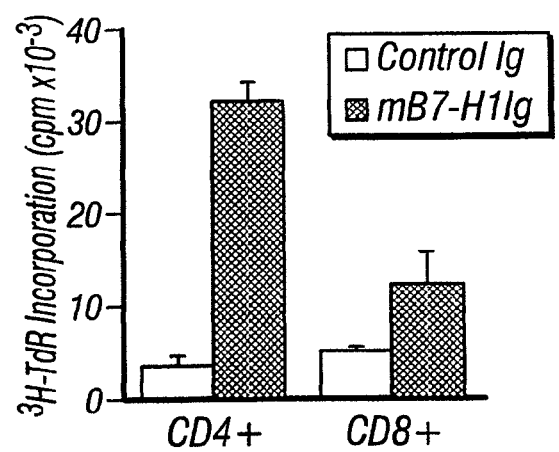
FIG. 14c is a bar graph showing the ability of immobilized mB7-H1Ig or immobilized control Ig to co-stimulate the in vitro proliferative response of purified CD4+ or CD8+ mouse T cells to a suboptimal dose of immobilized antibody specific for mouse CD3.

In order to test whether mB7-H1 preferentially co-stimulates $CD4^+$ or $CD8^+$ T cells, purified $CD4^+$ and $CD8^+$ T cells were stimulated with mB7-H1Ig (same concentration as in the experiment shown in FIG. 14b) and mAb specific for mouse CD3 (coated onto the well bottoms of 96 well tissue culture plates at a concentration of 200 ng/ml). Proliferation of $CD4^+$ T cells was enhanced about 10 fold by mB7-H1Ig and the proliferation of $CD8^+$ T cells was only enhanced 2-3 fold mB7-H1Ig (FIG. 14c). Thus, the co-stimulatory effect of mB7-H1 is more potent on $CD4^+$ T cells than on CD8+ cells.

Example 9

Co-Stimulation of Cytokine Production by mB7-H1

Figure 15A:
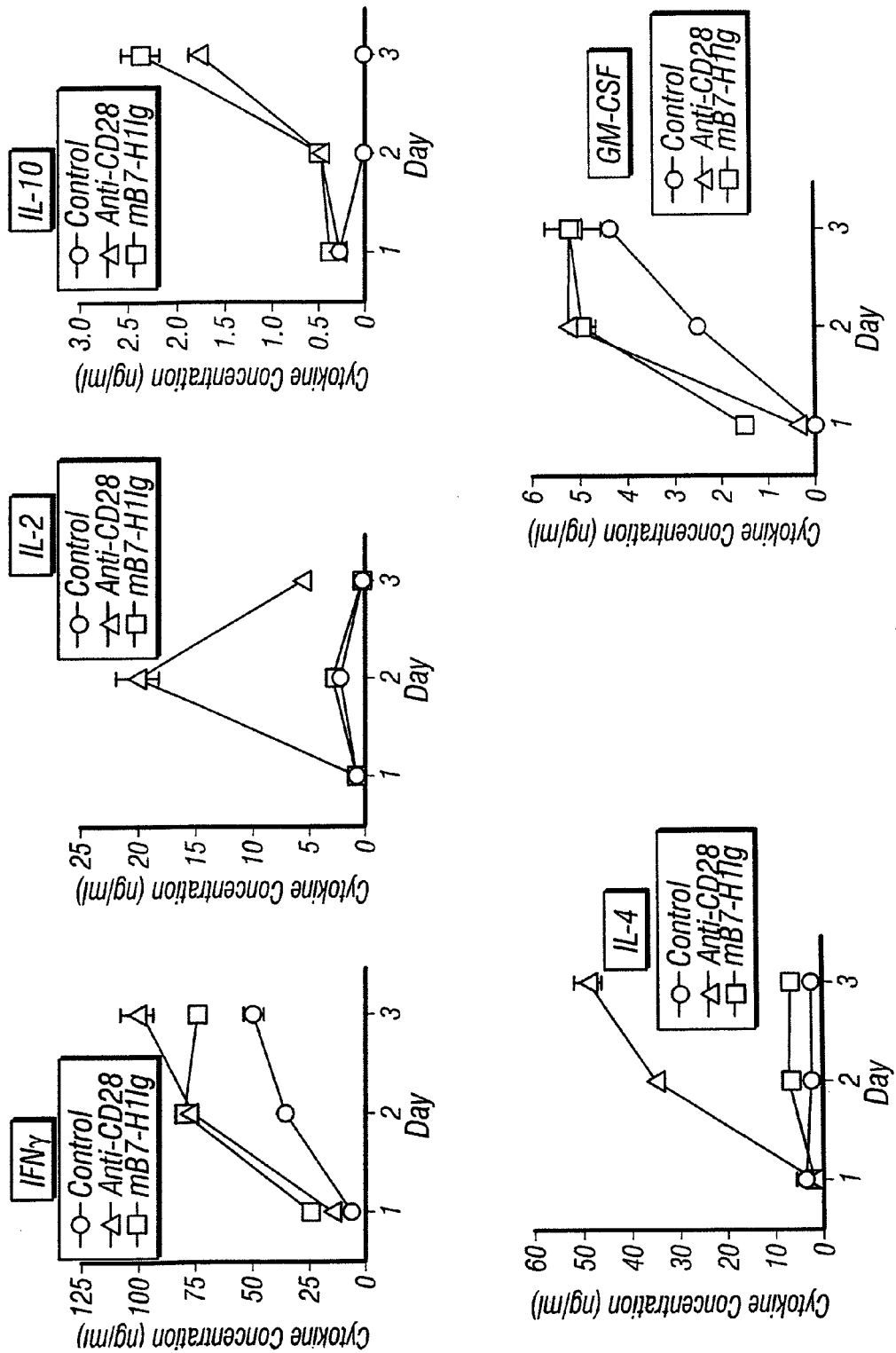
FIG. 15a is a series of line graphs showing the ability of immobilized mB7-H1Ig, immobilized control Ig, or soluble antibody specific for mouse CD28 ("Anti-CD28") to stimulate the in vitro production (on days one, two, and three after initiation of the cultures) of various cytokines by C57BL/6 mouse T cells in response to immobilized antibody specific for mouse CD3.

The levels of IL-10, IFN-γ, IL-2, IL-4 and GM-CSF produced by T cells activated with mAb specific for mouse CD3 and co-stimulated with either mB7-H1Ig or anti-CD28 mAb were measured. FIG. 15a shows that mB7-H1Ig, similar to mAb specific for mouse CD28, co-stimulates the production of high levels of IL-10 in the day 3 cultures. IL-10 was not detectable at day 3 when T cells were treated with either control Ig and mAb specific for mouse CD3 or mAb specific for mouse CD3 alone. mB7-H1 and mAb specific for mouse CD28 enhanced the production of IFN-γ and GM-CSF. In contrast to mAb specific for mouse CD28, which induced high levels of IL-2 and IL-4, mB7-H11 g induced no or negligible levels of IL-2 and IL-4 at all time points (FIG. 15a). Thus, mB7-H1 and hB7-H1 co-stimulate the production of a similar spectrum of cytokines.

Figure 15B:
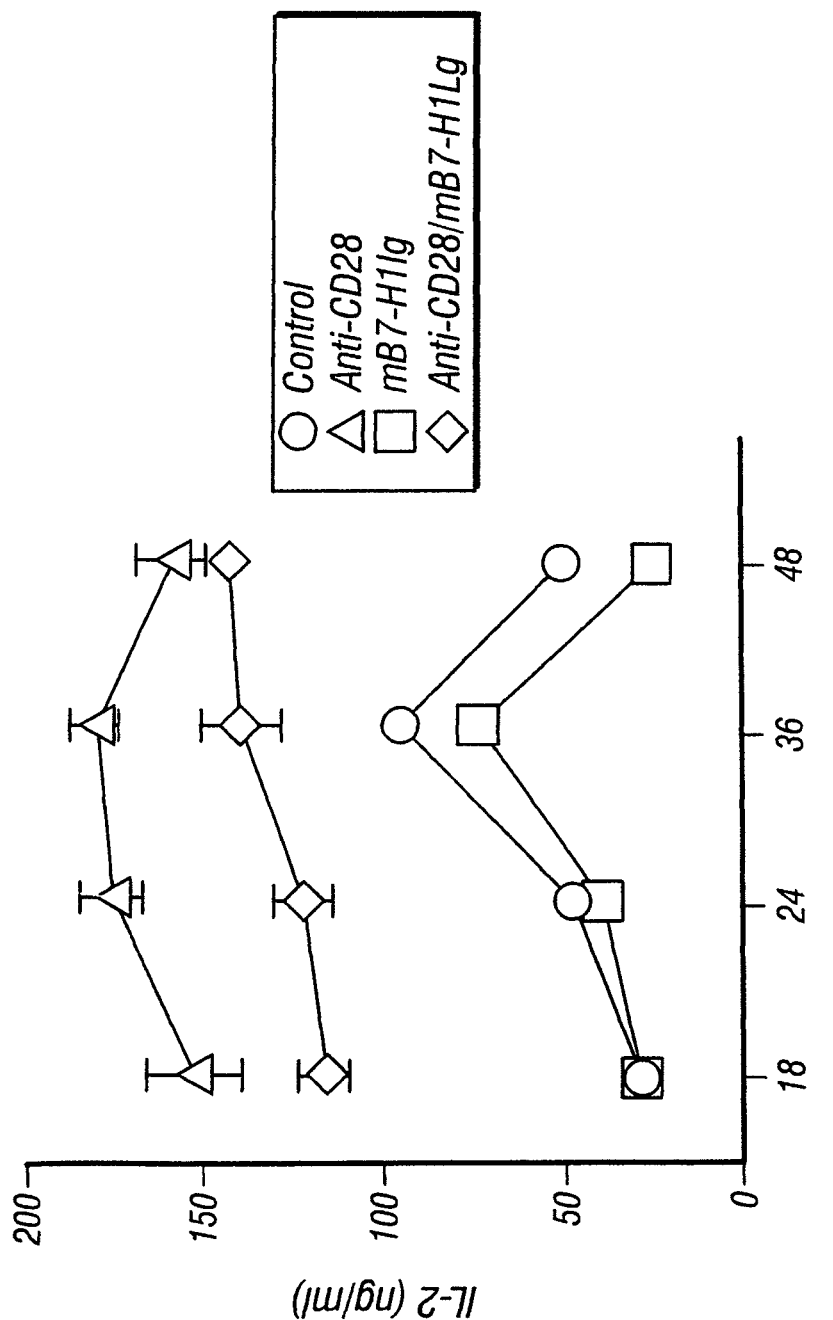
FIG. 15b is a line graph showing the effect of immobilized mB7-H1Ig on the in vitro production (18, 24, 36, and 48 hours after initiation of the cultures) of IL-2 by C57BL/6 mouse T cells responding to immobilized antibody specific for mouse CD3 and co-stimulated by soluble antibody specific for mouse CD28 ("Anti-CD28").

Since IL-2 was undetectable in culture supernatants from mB7-H1Ig co-stimulated cultures, it seemed possible that mB7-H1 ligation inhibited IL-2 secretion. To test this possibility, the effect of mB7-H1 on IL-2 secretion by T cells activated by mAb specific for mouse CD3 and co-stimulated with mAb specific for mouse CD28 was tested. FIG. 15b shows that inclusion of immobilized mB7-H1Ig (at concentrations up to 10 ng/ml) in the culture resulted in a small decrease in IL-2 production during the 18-48 h culture period that was statistically insignificant; in several repeat experiments no statistically significant decrease was ever seen. Similarly, mB7-H1Ig did not inhibit IL-2 production in cultures in which T cells were activated by mAb specific for mouse CD3 alone (FIG. 15b). The results thus indicate that mB7-H1 ligation does not inhibit the production of IL-2.

Example 10

Figure 16A:
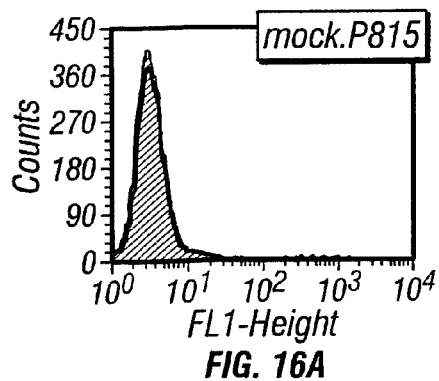
FIG. 16a and FIG. 16b are fluorescence flow cytometry histograms showing lack of surface expression of murine B7-1 (FIG. 16a) and mB7-H1 (FIG. 16b) on P815 cells transfected with a control expression vector ("mock.P815").
Figure 16B:
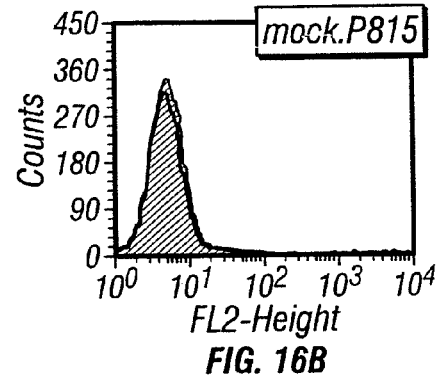
Figure 17A:
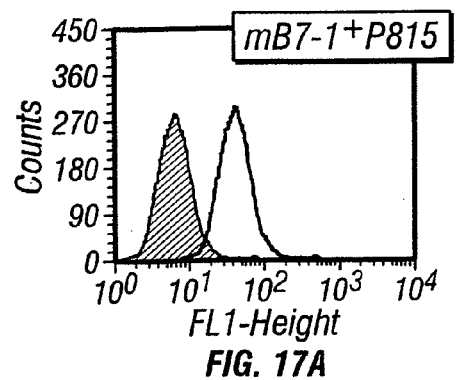
FIG. 17a and FIG. 17b are fluorescence flow cytometry histograms showing surface expression of murine B7-1 (FIG. 17a) and lack of surface expression of mB7-H1 (FIG. 17b) on P815 cells transfected with an expression vector containing a nucleic acid sequence encoding murine B7-1 ("mB7-1$^+$ P815").
Figure 17B:
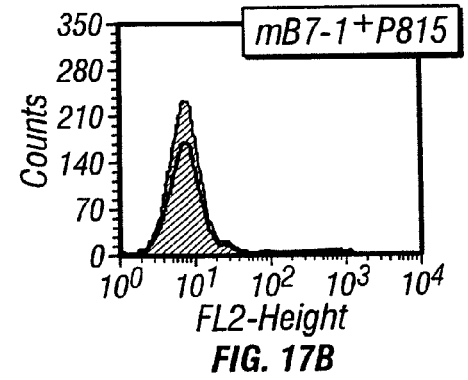
Figure 18A:
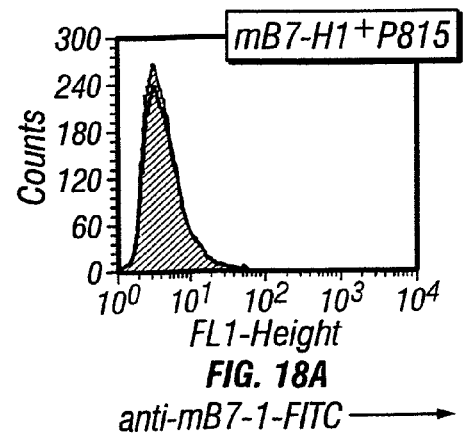
FIG. 18a and FIG. 18b are fluorescence flow cytometry histograms showing lack of surface expression of mB7-1 (FIG. 18a) and showing surface expression of mB7-H1 (FIG. 18b) on P815 cells transfected with an expression vector containing a nucleic acid sequence encoding mB7-H1 ("mB7-H1$^+$ P815").
Figure 18B:
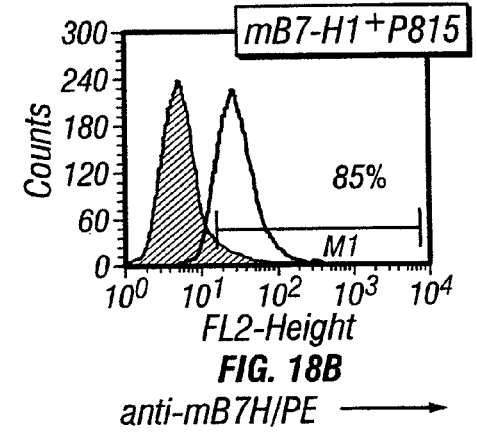

Expression of mB7-H1 on Transfected P815 Tumor Cells and Decreased Growth Rate of the Transfected P815 Cells in Mice Mouse (DBA/2) P815 mastocytoma cells were stably transfected with the expression plasmid (mB7-H1.pcDNA3) containing the coding sequence for mB7-H1 using FUGENE™ (Roche, Mannheim, Germany) according to the manufacturer's instructions. The transfected cells were selected in complete medium containing G418 (1 mg/ml; Life Technologies) and were subsequently cloned by limiting dilution. mB7-H1 expressing P815 cells were identified by FFC using the above-described anti-mB7-H1 polyclonal antibody preparation. A representative clone (mB7-H1$^+$ P815) was selected for further studies. P815 clones transfected with the pc DNA vector (mock.P815) or MB7-1 (mB7-1$^+$ P815) were generated similarly [Chen et al. (1994) *J. Exp. Med.* 179, 523-532]. Using a PE-conjugated rat polyclonal antibody specific for mB7-H1 ("anti-mB7H/PE"), mB7-H1 expression was detected by FFC on the mB7H-H1$^+$ P815 cells (FIG. 18b) but not on either mock transfected P815 cells ("mock.P815") (FIG. 16b) or P815 cells transfected with a construct encoding murine B7-1 ("mB7-1$^+$ P815") (FIG. 17b). On the other hand, the mB7-1$^+$ P815 cells were stained with a FITC-conjugated mAb specific for murine B7-1 ("anti-mB7-1-FITC") (FIG. 17a). Furthermore, inclusion of the mB7-H1 peptide used to make the polyclonal anti-mB7-H1 antibody in the staining reaction mixture completely blocked binding of the polyclonal anti-mB7-H1 antibody to the mB7-H1$^+$ P815 cells.

Figure 19B:
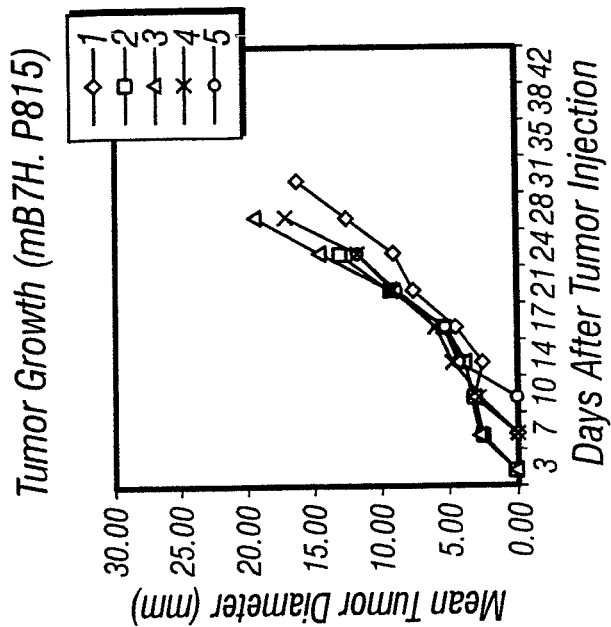
FIG. 19a and FIG. 19b are line graphs showing the growth rate of P815 tumors in DBA/2 mice injected subcutaneously with P815 cells transfected with a control expression vector (FIG. 19a) or an expression vector containing a nucleic acid sequence encoding mB7-H1 (FIG. 19b).
Figure 19A:
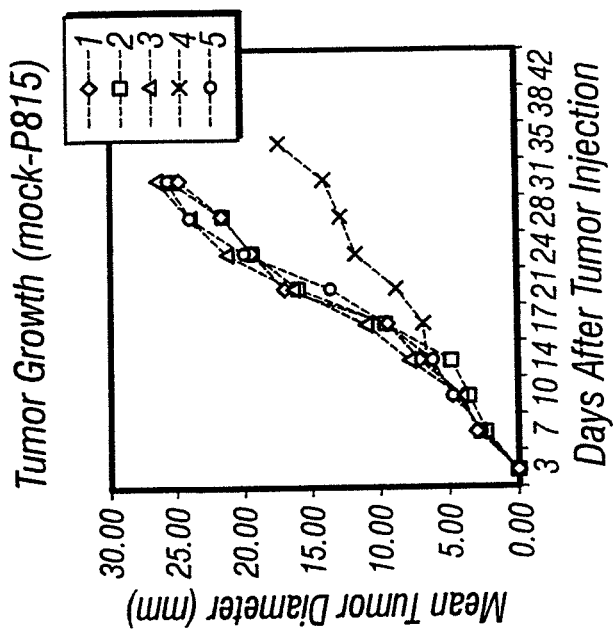

Groups (5 mice per group) of DBA/2 mice were injected subcutaneously (s.c.) with either $2\times10^5$ mock.P815 or mB7-H1$^+$ P815 cells. The growth rate of the mock.P815 cells was significantly greater in 4 out of 5 injected mice (FIG. 19a) than in the 5 mice injected with mB7-H1$^+$ P815 (FIG. 19b). These findings indicate that the mB7-H1$^+$ P81.5 cells were significantly more immunogenic than mock.P815 cells and, therefore, that expression of mB7-H1 expression by P815 cells enhances their ability to elicit protective immunity.

Example 11 mB7-H1 Costimulation Fails to Enhance Allogeneic and Syngeneic CTL Responses

Figure 20A:
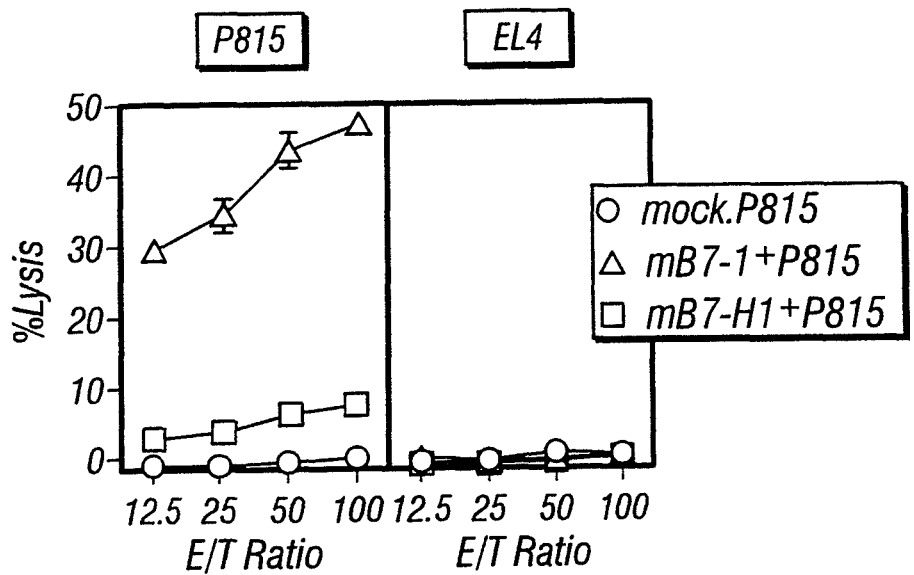
FIG. 20a is a pair of line graphs showing the ability of control mock-transfected P815 cells ("mock.P815"), P815 cells transfected with an expression vector containing a cDNA sequence encoding mB7-H1 ("mB7-H1$^+$ P815"), or P815 cells transfected with an expression vector containing a cDNA sequence encoding mB7-1 ("mB7-1$^+$ P815") to activate allospecific C57BL/6 mouse CTL in vitro. The effector cell populations were tested for cytotoxic activity ("% Lysis") at various effector to target cell (E/T) ratios against wild type P815 (left graph) and control EL4 (right graph) target cells.

To examine the effect of mB7-H1 on the generation of allogeneic CTL in vitro, nylon wool-purified T cells from B6 mice ($H-2^b$) were co-cultured with irradiated mock.P815 ($H-2^d$), mB7-1$^+$ P815, or mB7-H1$^+$ P815 cells for 5 days and the CTL activity of cells harvested from the cultures was tested against wild-type P815 target cells in standard $^{51}$Cr release assays at the indicated effector to target cell ratios ("E/T ratio"). As depicted in FIG. 20a, mB7-H1$^+$ P815 cells and mock.P815 cells were poor stimulators of CTL activity. In contrast, mB7-1$^+$ P815 cells elicited strong P815-specific CTL activity. The CTL induced by mB7-1 were alloantigen-specific since they did not lyse responder (B6) H-2 haplotype ($H-2^b$) EL4 tumor target cells. Thus, mB7-H1 expression does not facilitate the generation of allogeneic CTL.

The ability of mB7-H1$^+$ P815 cells to stimulate P815 tumor specific CTL in vivo was tested. DBA/2 mice were injected s.c. with mock.P815, mB7-1$^+$ P815, or mB7-H1$^+$ P815 cells.

Figure 20B:
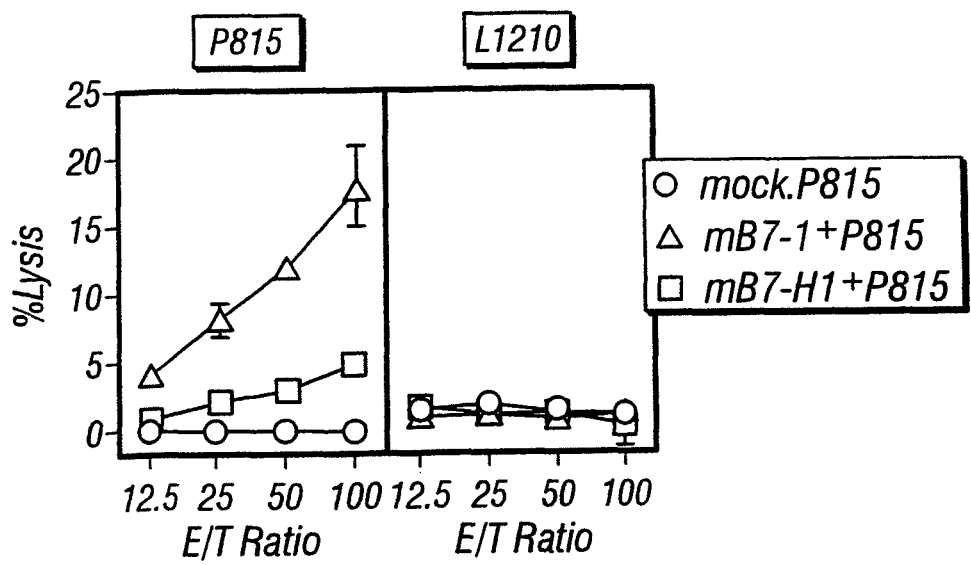
FIG. 20b is a pair of line graphs showing the ability of control mock-transfected P815 cells ("mock. P815"), P815 cells transfected with an expression vector containing a cDNA sequence encoding mB7-H1 ("mB7-H1$^+$ P815"), or P815 cells transfected with an expression vector containing a cDNA sequence encoding mB7-1 ("mB7-1$^+$ P815") to activate tumor-specific DBA/2 mouse CTL in vivo. The effector cell populations were tested for cytotoxic activity ("% Lysis") at various E/T ratios against wild type P815 (left graph) and control L1210 (right graph) target cells.

Tumor-draining lymph nodes were removed 7 days later and T cells isolated from them were cultured with wild-type P815 cells for 5 days. Cells harvested from the cultures were tested for CTL activity against wild-type P815 target cells in a standard $^{51}$Cr release assay at the indicated E/T ratios (FIG. 20b). Effector cells from mice injected with mB7-H1$^+$ P815 showed slightly increased CTL activity against P815 cells compared to effector cells from the mock.P815-injected mice; this difference in CTL activity was however statistically insignificant. In contrast, mB7-1$^+$ P815 cells elicited strong CTL activity. CTL activity was P815 tumor-specific since syngeneic L1210 tumor target cells were not lysed. Thus, expression of mB7-H1 in P815 cells does not enhance the induction of CTL activity against P815 tumor antigens.

Example 12

Figure 21:
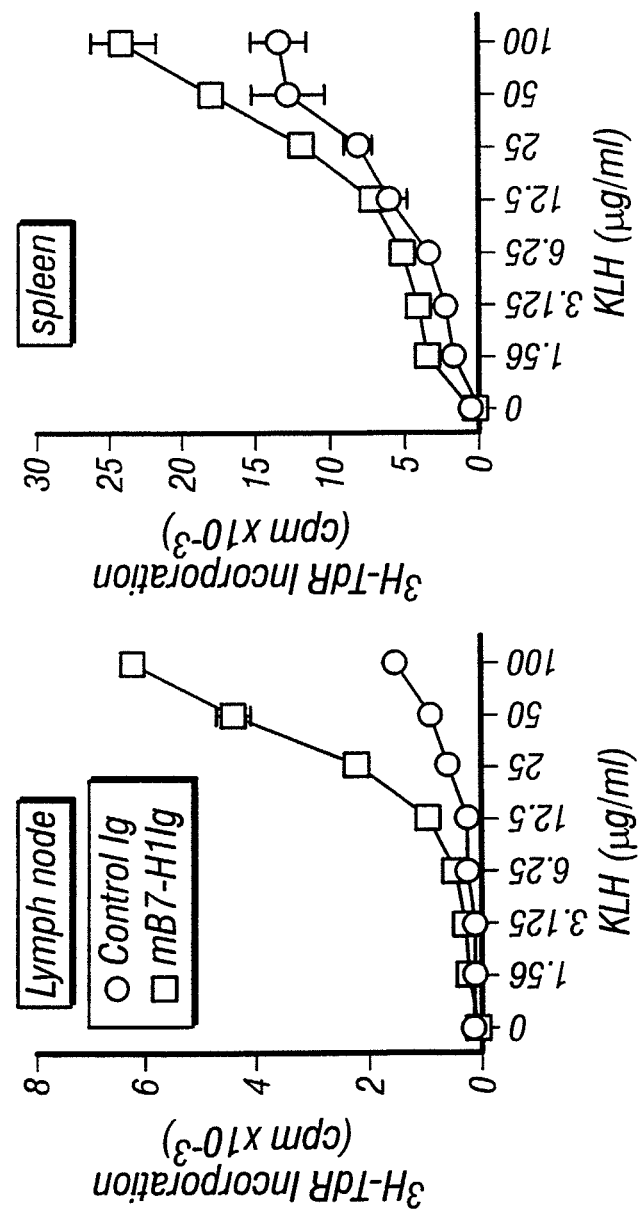
FIG. 21 is a pair of line graphs showing the in vitro proliferative responses to various concentrations of keyhole limpet hemacyanin (KLH) of draining lymph node (left graph) or spleen (right graph) T cells from C57BL/6 immunized intraperitoneally (i.p.) with trinitrophenol (TNP) conjugated KLH (TNP-KLH) in incomplete Freund's adjuvant and subsequently injected i.p. with mB7-H1Ig or control Ig.

B7-H1 Costimulation Amplifies Antigen-Specific T Helper Cell Responses, T Cell-Dependent Humoral Responses, and Expression of CD40L on T Cells To investigate the effect of mB7-H1 costimulation on T helper cell function, B6 mice were immunized with TNP-conjugated KLH on day 0, and were injected with mB7-H1Ig at day 1 and day 4. The in vitro proliferative responses of T cells obtained from both lymph nodes and spleens of the immunized mice to various concentrations of KLH were measured. As shown in FIG. 21, T cells from both spleens and lymph nodes of TNP-KLH-immunized mice proliferated in response to KLH in a dose dependent fashion. Administration of mB7-H1Ig to TNP-KLH-immunized mice amplified the subsequent in vitro proliferative responses of T cells by up to 2-3 fold. These results indicate that mB7-H1 co-stimulation enhances T helper cell responses in vivo.

Figure 22:
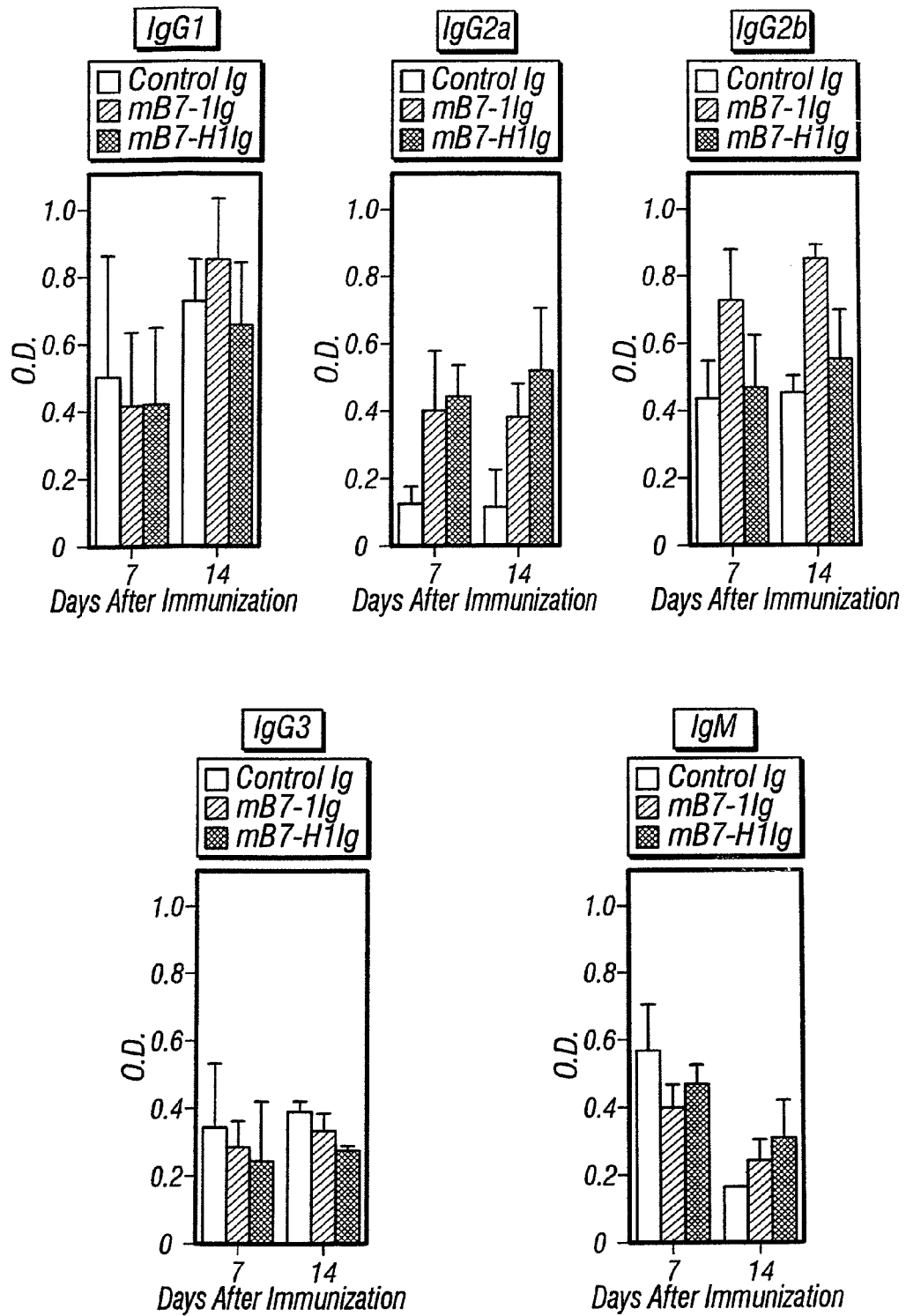
FIG. 22 is a series of bar graphs showing the relative levels (as measured by ELISA) of IgG1, IgG2a, IgG2b, IgG3, or IgM antibodies specific for TNP in the sera of C57BL/6 mice injected i.p. with TNP-KLH in phosphate buffered saline and either control Ig, mB7-H1Ig, or mB7-1Ig.

The effect of mB7-H1 co-stimulation on the generation of antigen-specific antibodies to TNP was investigated in a system well recognized as measuring helper T cell-dependent antibody responses [Marrack and Kappler (1975) *J. Immunol.* 114, 1116-1125; Romano et al. (1975) *Proc. Natl. Acad. Sci. USA* 72, 4555-4558]. Thus, the level of antibodies specific for TNP in the sera of mice immunized with TNP-KLH was measured after treatment with control Ig, mB7-1Ig, or mB7-H1Ig. In preliminary experiments, a significant increase in the total anti-TNP IgG level was observed in sera of mice immunized with TNP-KLH and treated with mB7-H1Ig compared to sera of mice immunized with TNP-KLH and treated with control mIg. The relative levels of IgM and individual IgG subclass (IgG1, IgG2a, IgG2b and IgG3) anti-TNP antibodies elicited by TNP-KLH immunization and various costimulations were each measured. As shown in FIG. 22, the amount of TNP-specific IgG2a antibody was increased significantly in the sera of mice immunized with TNP-KLH and treated with mB7-H1Ig. The effect was different from that elicited by mB7-1Ig in which the levels of antibodies specific for TNP of other IgG subclasses (IgG1 and IgG2b) were also significantly increased (FIG. 22). Thus, mB7-H1 costimulation enhances T helper cell proliferation and T helper-dependent antibody responses, particularly IgG2a responses.

Figure 23A:
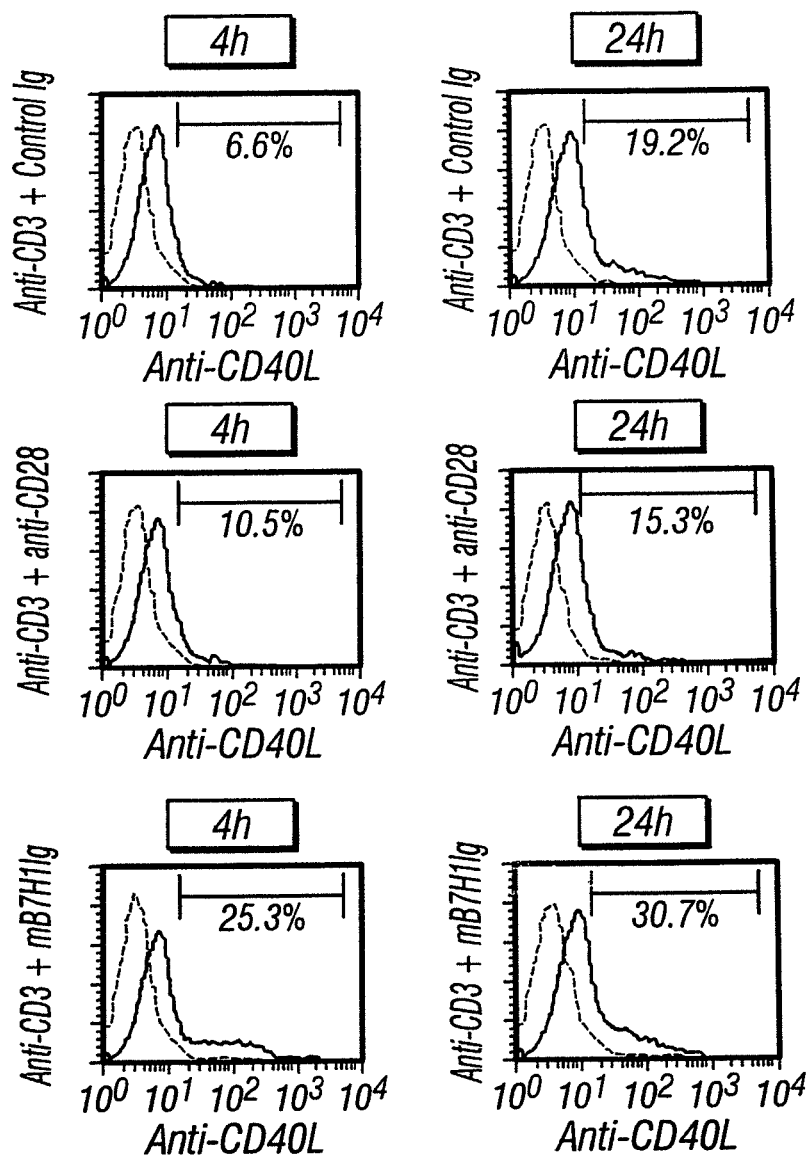
FIG. 23a is a series of fluorescence flow cytometry histograms showing the relative levels of cell surface expression of CD40 ligand (CD40L) (as measured by the binding of an antibody specific for mouse CD40L ("anti-CD40L")) on purified mouse CD4+ T cells (at 4 and 24 hours after initiation of the cultures) activated by immobilized antibody specific for mouse CD3 ("anti-CD3") coated onto the bottoms of tissue culture wells at a concentration of 200 ng/ml and co-stimulated by immobilized control Ig, immobilized mB7-H1Ig, or soluble antibody specific for mouse CD28 ("anti-CD28").
Figure 23B:
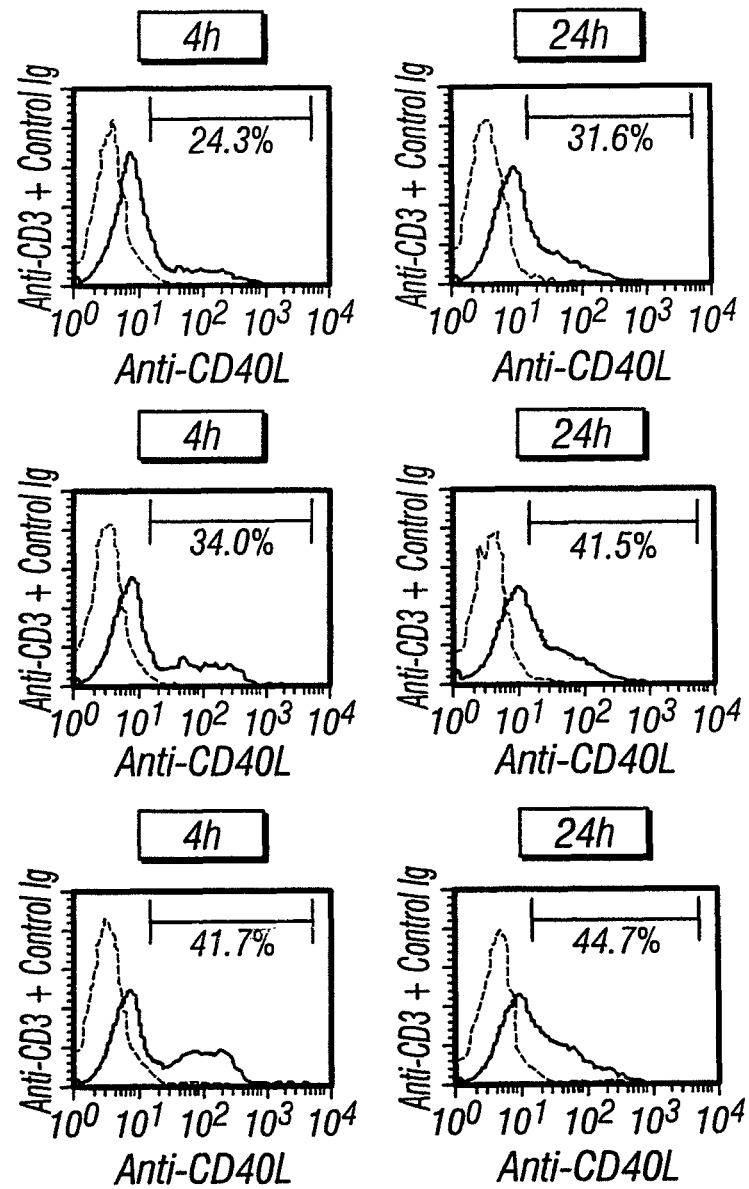
FIG. 23b is a series of fluorescence flow cytometry histograms showing the relative levels of cell surface expression of CD40 ligand (CD40L) (as measured by the binding of an antibody specific for mouse CD40L ("anti-CD40L")) on purified mouse CD4+ T cells (at 4 and 24 hours after initiation of the cultures) activated by immobilized antibody specific for mouse CD3 ("anti-CD3") coated onto the bottoms of tissue culture wells at a concentration of 1,000 ng/ml and co-stimulated by immobilized control Ig, immobilized mB7-H1Ig, or soluble antibody specific for mouse CD28 ("anti-CD28").

The CD40-CD40 ligand (CD40L) interaction in T helper cell-B cell interactions is critical for the generation of antibody responses and for Ig class switching [Calderhead et al. (2000) *Curr. Top. Microbiol. Immunol.* 245, 73-99]. The effect of co-stimulation with mB7-H1Ig on the level of CD40L on T cells was investigated. Purified CD4+ T cells from B6 mice were stimulated with a suboptimal concentration of mAb specific for mouse CD3 in the presence of mB7-H1Ig or mAb specific for mouse CD28. Expression of CD40L on T cells was detected with a mAb specific for mouse CD40L by FFC. mB7-H1Ig co-stimulation upregulated CD40L rapidly (25.3% after 4 h incubation) compared to co-stimulation with control IgG (6.6%) or antibody specific for mouse CD28 (10.5%) (FIG. 23a). The level of CD40L was also higher after 24 h on T cells co-stimulated with mB7-H1Ig than on T cells co-stimulated with the either control Ig or mB7-1Ig (FIG. 23a). Similar results were obtained with using an optimal dose of mAb specific for mouse CD3 for activation (FIG. 23b). Thus, triggering of the B7-H1 counter-receptor on T cells rapidly upregulates the expression of CD40L.

Although the invention has been described with reference to the presently preferred embodiment, it should be understood that various modifications can be made without departing from the spirit of the invention. Accordingly, the invention is limited only by the following claims.

What is claimed:

1. A method for inhibiting a co-stimulatory effect of B7-H1 on T-cells, comprising:
   contacting said B7-H1 with an isolated antibody that binds specifically to a B7-H1 polypeptide which comprises
   (a) amino acids having the sequence set forth in SEQ ID NO:1; or
   (b) amino acids that are encoded by a polynucleotide comprising nucleotides having the sequence set forth in SEQ ID NO:2,
   wherein the contacting comprises culturing the antibody with the T-cell in vitro, to thereby inhibit a co-stimulatory effect of B7-H1 on T-cells.

2. An isolated antibody that binds specifically to a B7-H1 polypeptide which comprises
   (a) amino acids having the sequence set forth in SEQ ID NO:3; or
   (b) amino acids that are encoded by a polynucleotide comprising nucleotides having the sequence set forth in SEQ ID NO:4.

3. An antibody fragment that binds specifically to a B7-H1 polypeptide which comprises
   (a) amino acids having the sequence set forth in SEQ ID NO:3; or
   (b) amino acids that are encoded by a polynucleotide comprising nucleotides having the sequence set forth in SEQ ID NO:4.

4. An isolated antibody according to claim 2 that binds specifically to the polypeptide comprising amino acids having the sequence set forth in SEQ ID NO:16.

5. An isolated antibody fragment according to claim 3 that binds specifically to the polypeptide comprising amino acids having the sequence set forth in SEQ ID NO:16.

6. A method for inhibiting a co-stimulatory effect of B7-H1 on T-cells, comprising:
   contacting said B7-H1 with an isolated antibody or an antigen binding fragment thereof which binds specifically to a soluble B7-H1 polypeptide which is not membrane-bound, wherein said soluble B7-H1 polypeptide comprises amino acid domain(s) having the sequence(s) shown in FIG. 2A (SEQ ID NO:1) such that the polypeptide is soluble, to thereby inhibit a co-stimulatory effect of B7-H1 on T-cells.

* * * * *

SEQUENCE LISTING

```
<160> NUMBER OF SEQ ID NOS: 18

<210> SEQ ID NO 1
<211> LENGTH: 290
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80
```

```
Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 2
<211> LENGTH: 870
<212> TYPE: DNA
<213> ORGANISM: Homo sapiens

<400> SEQUENCE: 2
atgaggatat ttgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg ctgcactaa ttgtctattg ggaaatggag      180
gataagaaca ttattcaatt tgtgcatgga gaggaagacc tgaaggttca gcatagtagc     240
tacagacaga gggcccggct gttgaaggac cagctctccc tgggaaatgc tgcacttcag     300
atcacagatg tgaaattgca ggatgcaggg gtgtaccgct gcatgatcag ctatggtggt     360
gccgactaca gcgaattac tgtgaaagtc aatgccccat acaacaaaat caaccaaaga      420
attttggttg tggatccagt cacctctgaa catgaactga catgtcaggc tgagggctac     480
cccaaggccg aagtcatctg gacaagcagt gaccatcaag tcctgagtgg taagaccacc     540
accaccaatt ccaagagaga ggagaagctt ttcaatgtga ccagcacact gagaatcaac     600
acaacaacta tgagattttt ctactgcact tttaggagat tagatcctga ggaaaaccat     660
acagctgaat tggtcatccc agaactacct ctggcacatc ctccaaatga aaggactcac     720
ttggtaattc tgggagccat cttattatgc cttggtgtag cactgacatt catcttccgt     780
ttaagaaaag ggagaatgat ggatgtgaaa aaatgtggca tccaagatac aaactcaaag     840
aagcaaagtg atacacattt ggaggagacg                                      870
```

```
<210> SEQ ID NO 3
<211> LENGTH: 290
<212> TYPE: PRT
<213> ORGANISM: Mus musculus

<400> SEQUENCE: 3

Met Arg Ile Phe Ala Gly Ile Ile Phe Thr Ala Cys Cys His Leu Leu
 1               5                  10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290

<210> SEQ ID NO 4
<211> LENGTH: 873
<212> TYPE: DNA
<213> ORGANISM: Mus musculus
<220> FEATURE:
<221> NAME/KEY: CDS
<222> LOCATION: (1)...(870)

<400> SEQUENCE: 4 atg agg ata ttt gct ggc att ata ttc aca gcc tgc tgt cac ttg cta    48
Met Arg Ile Phe Ala Gly Ile Ile Phe Thr Ala Cys Cys His Leu Leu
 1               5                  10                  15
```

| | | |
|---|---|---|
| cgg gcg ttt act atc acg gct cca aag gac ttg tac gtg gtg gag tat<br>Arg Ala Phe Thr Ile Thr Ala Pro Lys Asp Leu Tyr Val Val Glu Tyr<br>20              25                  30 | | 96 |
| ggc agc aac gtc acg atg gag tgc aga ttc cct gta gaa cgg gag ctg<br>Gly Ser Asn Val Thr Met Glu Cys Arg Phe Pro Val Glu Arg Glu Leu<br>        35              40                  45 | | 144 |
| gac ctg ctt gcg tta gtg gta tac tgg gaa aag gaa gat gag caa gtg<br>Asp Leu Leu Ala Leu Val Val Tyr Trp Glu Lys Glu Asp Glu Gln Val<br>50              55                  60 | | 192 |
| att cag ttt gtg gca gga gag gag gac ctt aag cct cag cac agc aac<br>Ile Gln Phe Val Ala Gly Glu Glu Asp Leu Lys Pro Gln His Ser Asn<br>65              70                  75              80 | | 240 |
| ttc agg ggg aga gcc tcg ctg cca aag gac cag ctt ttg aag gga aat<br>Phe Arg Gly Arg Ala Ser Leu Pro Lys Asp Gln Leu Leu Lys Gly Asn<br>        85                  90                  95 | | 288 |
| gct gcc ctt cag atc aca gac gtc aag ctg cag gac gca ggc gtt tac<br>Ala Ala Leu Gln Ile Thr Asp Val Lys Leu Gln Asp Ala Gly Val Tyr<br>        100                 105                 110 | | 336 |
| tgc tgc ata atc agc tac ggt ggt gcg gac tac aag cga atc acg ctg<br>Cys Cys Ile Ile Ser Tyr Gly Gly Ala Asp Tyr Lys Arg Ile Thr Leu<br>            115                 120                 125 | | 384 |
| aaa gtc aat gcc cca tac cgc aaa atc aac cag aga att tcc gtg gat<br>Lys Val Asn Ala Pro Tyr Arg Lys Ile Asn Gln Arg Ile Ser Val Asp<br>130                 135                 140 | | 432 |
| cca gcc act tct gag cat gaa cta ata tgt cag gcc gag ggt tat cca<br>Pro Ala Thr Ser Glu His Glu Leu Ile Cys Gln Ala Glu Gly Tyr Pro<br>145                 150                 155                 160 | | 480 |
| gaa gct gag gta atc tgg aca aac agt gac cac caa ccc gtg agt ggg<br>Glu Ala Glu Val Ile Trp Thr Asn Ser Asp His Gln Pro Val Ser Gly<br>            165                 170                 175 | | 528 |
| aag aga agt gtc acc act tcc cgg aca gag ggg atg ctt ctc aat gtg<br>Lys Arg Ser Val Thr Thr Ser Arg Thr Glu Gly Met Leu Leu Asn Val<br>        180                 185                 190 | | 576 |
| acc agc agt ctg agg gtc aac gcc aca gcg aat gat gtt ttc tac tgt<br>Thr Ser Ser Leu Arg Val Asn Ala Thr Ala Asn Asp Val Phe Tyr Cys<br>        195                 200                 205 | | 624 |
| acg ttt tgg aga tca cag cca ggg caa aac cac aca gcg gag ctg atc<br>Thr Phe Trp Arg Ser Gln Pro Gly Gln Asn His Thr Ala Glu Leu Ile<br>210                 215                 220 | | 672 |
| atc cca gaa ctg cct gca aca cat cct cca cag aac agg act cac tgg<br>Ile Pro Glu Leu Pro Ala Thr His Pro Pro Gln Asn Arg Thr His Trp<br>225                 230                 235                 240 | | 720 |
| gtg ctt ctg gga tcc atc ctg ttg ttc ctc att gta gtg tcc acg gtc<br>Val Leu Leu Gly Ser Ile Leu Leu Phe Leu Ile Val Val Ser Thr Val<br>            245                 250                 255 | | 768 |
| ctc ctc ttc ttg aga aaa caa gtg aga atg cta gat gtg gag aaa tgt<br>Leu Leu Phe Leu Arg Lys Gln Val Arg Met Leu Asp Val Glu Lys Cys<br>        260                 265                 270 | | 816 |
| ggc gtt gaa gat aca agc tca aaa aac cga aat gat aca caa ttc gag<br>Gly Val Glu Asp Thr Ser Ser Lys Asn Arg Asn Asp Thr Gln Phe Glu<br>        275                 280                 285 | | 864 |
| gag acg taa<br>Glu Thr<br>    290 | | 873 |

<210> SEQ ID NO 5
<211> LENGTH: 3616
<212> TYPE: DNA
<213> ORGANISM: Homo sapiens
<220> FEATURE:
<221> NAME/KEY: CDS
<222> LOCATION: (73)...(942)

<400> SEQUENCE: 5

```
cccacgcgtc cgcagcttcc cgaggctccg caccagccgc gcttctgtcc gcctgcaggg        60
cattccagaa ag atg agg ata ttt gct gtc ttt ata ttc atg acc tac tgg       111
              Met Arg Ile Phe Ala Val Phe Ile Phe Met Thr Tyr Trp
                1               5                  10 cat ttg ctg aac gca ttt act gtc acg gtt ccc aag gac cta tat gtg         159
His Leu Leu Asn Ala Phe Thr Val Thr Val Pro Lys Asp Leu Tyr Val
 15                  20                  25 gta gag tat ggt agc aat atg aca att gaa tgc aaa ttc cca gta gaa         207
Val Glu Tyr Gly Ser Asn Met Thr Ile Glu Cys Lys Phe Pro Val Glu
 30                  35                  40                  45 aaa caa tta gac ctg gct gca cta att gtc tat tgg gaa atg gag gat         255
Lys Gln Leu Asp Leu Ala Ala Leu Ile Val Tyr Trp Glu Met Glu Asp
                 50                  55                  60 aag aac att att caa ttt gtg cat gga gag gaa gac ctg aag gtt cag         303
Lys Asn Ile Ile Gln Phe Val His Gly Glu Glu Asp Leu Lys Val Gln
                 65                  70                  75 cat agt agc tac aga cag agg gcc cgg ctg ttg aag gac cag ctc tcc         351
His Ser Ser Tyr Arg Gln Arg Ala Arg Leu Leu Lys Asp Gln Leu Ser
             80                  85                  90 ctg gga aat gct gca ctt cag atc aca gat gtg aaa ttg cag gat gca         399
Leu Gly Asn Ala Ala Leu Gln Ile Thr Asp Val Lys Leu Gln Asp Ala
         95                 100                 105 ggg gtg tac cgc tgc atg atc agc tat ggt ggt gcc gac tac aag cga         447
Gly Val Tyr Arg Cys Met Ile Ser Tyr Gly Gly Ala Asp Tyr Lys Arg
110                 115                 120                 125 att act gtg aaa gtc aat gcc cca tac aac aaa atc aac caa aga att         495
Ile Thr Val Lys Val Asn Ala Pro Tyr Asn Lys Ile Asn Gln Arg Ile
                130                 135                 140 ttg gtt gtg gat cca gtc acc tct gaa cat gaa ctg aca tgt cag gct         543
Leu Val Val Asp Pro Val Thr Ser Glu His Glu Leu Thr Cys Gln Ala
                145                 150                 155 gag ggc tac ccc aag gcc gaa gtc atc tgg aca agc agt gac cat caa         591
Glu Gly Tyr Pro Lys Ala Glu Val Ile Trp Thr Ser Ser Asp His Gln
            160                 165                 170 gtc ctg agt ggt aag acc acc acc acc aat tcc aag aga gag gag aag         639
Val Leu Ser Gly Lys Thr Thr Thr Thr Asn Ser Lys Arg Glu Glu Lys
        175                 180                 185 ctt ttc aat gtg acc agc aca ctg aga atc aac aca aca act aat gag         687
Leu Phe Asn Val Thr Ser Thr Leu Arg Ile Asn Thr Thr Thr Asn Glu
190                 195                 200                 205 att ttc tac tgc act ttt agg aga tta gat cct gag gaa aac cat aca         735
Ile Phe Tyr Cys Thr Phe Arg Arg Leu Asp Pro Glu Glu Asn His Thr
                210                 215                 220 gct gaa ttg gtc atc cca gaa cta cct ctg gca cat cct cca aat gaa         783
Ala Glu Leu Val Ile Pro Glu Leu Pro Leu Ala His Pro Pro Asn Glu
                225                 230                 235 agg act cac ttg gta att ctg gga gcc atc tta tta tgc ctt ggt gta         831
Arg Thr His Leu Val Ile Leu Gly Ala Ile Leu Leu Cys Leu Gly Val
            240                 245                 250 gca ctg aca ttc atc ttc cgt tta aga aaa ggg aga atg atg gat gtg         879
Ala Leu Thr Phe Ile Phe Arg Leu Arg Lys Gly Arg Met Met Asp Val
255                 260                 265 aaa aaa tgt ggc atc caa gat aca aac tca aag aag caa agt gat aca         927
Lys Lys Cys Gly Ile Gln Asp Thr Asn Ser Lys Lys Gln Ser Asp Thr
270                 275                 280                 285 cat ttg gag gag acg taatccagca ttggaacttc tgatcttcaa gcagggattc         982
His Leu Glu Glu Thr
            290
```

```
tcaacctgtg gtttaggggt tcatcggggc tgagcgtgac aagaggaagg aatggacccg    1042
tgggatgcag gcaatgtggg acttaaaagg cccaagcact gaaaatggaa cctggcgaaa    1102
gcagaggagg agaatgaaga aagatggagt caaacaggga gcctggaggg agaccttgat    1162
actttcaaat gcctgagggg ctcatcgacg cctgtgacag ggagaaagga tacttctgaa    1222
caaggagcct ccaagcaaat catccattgc tcatcctagg aagacgggtt gagaatccct    1282
aatttgaggg tcagttcctg cagaagtgcc ctttgcctcc actcaatgcc tcaatttctt    1342
ttctgcatga ctgagagtct cagtgttgga acgggacagt atttatgtat gagttttcc     1402 tatttatttt gagtctgtga ggtcttcttg tcatgtgagt gtggttgtga atgatttctt    1462
ttgaagatat attgtagtag atgttacaat tttgtcgcca aactaaactt gctgcttaat    1522
gatttgctca catctagtaa aacatggagt atttgtaagg tgcttggtct cctctataac    1582
tacaagtata cattggaagc ataaagatca aaccgttggt tgcataggat gtcacccttta   1642 tttaacccat taatactctg gttgacctaa tcttattctc agacctcaag tgtctgtgca    1702
gtatctgttc catttaaata tcagctttac aattatgtgg tagcctacac acataatctc    1762
atttcatcgc tgtaaccacc ctgttgtgat aaccactatt atttaccca tcgtacagct     1822 gaggaagcaa acagattaag taacttgccc aaaccagtaa atagcagacc tcagactgcc    1882
acccactgtc cttttataat acaatttaca gctatatttt actttaagca attcttttat    1942
tcaaaaacca tttattaagt gcccttgcaa tatcaatcgc tgtgccaggc attgaatcta    2002
cagatgtgag caagacaaag tacctgtcct caaggagctc atagtataat gaggagatta    2062
acaagaaaat gtattattac aatttagtcc agtgtcatag cataaggatg atgcgagggg    2122
aaaacccgag cagtgttgcc aagaggagga aataggccaa tgtggtctgg gacggttgga    2182
tatacttaaa catcttaata atcagagtaa ttttcattta caaagagagg tcggtactta    2242
aaataaccct gaaaaataac actggaattc cttttctagc attatatta ttcctgattt      2302 gccttttgcca tataatctaa tgcttgttta tatagtgtct ggtattgttt aacagttctg    2362
tcttttctat ttaaatgcca ctaaatttta aattcatacc tttccatgat tcaaaattca    2422
aaagatccca tgggagatgg ttggaaaatc tccacttcat cctccaagcc attcaagttt    2482
cctttccaga agcaactgct actgcctttc attcatatgt tcttctaaag atagtctaca    2542
tttggaaatg tatgttaaaa gcacgtattt ttaaaatttt tttcctaaat agtaacacat    2602
tgtatgtctg ctgtgtactt tgctattttt atttatttta gtgtttctta tatagcagat    2662
ggaatgaatt tgaagttccc agggctgagg atccatgcct tctttgtttc taagttatct    2722
ttcccatagc ttttcattat ctttcatatg atccagtata tgttaaatat gtcctacata    2782
tacatttaga caaccaccat tgttaagta tttgctctag  gacagagttt ggatttgttt    2842
atgtttgctc aaaaggagac ccatgggctc tccagggtgc actgagtcaa tctagtccta    2902
aaaagcaatc ttattattaa ctctgtatga cagaatcatg tctggaactt tgttttctg     2962 ctttctgtca agtataaact tcactttgat gctgtacttg caaaatcaca ttttctttct    3022
ggaaattccg gcagtgtacc ttgactgcta gctaccctgt gccagaaaag cctcattcgt    3082
tgtgcttgaa cccttgaatg ccaccagctg tcatcactac acagccctcc taagaggctt    3142
cctggaggtt tcgagattca gatgccctgg gagatcccag agtttccttt ccctcttggc    3202
catattctgg tgtcaatgac aaggagtacc ttggctttgc cacatgtcaa ggctgaagaa    3262
acagtgtctc caacagagct ccttgtgtta tctgtttgta catgtgcatt tgtacagtaa    3322
ttggtgtgac agtgttcttt gtgtgaatta caggcaagaa ttgtggctga gcaaggcaca    3382
```
tagtctactc agtctattcc taagtcctaa ctcctccttg tggtgttgga tttgtaaggc    3442
actttatccc ttttgtctca tgtttcatcg taaatggcat aggcagagat gatacctaat    3502
tctgcatttg attgtcactt tttgtacctg cattaattta ataaatatt cttatttatt    3562 ttgttacttg gtaaaaaaaa aaaaaaaaaa aaaaaaaaaa aaaaaaaaaa aaaa          3616

<210> SEQ ID NO 6
<211> LENGTH: 25
<212> TYPE: PRT
<213> ORGANISM: Homo sapiens

<400> SEQUENCE: 6

Met Ala Ile Ser Gly Val Pro Val Leu Gly Phe Phe Ile Ile Ala Val
1               5                   10                  15

Leu Met Ser Ala Gln Glu Ser Trp Ala
            20                  25

<210> SEQ ID NO 7
<211> LENGTH: 5
<212> TYPE: PRT
<213> ORGANISM: Bovidae

<400> SEQUENCE: 7

Lys Phe Glu Arg Gln
1               5

<210> SEQ ID NO 8
<211> LENGTH: 15
<212> TYPE: PRT
<213> ORGANISM: Homo sapiens

<400> SEQUENCE: 8

Met Asp Asp Gln Arg Asp Leu Ile Ser Asn Asn Glu Gln Leu Pro
1               5                   10                  15

<210> SEQ ID NO 9
<211> LENGTH: 4
<212> TYPE: PRT
<213> ORGANISM: Rattus rattus

<400> SEQUENCE: 9

Lys Asp Glu Leu
1

<210> SEQ ID NO 10
<211> LENGTH: 210
<212> TYPE: PRT
<213> ORGANISM: Homo sapiens

<400> SEQUENCE: 10

Val Glu Tyr Gly Ser Asn Met Thr Ile Glu Cys Lys Phe Pro Val Glu
1               5                   10                  15

Lys Gln Leu Asp Leu Ala Ala Leu Ile Val Tyr Trp Glu Met Glu Asp
            20                  25                  30

Lys Asn Ile Ile Gln Phe Val His Gly Glu Glu Asp Leu Lys Val Gln
        35                  40                  45

His Ser Ser Tyr Arg Gln Arg Ala Arg Leu Leu Lys Asp Gln Leu Ser
    50                  55                  60

Leu Gly Asn Ala Ala Leu Gln Ile Thr Asp Val Lys Leu Gln Asp Ala
65                  70                  75                  80

Gly Val Tyr Arg Cys Met Ile Ser Tyr Gly Gly Ala Asp Tyr Lys Arg

```
                    85                  90                  95
Ile Thr Val Lys Val Asn Ala Pro Tyr Asn Lys Ile Asn Gln Arg Ile
                100                 105                 110

Leu Val Val Asp Pro Val Thr Ser Glu His Glu Leu Thr Cys Gln Ala
            115                 120                 125

Glu Gly Tyr Pro Lys Ala Glu Val Ile Trp Thr Ser Ser Asp His Gln
        130                 135                 140

Val Leu Ser Gly Lys Thr Thr Thr Asn Ser Lys Arg Glu Glu Lys
145                 150                 155                 160

Leu Phe Asn Val Thr Ser Thr Leu Arg Ile Asn Thr Thr Thr Asn Glu
                165                 170                 175

Ile Phe Tyr Cys Thr Phe Arg Arg Leu Asp Pro Glu Glu Asn His Thr
            180                 185                 190

Ala Glu Leu Val Ile Pro Glu Leu Pro Leu Ala His Pro Pro Asn Glu
        195                 200                 205

Arg Thr
    210

<210> SEQ ID NO 11
<211> LENGTH: 205
<212> TYPE: PRT
<213> ORGANISM: Homo sapiens

<400> SEQUENCE: 11

Lys Glu Val Lys Glu Val Ala Thr Leu Ser Cys Gly His Asn Val Ser
  1               5                  10                  15

Val Glu Glu Leu Ala Gln Thr Arg Ile Tyr Trp Gln Lys Glu Lys Lys
            20                  25                  30

Met Val Leu Thr Met Met Ser Gly Asp Met Asn Ile Trp Pro Glu Tyr
        35                  40                  45

Lys Asn Arg Thr Ile Phe Asp Ile Thr Asn Asn Leu Ser Ile Val Ile
    50                  55                  60

Leu Ala Leu Arg Pro Ser Asp Glu Gly Thr Tyr Glu Cys Val Val Leu
65                  70                  75                  80

Lys Tyr Glu Lys Asp Ala Phe Lys Arg Glu His Leu Ala Glu Val Thr
                85                  90                  95

Leu Ser Val Lys Ala Asp Phe Pro Thr Pro Ser Ile Ser Asp Phe Glu
                100                 105                 110

Ile Pro Thr Ser Asn Ile Arg Arg Ile Ile Cys Ser Thr Ser Gly Gly
            115                 120                 125

Phe Pro Glu Pro His Leu Ser Trp Leu Glu Asn Gly Glu Glu Leu Asn
        130                 135                 140

Ala Ile Asn Thr Thr Val Ser Gln Asp Pro Glu Thr Glu Leu Tyr Ala
145                 150                 155                 160

Val Ser Ser Lys Leu Asp Phe Asn Met Thr Thr Asn His Ser Phe Met
                165                 170                 175

Cys Leu Ile Lys Tyr Gly His Leu Arg Val Asn Gln Thr Phe Asn Trp
            180                 185                 190

Asn Thr Thr Lys Gln Glu His Phe Pro Asp Asn Leu Leu
        195                 200                 205

<210> SEQ ID NO 12
<211> LENGTH: 218
<212> TYPE: PRT
<213> ORGANISM: Homo sapiens

<400> SEQUENCE: 12
```

```
Ala Tyr Phe Asn Glu Thr Ala Asp Leu Pro Cys Gln Phe Ala Asn Ser
  1               5                  10                  15

Gln Asn Gln Ser Leu Ser Glu Leu Val Val Phe Trp Gln Asp Gln Glu
             20                  25                  30

Asn Leu Val Leu Asn Glu Val Tyr Leu Gly Lys Glu Lys Phe Asp Ser
         35                  40                  45

Val His Ser Lys Tyr Met Gly Arg Thr Ser Phe Asp Ser Asp Ser Trp
     50                  55                  60

Thr Leu Arg Leu His Asn Leu Gln Ile Lys Asp Lys Gly Leu Tyr Gln
 65                  70                  75                  80

Cys Ile Ile His His Lys Lys Pro Thr Gly Met Ile Arg Ile His Gln
                 85                  90                  95

Met Asn Ser Glu Leu Ser Val Leu Ala Asn Phe Ser Gln Pro Glu Ile
            100                 105                 110

Val Pro Ile Ser Asn Ile Thr Glu Asn Val Tyr Ile Asn Leu Thr Cys
        115                 120                 125

Ser Ser Ile His Gly Tyr Pro Glu Pro Lys Lys Met Ser Val Leu Leu
130                 135                 140

Arg Thr Lys Asn Ser Thr Ile Glu Tyr Asp Gly Ile Met Gln Lys Ser
145                 150                 155                 160

Gln Asp Asn Val Thr Glu Leu Tyr Asp Val Ser Ile Ser Leu Ser Val
                165                 170                 175

Ser Phe Pro Asp Val Thr Ser Asn Met Thr Ile Phe Cys Ile Leu Glu
            180                 185                 190

Thr Asp Lys Thr Arg Leu Leu Ser Ser Pro Phe Ser Ile Glu Leu Glu
        195                 200                 205

Asp Pro Gln Pro Pro Asp His Ile Pro
    210                 215
```

<210> SEQ ID NO 13
<211> LENGTH: 306
<212> TYPE: PRT
<213> ORGANISM: Mus musculus

<400> SEQUENCE: 13

```
Met Ala Cys Asn Cys Gln Leu Met Gln Asp Thr Pro Leu Leu Lys Phe
  1               5                  10                  15

Pro Cys Pro Arg Leu Ile Leu Leu Phe Val Leu Leu Ile Arg Leu Ser
             20                  25                  30

Gln Val Ser Ser Asp Val Asp Glu Gln Leu Ser Lys Ser Val Lys Asp
         35                  40                  45

Lys Val Leu Leu Pro Cys Arg Tyr Asn Ser Pro His Glu Asp Glu Ser
     50                  55                  60

Glu Asp Arg Ile Tyr Trp Gln Lys His Asp Lys Val Val Leu Ser Val
 65                  70                  75                  80

Ile Ala Gly Lys Leu Lys Val Trp Pro Glu Tyr Lys Asn Arg Thr Leu
                 85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
130                 135                 140

Phe Ser Thr Pro Asn Ile Thr Glu Ser Gly Asn Pro Ser Ala Asp Thr
145                 150                 155                 160
```

-continued

```
Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Ile Val Ile Ile Lys Cys Phe Cys
            260                 265                 270

Lys His Arg Ser Cys Phe Arg Arg Asn Glu Ala Ser Arg Glu Thr Asn
                275                 280                 285

Asn Ser Leu Thr Phe Gly Pro Glu Glu Ala Leu Ala Glu Gln Thr Val
            290                 295                 300

Phe Leu
305

<210> SEQ ID NO 14
<211> LENGTH: 309
<212> TYPE: PRT
<213> ORGANISM: Mus musculus

<400> SEQUENCE: 14

Met Asp Pro Arg Cys Thr Met Gly Leu Ala Ile Leu Ile Phe Val Thr
  1               5                  10                  15

Val Leu Leu Ile Ser Asp Ala Val Ser Val Glu Thr Gln Ala Tyr Phe
             20                  25                  30

Asn Gly Thr Ala Tyr Leu Pro Cys Pro Phe Thr Lys Ala Gln Asn Ile
         35                  40                  45

Ser Leu Ser Glu Leu Val Val Phe Trp Gln Asp Gln Gln Lys Leu Val
     50                  55                  60

Leu Tyr Glu His Tyr Leu Gly Thr Glu Lys Leu Asp Ser Val Asn Ala
 65                  70                  75                  80

Lys Tyr Leu Gly Arg Thr Ser Phe Asp Arg Asn Asn Trp Thr Leu Arg
                 85                  90                  95

Leu His Asn Val Gln Ile Lys Asp Met Gly Ser Tyr Asp Cys Phe Ile
            100                 105                 110

Gln Lys Lys Pro Pro Thr Gly Ser Ile Ile Leu Gln Gln Thr Leu Thr
        115                 120                 125

Glu Leu Ser Val Ile Ala Asn Phe Ser Glu Pro Glu Ile Lys Leu Ala
    130                 135                 140

Gln Asn Val Thr Gly Asn Ser Gly Ile Asn Leu Thr Cys Thr Ser Lys
145                 150                 155                 160

Gln Gly His Pro Lys Pro Lys Lys Met Tyr Phe Leu Ile Thr Asn Ser
                165                 170                 175

Thr Asn Glu Tyr Gly Asp Asn Met Gln Ile Ser Gln Asp Asn Val Thr
            180                 185                 190

Glu Leu Phe Ser Ile Ser Asn Ser Leu Ser Leu Ser Phe Pro Asp Gly
        195                 200                 205

Val Trp His Met Thr Val Val Cys Val Leu Glu Thr Glu Ser Met Lys
    210                 215                 220
```

```
Ile Ser Ser Lys Pro Leu Asn Phe Thr Gln Glu Phe Pro Ser Pro Gln
225                 230                 235                 240

Thr Tyr Trp Lys Glu Ile Thr Ala Ser Val Thr Val Ala Leu Leu Leu
            245                 250                 255

Val Met Leu Leu Ile Ile Val Cys His Lys Lys Pro Asn Gln Pro Ser
        260                 265                 270

Arg Pro Ser Asn Thr Ala Ser Lys Leu Glu Arg Asp Ser Asn Ala Asp
    275                 280                 285

Arg Glu Thr Ile Asn Leu Lys Glu Leu Glu Pro Gln Ile Ala Ser Ala
290                 295                 300

Lys Pro Asn Ala Glu
305

<210> SEQ ID NO 15
<211> LENGTH: 322
<212> TYPE: PRT
<213> ORGANISM: Mus musculus

<400> SEQUENCE: 15

Met Gln Leu Lys Cys Pro Cys Phe Val Ser Leu Gly Thr Arg Gln Pro
1               5                   10                  15

Val Trp Lys Lys Leu His Val Ser Ser Gly Phe Phe Ser Gly Leu Gly
            20                  25                  30

Leu Phe Leu Leu Leu Leu Ser Ser Leu Cys Ala Ala Ser Ala Glu Thr
        35                  40                  45

Glu Val Gly Ala Met Val Gly Ser Asn Val Val Leu Ser Cys Ile Asp
    50                  55                  60

Pro His Arg Arg His Phe Asn Leu Ser Gly Leu Tyr Val Tyr Trp Gln
65                  70                  75                  80

Ile Glu Asn Pro Glu Val Ser Val Thr Tyr Tyr Leu Pro Tyr Lys Ser
                85                  90                  95

Pro Gly Ile Asn Val Asp Ser Ser Tyr Lys Asn Arg Gly His Leu Ser
            100                 105                 110

Leu Asp Ser Met Lys Gln Gly Asn Phe Ser Leu Tyr Leu Lys Asn Val
        115                 120                 125

Thr Pro Gln Asp Thr Gln Glu Phe Thr Cys Arg Val Phe Met Asn Thr
    130                 135                 140

Ala Thr Glu Leu Val Lys Ile Leu Glu Glu Val Val Arg Leu Arg Val
145                 150                 155                 160

Ala Ala Asn Phe Ser Thr Pro Val Ile Ser Thr Ser Asp Ser Ser Asn
                165                 170                 175

Pro Gly Gln Glu Arg Thr Tyr Thr Cys Met Ser Lys Asn Gly Tyr Pro
            180                 185                 190

Glu Pro Asn Leu Tyr Trp Ile Asn Thr Thr Asp Asn Ser Leu Ile Asp
        195                 200                 205

Thr Ala Leu Gln Asn Asn Thr Val Tyr Leu Asn Lys Leu Gly Leu Tyr
    210                 215                 220

Asp Val Ile Ser Thr Leu Arg Leu Pro Trp Thr Ser Arg Gly Asp Val
225                 230                 235                 240

Leu Cys Cys Val Glu Asn Val Ala Leu His Gln Asn Ile Thr Ser Ile
                245                 250                 255

Ser Gln Ala Glu Ser Phe Thr Gly Asn Asn Thr Lys Asn Pro Gln Glu
            260                 265                 270

Thr His Asn Asn Glu Leu Lys Val Leu Val Pro Val Leu Ala Val Leu
        275                 280                 285
```

```
Ala Ala Ala Ala Phe Val Ser Phe Ile Ile Tyr Arg Arg Thr Arg Pro
    290                 295                 300

His Arg Ser Tyr Thr Gly Pro Lys Thr Val Gln Leu Glu Leu Thr Asp
305                 310                 315                 320

His Ala

<210> SEQ ID NO 16
<211> LENGTH: 25
<212> TYPE: PRT
<213> ORGANISM: Mus musculus

<400> SEQUENCE: 16

Gly Asn Ala Ala Leu Gln Ile Thr Asp Val Lys Leu Gln Asp Ala Gly
  1               5                  10                  15

Val Tyr Cys Cys Ile Ile Ser Tyr Gly
             20                  25

<210> SEQ ID NO 17
<211> LENGTH: 28
<212> TYPE: DNA
<213> ORGANISM: Mus musculus

<400> SEQUENCE: 17
caggaattca ccatgaggat atttgctg                                       28

<210> SEQ ID NO 18
<211> LENGTH: 29
<212> TYPE: DNA
<213> ORGANISM: Mus musculus

<400> SEQUENCE: 18
catcagatct atgtgagtcc tgttctgtg                                      29
```